US007608406B2

(12) United States Patent
Valkirs et al.

(10) Patent No.: US 7,608,406 B2
(45) Date of Patent: Oct. 27, 2009

(54) DIAGNOSTIC MARKERS OF STROKE AND CEREBRAL INJURY AND METHODS OF USE THEREOF

(75) Inventors: Gunars E. Valkirs, Escondido, CA (US); Jeffrey R. Dahlen, San Diego, CA (US); Howard J. Kirchick, San Diego, CA (US); Kenneth F. Buechler, Rancho Santa Fe, CA (US)

(73) Assignee: Biosite, Inc., Waltham, MA (US)

( * ) Notice: Subject to any disclaimer, the term of this patent is extended or adjusted under 35 U.S.C. 154(b) by 306 days.

(21) Appl. No.: 10/875,800

(22) Filed: Jun. 23, 2004

(65) Prior Publication Data

US 2005/0255484 A1 Nov. 17, 2005

Related U.S. Application Data

(63) Continuation-in-part of application No. 10/714,078, filed on Nov. 14, 2003, which is a continuation-in-part of application No. 10/673,077, filed on Sep. 26, 2003, which is a continuation-in-part of application No. 10/371,149, filed on Feb. 20, 2003, which is a continuation-in-part of application No. PCT/US02/26604, filed on Aug. 20, 2002, said application No. 10/371, 149 is a continuation-in-part of application No. 10/225,082, filed on Aug. 20, 2002.

(60) Provisional application No. 60/313,775, filed on Aug. 20, 2001, provisional application No. 60/334,964, filed on Nov. 30, 2001, provisional application No. 60/346,485, filed on Jan. 2, 2002.

(51) Int. Cl.
*G01N 33/53* (2006.01)

(52) U.S. Cl. ..................... 435/7.1; 435/7.21; 436/501; 436/518; 424/9.1

(58) Field of Classification Search ........................ None
See application file for complete search history.

(56) References Cited

U.S. PATENT DOCUMENTS

| 4,447,545 | A | 5/1984 | DeFazio et al. |
| 4,900,662 | A | 2/1990 | Shah et al. |
| 5,202,234 | A | 4/1993 | Shah et al. |
| 5,206,140 | A | 4/1993 | Marder et al. |
| 5,290,678 | A | 3/1994 | Jackowski |
| 5,294,537 | A | 3/1994 | Batt |
| 5,350,842 | A | 9/1994 | Norgard |
| 5,352,587 | A | 10/1994 | Chang et al. |
| 5,382,515 | A | 1/1995 | Shah et al. |
| 5,382,522 | A | 1/1995 | Shah et al. |
| 5,422,393 | A | 6/1995 | Bricker et al. |
| 5,690,103 | A | 11/1997 | Groth et al. |
| 5,786,163 | A | 7/1998 | Hall |
| 5,795,725 | A | 8/1998 | Buechler et al. |
| 5,843,690 | A | 12/1998 | Gargan |
| 6,099,469 | A | 8/2000 | Armstrong et al. |
| 6,117,744 | A | 9/2000 | Debold |
| 6,124,430 | A | 9/2000 | Mischak et al. |
| 6,156,521 | A | 12/2000 | Buechler et al. |
| 6,174,686 | B1 | 1/2001 | Buechler et al. |
| 6,235,489 | B1 | 5/2001 | Jackowski |
| 6,309,888 | B1 | 10/2001 | Holvoet et al. |
| 6,443,889 | B1 | 9/2002 | Groth et al. |
| 6,461,828 | B1 | 10/2002 | Stanton et al. |
| 6,579,687 | B1 | 6/2003 | Buechler et al. |
| 6,586,244 | B2 | 7/2003 | Reinhard |
| 6,627,404 | B1 | 9/2003 | Buechler et al. |
| 6,627,457 | B2 * | 9/2003 | Pandian et al. .............. 436/501 |
| 6,670,138 | B2 * | 12/2003 | Gonzalez-Zulueta et al. . 435/7.1 |
| 6,828,107 | B2 | 12/2004 | Asada et al. |
| 6,897,030 | B2 | 5/2005 | Seilhamer et al. |
| 6,939,678 | B1 | 9/2005 | Buechler et al. |
| 6,991,907 | B1 | 1/2006 | Buechler et al. |
| 7,341,838 | B2 | 3/2008 | Buechler et al. |
| 7,358,055 | B2 | 4/2008 | Valkirs et al. |
| 7,361,473 | B2 | 4/2008 | Valkirs et al. |
| 2003/0022235 | A1 | 1/2003 | Dahlen et al. |
| 2003/0119064 | A1 | 6/2003 | Valkirs et al. |

(Continued)

FOREIGN PATENT DOCUMENTS

WO     WO 96/32648 A1    10/1996

(Continued)

OTHER PUBLICATIONS

Tervaert (JN Journal of Nephrology, 1996, vol. 9, No. 5, pp. 232-240).*
Cuzzocrea et al. (Brain Research, vol. 875, 2000, pp. 96-106).*
Roger et al. (Journal of the American College of Cardiology, 1999, vol. 34, No. 1, pp. 155-162).*
Griffin et al. (Kidney International, vol. 55, 1999, pp. 917-925).*
Minota et al. (Scandinavian Journal of Rheumatology, 1999, vol. 28, pp. 94-99).*

(Continued)

*Primary Examiner*—Lisa V Cook
(74) *Attorney, Agent, or Firm*—Anavelys Ortiz-Suarez; Wilson Sonsini Goodrich & Rosati

(57) ABSTRACT

The present invention relates to methods for the diagnosis and evaluation of stroke and transient ischemic attacks. A variety of markers are disclosed for assembling a panel for such diagnosis and evaluation. In various aspects, the invention provides methods for early detection and differentiation of stroke types and transient ischemic attacks, for determining the prognosis of a patient presenting with stroke symptoms, and identifying a patient at risk for cerebral vasospasm. Invention methods provide rapid, sensitive and specific assays to greatly increase the number of patients that can receive beneficial stroke treatment and therapy, and reduce the costs associated with incorrect stroke diagnosis.

8 Claims, 7 Drawing Sheets

U.S. PATENT DOCUMENTS

| | | |
|---|---|---|
| 2003/0199000 A1 | 10/2003 | Valkirs et al. |
| 2003/0211544 A1 | 11/2003 | Buechler et al. |
| 2003/0219734 A1 | 11/2003 | Buechler |
| 2004/0072805 A1 | 4/2004 | Warren et al. |
| 2004/0121343 A1 | 6/2004 | Buechler et al. |
| 2004/0121350 A1 | 6/2004 | Anderberg et al. |
| 2004/0126767 A1 | 7/2004 | Anderberg et al. |
| 2004/0167341 A1 | 8/2004 | Haffner et al. |
| 2004/0171064 A1 | 9/2004 | Dahlen et al. |
| 2004/0176914 A1 | 9/2004 | Buechler et al. |
| 2004/0203083 A1 | 10/2004 | Buechler et al. |
| 2004/0209307 A1 | 10/2004 | Valkirs et al. |
| 2004/0219509 A1 | 11/2004 | Valkirs et al. |
| 2004/0253637 A1 | 12/2004 | Buechler et al. |
| 2005/0148024 A1 | 7/2005 | Buechler |
| 2005/0164317 A1 | 7/2005 | Buechler et al. |
| 2005/0181386 A1 | 8/2005 | Diamond et al. |
| 2006/0051825 A1 | 3/2006 | Buechler et al. |
| 2006/0105419 A1 | 5/2006 | Blankenberg et al. |
| 2007/0196880 A1 | 8/2007 | Buechler et al. |
| 2007/0218498 A1 | 9/2007 | Buechler et al. |
| 2007/0224643 A1 | 9/2007 | McPherson et al. |
| 2007/0269836 A1 | 11/2007 | McPherson |
| 2008/0045444 A1 | 2/2008 | Whittaker |
| 2008/0118924 A1 | 5/2008 | Buechler |
| 2008/0293920 A1 | 11/2008 | Buechler |

FOREIGN PATENT DOCUMENTS

| | | | |
|---|---|---|---|
| WO | WO 98/43630 A1 | | 8/1998 |
| WO | WO 99/18442 A1 | | 4/1999 |
| WO | WO 00/18801 | | 4/2000 |
| WO | WO 00/52476 | * | 9/2000 |
| WO | WO 01/14885 | | 3/2001 |
| WO | WO 02/23191 A1 | | 3/2002 |
| WO | WO 02/083913 | | 10/2002 |
| WO | WO 02/089657 A2 | | 11/2002 |
| WO | WO 02/089657 A3 | | 11/2002 |
| WO | WO 03/002553 | | 1/2003 |
| WO | WO 03/002553 A3 | | 3/2003 |

OTHER PUBLICATIONS

Christou et al. (Stroke, 2000, vol. 31, No. 8, pp. 1812-1816).*
Kikkinos et al. (Neurologic Clinics, 1993, vol. 11, No. 3, pp. 577-590, Abstract Only).*
Yakovlev et al., Activation of CPP32-Like Caspases Contributes to Neuronal Apoptosis and Neurological Dysfunction after Traumatic Brain Injury, The Journal of Neuroscience, Oct. 1, 1997, 17 (19): 7415-7424.*
Huttunen et al., Coregulation of Neurite Outgrowth and Cell Survival by Amphoterin and S100 Proteins through Receptor for Advanced glycation End Products (RAGE) Activation., Journ. of Biological Chem. vol. 275, Dec. 22, 2000, pp. 40096-40105.*
Mussack et al., early cellular brain damage and systemic inflammatory response after cardiopulmonary resuscitation or isolated severe head trauma, Resuscitation, (May 2001) vol. 49, No. 2, pp. 193-199.*
Interlinational Search Report and the Written Opinion of the International Searching Authority from PCT Application No. PCT/US04/12024.
Mussack et al., Early cellular brain damage and systemic inflammatory response after cardiopulmonary resuscitation or isolated severe head trauma: a comparative pilot study on common pathomechanisma. Resuscitation, 49:193-199, 2001.
Yakoviev et al., Activation of CPP32-Like caspases contributes to neuronal apoptosis and neurological dysfunction after traumatic brain injury. The Journal of Neuroscience, 17(19): 7415-724, 1997.
International Search Report for international application No. PCT/US04/26984.
Notice of References Cited, PTO-892, Part of Paper No. 20041202 from U.S. Appl. No. 10/225,082, filed Aug. 20, 2002.

Harter et al., Caspase-3 activity is present in cerebrospinal fluid from patients with traumatic brain injury. Journal of Neuroimmunology, 121:76-78, 2001.
Fonarow et al., "Combining Natriuretic Peptides and Necrosis Markers in Determining Prognosis in Heart Failure," Reviews in Cardiovascular Medicine, 2003, Suppl. 4, vol. 4.
Richards et al., "Neuroendocrine prediction of left ventricular function and heart failure after acute myocardial infarction," Heart, 1999, pp. 114-120, vol. 81.
Saady et al., "Left appendage: structure function, and role in thromboembolism," Heart, 1999, pp. 547-555, vol. 82.
Cassin et al., È realizzabile una strategia operative piu efficace per la gestione in urgenza del paziente con dolore toracico acuto?, Ital Heart J Suppl, Feb. 2000, pp. 186-201, vol. 1.
Futterman et al., Novel Markers in the Acute Coronary Syndrome: BNP, IL-6, PAPP-A, American Journal of Critical Care, Mar. 2002, pp. 168-172, vol. 11, No. 2.
Hunt et al., Immunoreactive amino-terminal pro-brain natriuretic peptide (NT-PROBNP): a new marker of cardiac impairment, Clinical Endocrinology, 1997, pp. 287-296, vol. 47.
Sagnella et al., Measurement and significance of circulating natriuretic peptides in cardiovascular disease, Clinical Science, Nov. 1998, pp. 519-529, vol. 95, No. 5.
Sonel et al., Prospective Study Correlating Fibrinopeptide A, Troponin I, Myoglobin, and Myosin Light Chain Levels with Early and Late Ischemic Events in Consecutive Patients Presenting to the Emergency Department with Chest Pain, Circulation, Sep. 5, 2000, pp. 1107-1113, vol. 102, No. 10.
Greenberg, Angiogenesis and stroke, Drug News and Perspectives, 11(5):265-270, 1998. (Abstract only).
Meester et al., In vivo inhibition of dipeptidyl peptidase IV activity by pro-pro-diphenyl-phosphonate (prodipine), Biochemical Pharmacology, 54:173-179, 1997.
Mills et al., Sustained hemodynamic effects of an Infusion of nesiritide (human b-type natriuretic peptide) in heart failure, Journal of the American college of cardiology, 34(1):155-162, 1999.
Yakovlev et al., Activation of CPP32-like caspases contributes to neuronal apoptosis and neurological dysfunction after traumatic brain injury, The journal of neuroscience, 17(19):7415-7424, 1997.
Supplementary European Search Report attached to Communication dated Aug. 9, 2006.
Hunter et al., "Analysis of Peptides Derived from Pro Atrial Natriuretic Peptide That Circulate in Man an Increase in Heart Disease", Scand J. Clin Lab Invest 56, 205-216 (1998).
Mills et al., "Sustained Hemodynamic Effects of an Infusion of Nesiritide (Human b-Type Natriuretic Peptide) in Heart Failure", Journal of the American College of Cardiology, vol. 34, No. 1, pp. 155-62 (1999).
Vesley et al., "Negative Feedback of Atrial Natriuretic Peptides", Journal of Clinical Endocrinology and Metabolism, vol. 78, No. 5, 1128-1134 (1994).
Baker, In Biomarkers we trust?, Nature Biotechnology, 23(3): 297-304, 2005.
Bast et al., Translational crossroads for biomarkers, Clin Cancer Research, 11(17): 6103-6108, 2005.
Corti et al., Vasopeptidase inhibitors: A New therapeutic concept in cardiovascular disease?, Circulation, 104:1856-1862, 2001.
European Search Report for EP Application No. 04781634.3-2401.
Jones et al., Hematopoietic stimulation by a dipeptidyl peptidase inhibitor reveals a novel regulatory mechanism and therapeutic treatment for blood cell deficiencies. Blood, 102(5): 1641-1648, 2003.
LaBaer, So, you want to look for biomarkers (Introduction to the special biomarkers issue), Journal of Proteome Research, 4:1053-1059, 2005.
Tarkowski et al., Intrathecal release of pro- and anti-inflammatory cytokines during stroke. Clin. Exp. Immunol. 110:492-499, 1997.
Walther et al., Biochemical analysis of neutral endopeptidase activity reveals independent catabolism of atrial and brain natriuretic peptide. Biol. Chem., 385: 179-184, Feb. 2004.
Norman et al., "Degradation of Brain Natriuretic Peptide by Neutral Endopeptidase: Species Specific Sites of Proteolysis Determined by Mass Spectrometry", Biochemical & Biophysical Research Communications, vol. 175, No. 1, (1991).

Bidzseranova et al., "Structure-activity Studies on the Effects of Atrial Natriuretic Peptide, Brain Natriuretic Peptide and Their Analogs on Fear-motivated Learning Behavior in Rats", Neuropeptides, 23, 61-65, (1992).

Definition of "appreciable." Allwords.com. Available at: http://www.allwords.com/query.php?SearchType=3&Keyword=appreciable&Language=ENG.

Definition of "tissue." Webster's II New Riverside University Dictionary, 1994, by Houghton Mifflin Company, p. 1212.

European Search Report dated Jan. 17, 2006 for EP Application No. EP02757275.9.

Feinberg, et al. Guidelines for the management of transient ischemic attacks. Stroke. Jun. 1994;25(6): 1320-1335.

International Search Report dated Dec. 20, 2002 for PCT Application No. US2002/26604.

Kelly, et al. Screening for left ventricular systolic dysfunction in patients with stroke, transient ischaemic attacks, and peripheral vascular disease. Q. J. Med. 1999;92: 295-297.

Lee, et al. Serum gelatinase B, TIMP-1 and TIMP-2 levels in multiple sclerosis. A longitudinal clinical and MRI study. Brain. Feb. 1999;122 ( Pt 2):191-7.

Liu, et al. Changes of von Willebrand factor and antithrombin III levels in acute stroke: difference between thrombotic and haemorrhagic stroke. Thromb Res. Nov. 15, 1993;72(4):353- 8.

Montaner, et al. Matrix metalloproteinase expression after human cardioembolic stroke: temporal profile and relation to neurological impairment. Stroke. Aug. 2001;32(8):1759-66.

Mun-Bryce, et al. Gelatinase B modulates selective opening of the blood-brain barrier during inflammation. Am J Physiol. May 1998;274(5 Pt 2):R1203-11.

Nitta, et al. Plasma concentration of brain natriuretic peptide as an indicator of cardiac ventricular function in patients on hemodialysis. Am J Nephrol. 1998;18(5):411-5.

Stronglin. Laboratory Diagnosis of Viral Infections, Sensitivity, specificity, and predictive value of diagnostic tests: Definitions and clinical applications. Leanette et al. eds. New York. Marcel Dekker, Inc. 1992; p. 211-219.

Sviri, et al. Brain natriuretic peptide and cerebral vasospasm in subarachnoid hemorrhage. Clinical and TCD correlations. Stroke. Jan. 2000;31(1):118-22.

Vander, et al. Human Physiology by McGraw Hill, Sixth Edition, 1994, pp. 214, 215, and 230.

Venugopal, et al. Cardiac natriuretic peptides—hope or hype? J Clin Pharm Ther. Feb. 2001;26(1):15-31.

Anderson, L. Candidate-Based Proteomics in the Search for Biomarkers of Cardiovascular Disease. J. Physiol. 563.1; 2004: 23-60.

Barber, et al. Hemostatic function and progressing ischemic stroke: D-dimer predicts early clinical progression. Stroke. Jun. 2004;35(6):1421-5. Epub Apr. 8, 2004.

Breyer, J. dissenting. Supreme Court of the United States, No. 04-607. Laboratory Coproration of America Holdings, DBA Labcorp, Petitioner v. Metabolite Laboratories, Inc., et al. Jun. 22, 2006 (slip opinion) pp. 1-15.

Clark, et al. Increased gelatinase A (MMP-2) and gelatinase B (MMP-9) activities in human brain after focal ischemia. Neurosci Lett. Nov. 28, 1997;238(1-2):53-6.

Coeroli et al. Nitric oxide production and perivascular tyrosine nitration following focal ischemia in neonatal rat. J Neurochem. Jun. 1998;70(6):2516-25.

Cossins, et al. Enhanced Expression of MMP-7 and MMP-9 in Demyelinating Multiple Sclerosis Lesions. Acta. Neuropathol. 1997;94:590-598.

Eikelboom, et al. C-reactive protein in ischemic stroke and its etiologic subtypes. J Stroke Cerebrovasc Dis. Mar.-Apr. 2003;12(2):74-81.

Fukui, et al. Focal Brain Edema and Natriuretic Peptides in Patients with Subarachnoid Hemorrhage. J. of Clin. Neuroscience. 2004;11(5): 507-511.

Gando, et al. Increased Neutrophil Elastase, Persistent Intravascular Coagulation, and Decreased Fibrinolytic Activity in Patients with Posttraumatic Acute Respiratory Distress Syndrome. J Trauma 1997;42:1068-1072.

Hatfield, et al. CSF Neuron-specific enolase as a quantitative marker of neuronal damage in a rat stroke model. Brain Res. Apr. 17, 1992;577(2):249-52. (abstract only).

International Search Report and the Written Opinion of the International Searching Authority dated Jul. 03, 2008 from PCT Application No. US05/38225.

Kemp, et al. Biochemical Markers of Myocardial Injury. Br. J. Anaesthesia 2004;93(1): 63-73.

Ma, et al. RAGE is expressed in pyramidal cells of the hippocampus following moderate hypoxic-ischemic brain injury in rats. Brain Res. Mar 21, 2003;966(2):167-74.

Maier, et al. Matrix Metalloproteinase-9 and Myeloperoxidase Expression: Quantitative Analysis by Antigen Immunohistochemistry in a Model of Transient Focal Cerbral Ischemia. Stroke. 2004;35:1169-1174.

McGirt, et al. Serum Von Willebrand Factor, Matrix Metalloproteinase-9 and Vascular Endothelial Growth Factor Levels Predict the Onset of Cerebral Vasospasm After Aneurysmal Subarachnoid Hemorrage. Neurosurgery. 2002;51(5):1128-1135.

Naghavi et al., From Vulnerable Plaque to Vulnerable Patient; A Call:for New Definitions and Risk Assessment Strategies: Part I, Circulation, Oct. 7,2003, pp. 1664-1672, vol. 108.

Office Action from Japanese Patent Office dated Jun. 10, 2008 for Japanese Application No. JP2003-521366 (in Japanese with English translation).

Orbe, et al. Independent association of matrix metalloproteinase-10, cardiovascular risk factors and subclinical atherosclerosis. Journal of Thrombosis and Haemostasis 2007;5 (1) , 91-97.

Shirasaki, et al. Serum S-100b protein as a biomarker for the assessment of neuroprotectants. Brain Res. Sep. 24, 2004;1021(2):159-66.

Stanek, et al. Prognostic Evaluation of Neurohumoral Plasma Levels Before and During Beta Blocker Therapy in Advanced Left Ventricular Dysfunction. JACC. 2002;38(2): 436-442.

Vasan, R. S. Biomarkers of cardiovascular disease: molecular basis and practical considerations. Circulation. May 16, 2006;113(19):2335-62.

Zhou, et al. HBO suppresses Nogo-A, Ng-R, or RhoA expression in the cerebral cortex after global ischemia. Biochem Biophys Res Commun. Sep. 19, 2003;309(2):368-76.

Frijns, et al. Soluble Adhesion Molecules Reflect Endothelial Cell Activation in lschemic Stroke and in Carotid Atherosclerosis. Stroke 1997;8:2214-2218.

\* cited by examiner

Fig. 1A: β-chimerin
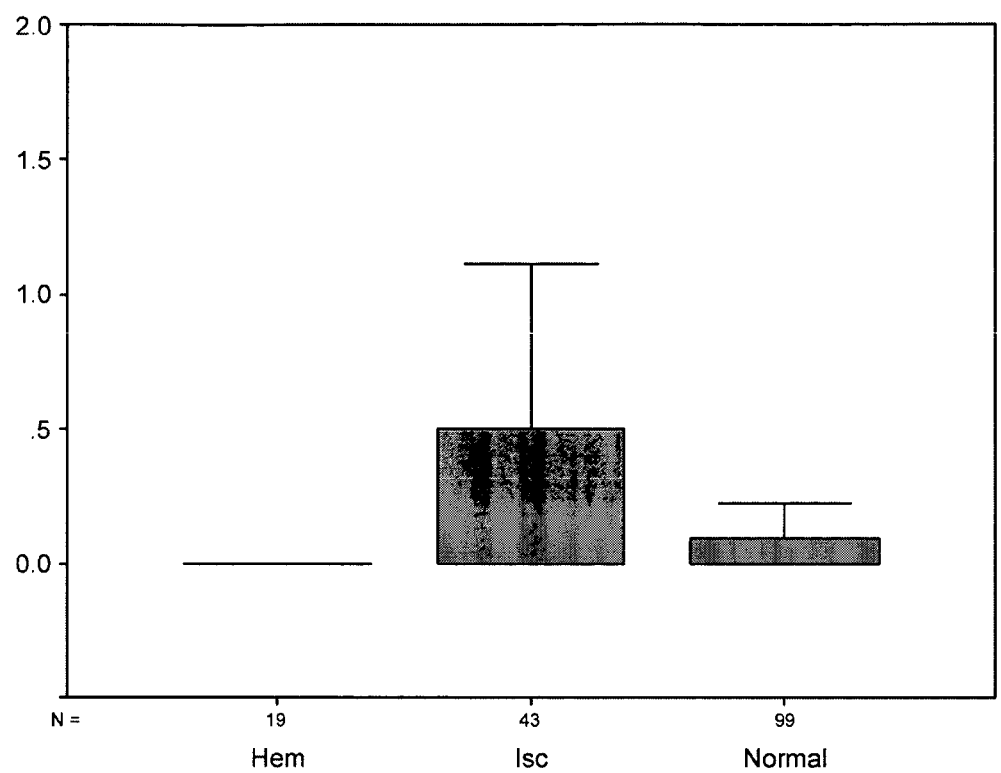

Fig. 1B: MPO
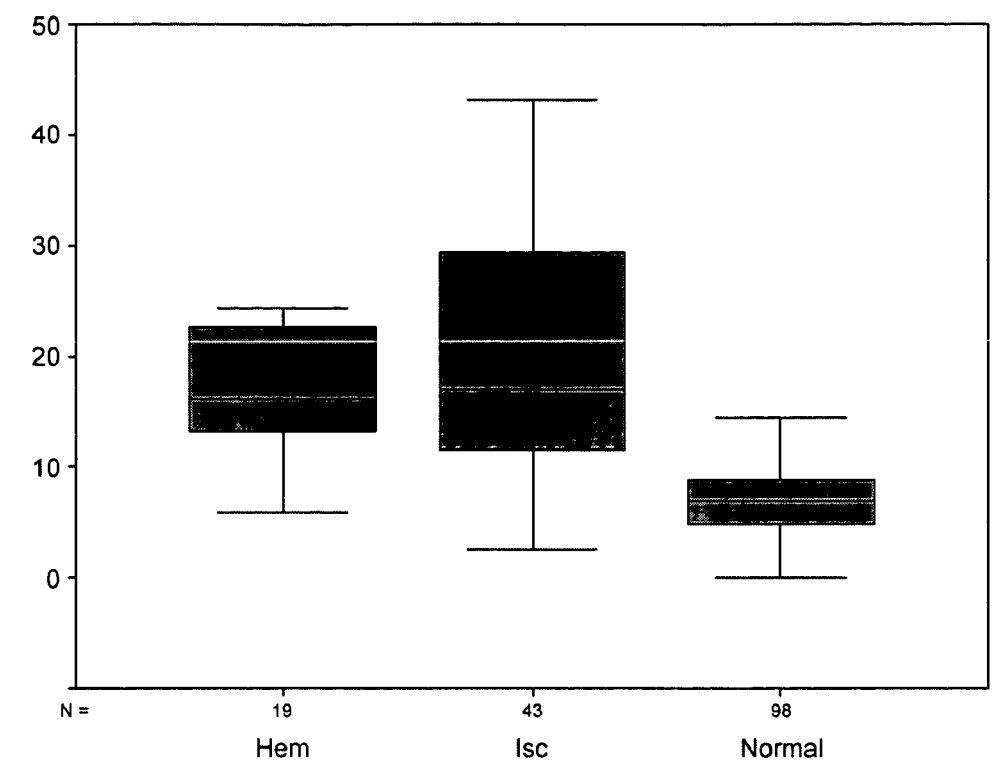

Fig. 1C: NDKA
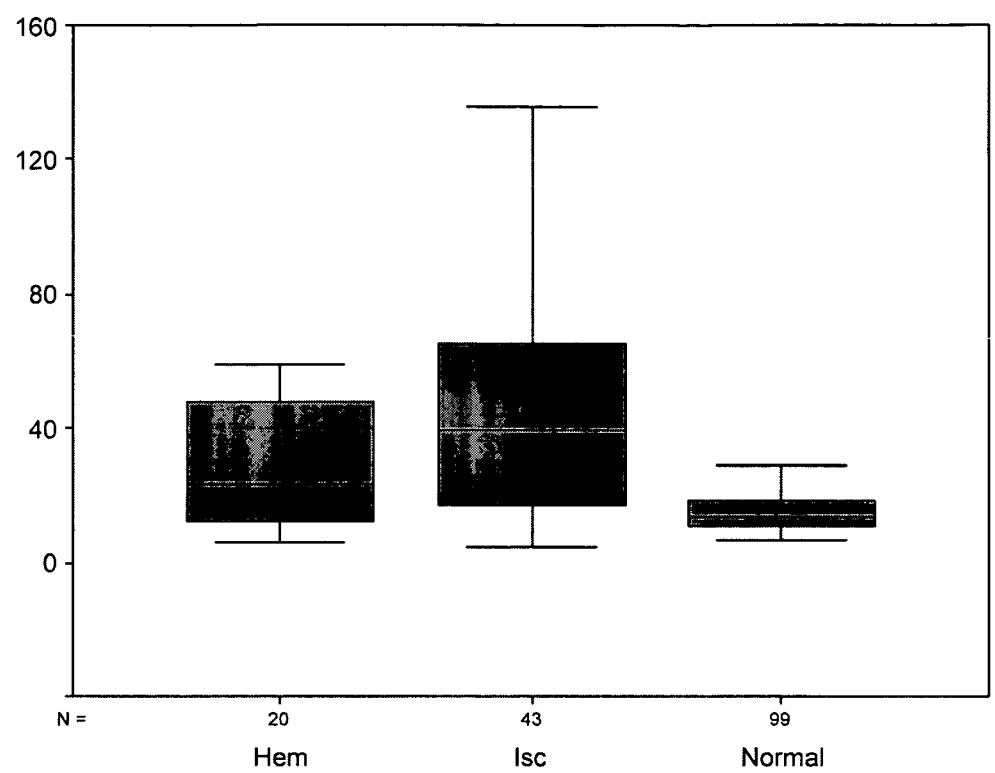

Fig. 1D: Nogo receptor
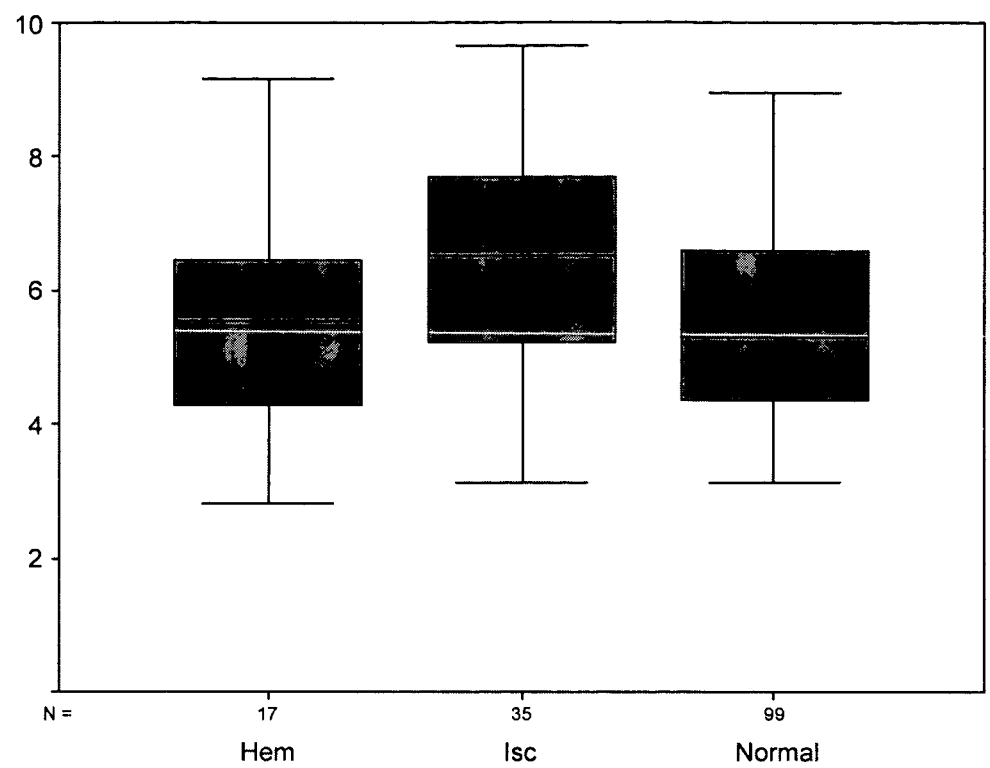

Fig. 1E: RAGE
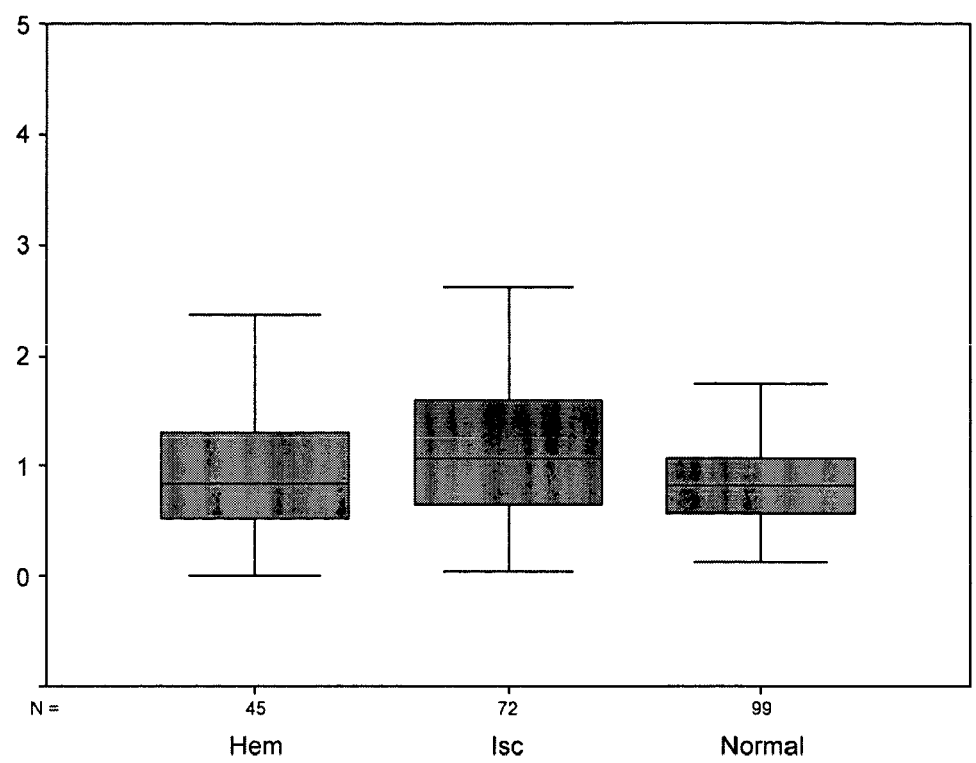

Fig. 1F: RNA-BP
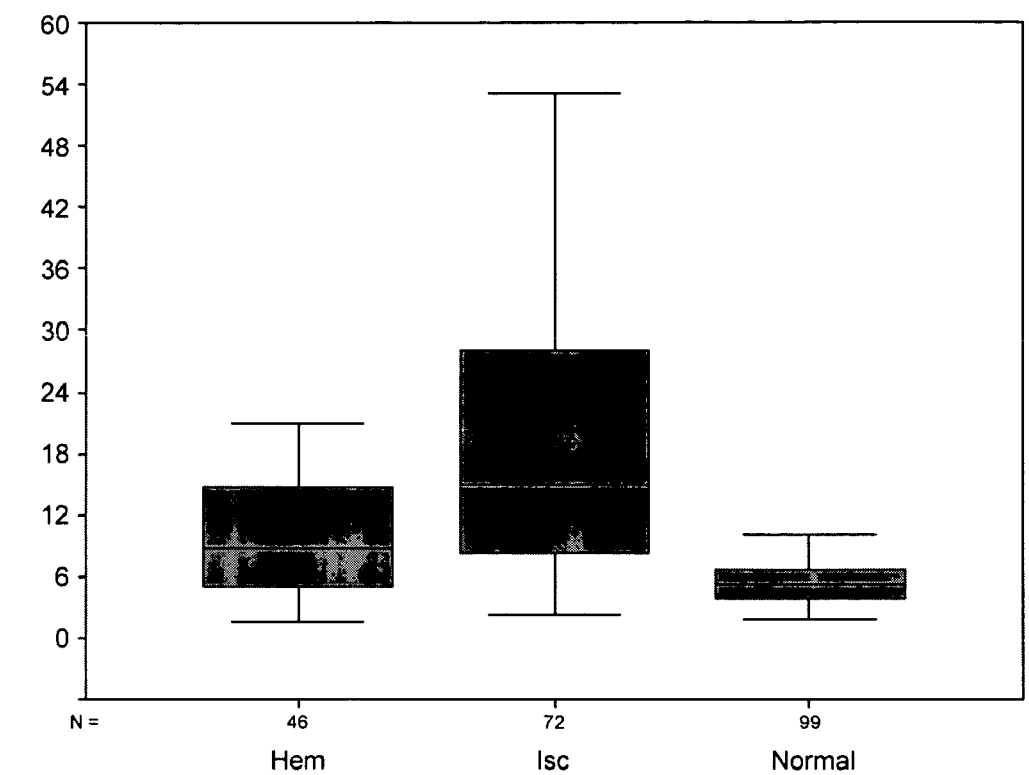

Fig. 1G: UFDP1H
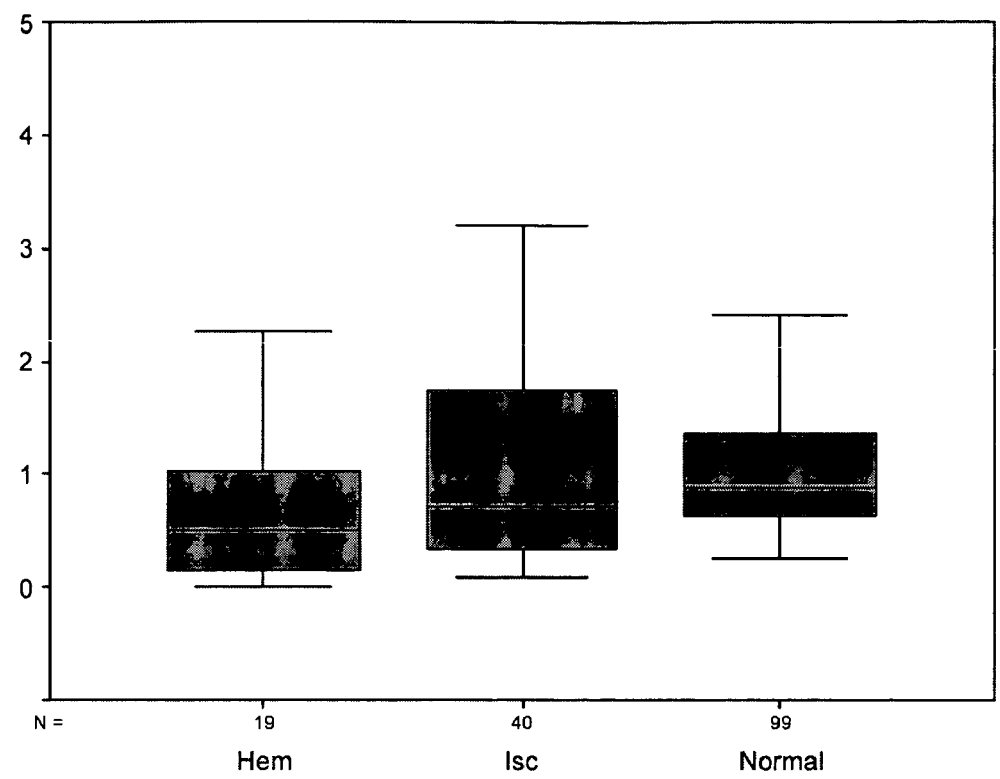

DIAGNOSTIC MARKERS OF STROKE AND CEREBRAL INJURY AND METHODS OF USE THEREOF

RELATED APPLICATIONS

This application is a continuation-in-part application of U.S. application Ser. No. 10/714,078, filed Nov. 14, 2003; which is a continuation-in-part application of U.S. application Ser. No. 10/673,077, filed Sep. 26, 2003; which is a continuation-in-part of U.S. application Ser. No. 10/371,149, filed Feb. 20, 2003; which is a continuation-in-part application of U.S. application Ser. No. 10/225,082, filed Aug. 20, 2002, and International Application No. PCT/US02/26604, filed Aug. 20, 2002; each of which claims the benefit of U.S. Provisional Application Nos. 60/313,775, filed Aug. 20, 2001, 60/334,964 filed Nov. 30, 2001, and 60/346,485, filed Jan. 2, 2002; the contents of each of which are hereby incorporated herein in their entirety, including all tables, figures, and claims.

FIELD OF THE INVENTION

The present invention relates to the identification and use of diagnostic markers for stroke and cerebral injury. In a various aspects, the invention relates to methods for the early detection and differentiation of stroke and transient ischemic attacks and the identification of individuals at risk for delayed neurological deficits upon presentation with stroke symptoms.

BACKGROUND OF THE INVENTION

The following discussion of the background of the invention is merely provided to aid the reader in understanding the invention and is not admitted to describe or constitute prior art to the present invention.

Stroke is a manifestation of vascular injury to the brain which is commonly secondary to atherosclerosis or hypertension, and is the third leading cause of death (and the second most common cause of neurologic disability) in the United States. Stroke can be categorized into two broad types, "ischemic stroke" and "hemorrhagic stroke." Additionally, a patient may experience transient ischemic attacks, which are in turn a high risk factor for the future development of a more severe episode.

Ischemic stroke encompasses thrombotic, embolic, lacunar and hypoperfusion types of strokes. Thrombi are occlusions of arteries created in situ within the brain, while emboli are occlusions caused by material from a distant source, such as the heart and major vessels, often dislodged due to myocardial infarct or atrial fibrillation. Less frequently, thrombi may also result from vascular inflammation due to disorders such as meningitis. Thrombi or emboli can result from atherosclerosis or other disorders, for example, arteritis, and lead to physical obstruction of arterial blood supply to the brain. Lacunar stroke refers to an infarct within non-cortical regions of the brain. Hypoperfusion embodies diffuse injury caused by non-localized cerebral ischemia, typically caused by myocardial infarction and arrhythmia.

The onset of ischemic stroke is often abrupt, and can become an "evolving stroke" manifested by neurologic deficits that worsen over a 24-48 hour period. In evolving stroke, "stroke-associated symptom(s)" commonly include unilateral neurologic dysfunction that extends progressively, without producing headache or fever. Evolving stroke may also become a "completed stroke," in which symptoms develop rapidly and are maximal within a few minutes.

Hemorrhagic stroke is caused by intracerebral or subarachnoid hemorrhage, i.e., bleeding into brain tissue, following blood vessel rupture within the brain. Intracerebral and subarachnoid hemorrhage are subsets of a broader category of hemorrhage referred to as intracranial hemorrhage. Intracerebral hemorrhage is typically due to chronic hypertension, and a resulting rupture of an arteriosclerotic vessel. Stroke-associated symptom(s) of intracerebral hemorrhage are abrupt, with the onset of headache and steadily increasing neurological deficits. Nausea, vomiting, delirium, seizures and loss of consciousness are additional common stroke-associated symptoms.

In contrast, most subarachnoid hemorrhage is caused by head trauma or aneurysm rupture which is accompanied by high pressure blood release which also causes direct cellular trauma. Prior to rupture, aneurysms may be asymptomatic, or occasionally associated with tension or migraine headaches. However, headache typically becomes acute and severe upon rupture, and may be accompanied by varying degrees of neurological deficit, vomiting, dizziness, and altered pulse and respiratory rates.

Transient ischemic attacks (TIAs) have a sudden onset and brief duration, typically 2-30 minutes. Most TIAs are due to emboli from atherosclerotic plaques, often originating in the arteries of the neck, and can result from brief interruptions of blood flow. The symptoms of TIAs are identical to those of stroke, but are only transient. Concomitant with underlying risk factors, patients experiencing TIAs are at a markedly increased risk for stroke.

The foregoing can be viewed as a manifestation of "brain ischemia." For example, the long-standing definition of TIAs has been based on the assumption that TIAs are associated with complete resolution of brain ischemia occurring rapidly enough to cause only transient symptoms. In contrast, ischemic stroke was thought to cause permanent injury to brain tissues. The similarity of these acute clinical syndromes made it difficult to differentiate them; they were distinguished on the basis of an arbitrary criterion for the duration of symptoms. But the development of symptoms of acute cerebral ischemia constitutes a medical emergency.

Concepts of brain ischemia and the temporal correlation with clinical events have changed considerably on the basis of studies using computed tomography (CT), magnetic resonance imaging (MRI), positron-emission tomography, and other imaging techniques. However, determining the immediate cause of verebral ischemia and differentiating ischemic from hemorrhagic stroke is difficult. CT scans can detect parenchymal bleeding greater than 1 cm and 95% of all subarachnoid hemorrhages. CT scan often cannot detect ischemic strokes until 6 hours from onset, depending on the infarct size. MRI may be more effective than CT scan in early detection of ischemic stroke, but it is less accurate at differentiating ischemic from hemorrhagic stroke, and is not widely available. An electrocardiogram (ECG) can be used in certain circumstances to identify a cardiac cause of stroke. Angiography is a definitive test to identify stenosis or occlusion of large and small cranial blood vessels, and can locate the cause of subarachnoid hemorrhages, define aneurysms, and detect cerebral vasospasm. It is, however, an invasive procedure that is also limited by cost and availability. Coagulation studies can also be used to rule out a coagulation disorder (coagulopathy) as a cause of hemorrhagic stroke.

Immediate diagnosis and care of a patient experiencing stroke can be critical. For example, tissue plasminogen activator (TPA) given within three hours of symptom onset in ischemic stroke is beneficial for selected acute stroke patients. Alternatively, patients may benefit from anticoagulants (e.g., heparin) if they are not candidates for TPA therapy. In contrast, thrombolytics and anticoagulants are strongly contraindicated in hemorrhagic strokes. Thus, early differentiation of ischemic events from hemorrhagic events is imperative. Moreover, delays in the confirmation of stroke diagnosis and the identification of stroke type limit the number of patients that may benefit from early intervention therapy. Finally, there are currently no diagnostic methods that can identify a TIA, or predict delayed neurological deficits which are often detected at a time after onset concurrent with the presentation of symptoms.

Accordingly, there is a present need in the art for a rapid, sensitive and specific diagnostic assay for stroke and TIA that can also differentiate the stroke type and identify those individuals at risk for delayed neurological deficits. Such a diagnostic assay would greatly increase the number of patients that can receive beneficial stroke treatment and therapy, and reduce the costs associated with incorrect stroke diagnosis.

BRIEF SUMMARY OF THE INVENTION

The present invention relates to the identification and use of diagnostic markers for stroke and neural tissue injury. The methods and compositions described herein can meet the need in the art for rapid, sensitive and specific diagnostic assay to be used in the diagnosis and differentiation of various forms of stroke and TIAs. Moreover, the methods and compositions of the present invention can also be used to facilitate the treatment of stroke patients and the development of additional diagnostic and/or prognostic indicators.

In various aspects, the invention relates to materials and procedures for identifying markers that are associated with the diagnosis, prognosis, or differentiation of cerebral ischemia in a patient; to using such markers in diagnosing and treating a patient and/or to monitor the course of a treatment regimen; to using such markers to identify subjects at risk for one or more adverse outcomes related to cerebral ischemia; and for screening compounds and pharmaceutical compositions that might provide a benefit in treating or preventing such conditions.

In a first aspect, the invention discloses methods for determining a diagnosis or prognosis related to cerebral ischemia, or for differentiating between types of strokes and/or other cerebral injuries such as TIA. These methods comprise analyzing a test sample obtained from a subject for the presence or amount of one or more markers as described hereinafter. These methods can comprise identifying one or more markers, the presence or amount of which is associated with the diagnosis, prognosis, or differentiation of cerebral ischemia. Once such marker(s) are identified, the level of such marker(s) in a sample obtained from a subject of interest can be measured. In certain embodiments, these markers can be compared to a level that is associated with the diagnosis, prognosis, or differentiation of cerebral ischemia. By correlating the subject's marker level(s) to the diagnostic marker level(s), the presence or absence of cerebral ischemia, the probability of future adverse outcomes, etc., in a patient may be rapidly and accurately determined.

In a related aspect, the invention discloses methods for determining the presence or absence of a disease in a subject that is exhibiting a perceptible change in one or more physical characteristics (that is, one or more "symptoms") that are indicative of a plurality of possible etiologies underlying the observed symptom(s), one of which is stroke. These methods comprise analyzing a test sample obtained from the subject for the presence or amount of one or more markers selected to rule in or out stroke, or one or more types of stroke, as a possible etiology of the observed symptom(s). Etiologies other than stroke that are within the differential diagnosis of the symptom(s) observed are referred to herein as "stroke mimics", and marker(s) able to differentiate one or more types of stroke from stroke mimics are referred to herein as "stroke differential diagnostic markers". The presence or amount of such marker(s) in a sample obtained from the subject can be used to rule in or rule out one or more of the following: stroke, thrombotic stroke, embolic stroke, lacunar stroke, hypoperfusion, intracerebral hemorrhage, and subarachnoid hemorrhage, thereby either providing a diagnosis (rule-in) and/or excluding a diagnosis (rule-out).

For purposes of the following discussion, the methods described as applicable to the diagnosis and prognosis of cerebral ischemia generally may be considered applicable to the diagnosis and prognosis of stroke and TIAs.

The term "marker" as used herein refers to proteins or polypeptides to be used as targets for screening test samples obtained from subjects. "Proteins or polypeptides" used as markers in the present invention are contemplated to include any fragments thereof, in particular, immunologically detectable fragments. One of skill in the art would recognize that proteins which are released by cells of the central nervous system which become damaged during a cerebral attack could become degraded or cleaved into such fragments. Additionally, certain markers are synthesized in an inactive form, which may be subsequently activated, e.g., by proteolysis. Examples of such markers are described hereinafter. The term "related marker" as used herein refers to one or more fragments of a particular marker that may be detected as a surrogate for the marker itself. These related markers may be, for example, "pre," "pro," or "prepro" forms of markers, or the "pre," "pro," or "prepro" fragment removed to form the mature marker. Exemplary markers that are synthesized as pre, pro, and prepro forms are described hereinafter. In preferred embodiments, these "pre," "pro," or "prepro" forms or the removed "pre," "pro," or "prepro" fragments are used in an equivalent fashion to the mature markers in the methods described herein.

The markers described herein may be used individually, or as part of panels as described hereinafter, and such panels may comprise 2, 3, 4, 5, 6, 7, 8, 9, 10, 15, 20, or more or individual markers. Preferred panels for the diagnosis and/or prognosis of cerebral ischemia comprise a plurality of markers independently selected from the group consisting of specific markers of neural tissue injury, markers related to blood pressure regulation, markers related to inflammation, markers related to coagulation and hemostasis, and markers related to apoptosis.

Particularly preferred markers for the diagnosis and/or prognosis of cerebral ischemia include caspase-3, cathepsin D, α-spectrin, nitrotyrosine, D-dimer, IL-1ra, NCAM, c-tau, neuropeptide Y, Tweak, c-Tau, IL-1ra, MCP-1, S100β, MMP-9, vWF, BNP, CRP, NT-3, VEGF, CKBB, MCP-1, Calbindin, thrombin-antithrombin III complex, IL-6, IL-8, myelin basic protein, tissue factor, GFAP, myeloperoxidase (MPO), NOGO receptor, RNA-binding protein regulatory subunit (RNA-BP; DJ-1), secretagogin, ubiquitin fusion degradation protein 1 homolog (UFDP1 H), receptor for advance glycation endproduct (RAGE), β-chimerin (chimerin II), neuron specific enolase, nucleoside diphosphate kinase A, and CNP, or markers related thereto. Each of these terms is defined hereinafter.

Certain preferred marker panels include at least one marker, and preferably 2, 3, 4, 5, or more markers, selected from the group consisting of myeloperoxidase, NOGO receptor, RNA-BP, UFDP1H, β-chimerin, and NDKA, or markers related thereto. In particularly preferred embodiments, one or more of these markers, and preferably 2, 3, 4, 5, or more markers, may be combined with one or more different markers and preferably 2, 3, 4, 5, 6, or more different markers, independently selected from the group consisting of specific markers of neural tissue injury, markers related to blood pressure regulation, markers related to inflammation, markers related to coagulation and hemostasis, and markers related to apoptosis. The different markers are preferably selected from the group consisting of BNP, caspase-3, CRP, D-dimer, MMP-9, S100β, neuropeptide Y, Secretagogin, CK-BB, and NSE, or markers related thereto.

In a panel, particular markers may be replaced with one or more markers related thereto, or with another marker from within a marker class (e.g., a marker related to blood pressure regulation such as BNP may be replaced by another marker related to blood pressure regulation; a marker related to inflammation such as CRP may be replaced by another marker related to inflammation; etc.). Also, one or more of these preferred markers may be deleted from a panel (e.g., a preferred panel may comprise CRP, VEGF, and BNP, as described hereinafter). Other exemplary panels are described below.

Other preferred markers of the invention can differentiate between ischemic stroke, hemorrhagic stroke, and TIA. Such markers are referred to herein as "stroke differentiating markers". Particularly preferred are markers that differentiate between thrombotic, embolic, lacunar, hypoperfusion, intracerebral hemorrhage, and subarachnoid hemorrhage types of strokes. Particularly preferred markers are those that distinguish ischemic stroke from hemorrhagic stroke.

Still other particularly preferred markers are those predictive of a subsequent cerebral vasospasm in patients presenting with subarachnoid hemorrhage, such as one or more markers related to blood pressure regulation, markers related to inflammation, markers related to apoptosis, and/or specific markers of neural tissue injury. Again, such panels may comprise 2, 3, 4, 5, 6, 7, 8, 9, 10, 15, 20, or more or individual markers.

Obtaining information on the true time of onset can be critical, as early treatments have been reported to be critical for proper treatment. Obtaining this time-of-onset information may be difficult, and is often based upon interviews with companions of the stroke victim. Thus, in various embodiments, markers and marker panels are selected to distinguish the approximate time since stroke onset. For purposes of the present invention, the term "acute stroke" refers to a stroke that has occurred within the prior 12 hours, more preferably within the prior 6 hours, and most preferably within the prior 3 hours; while the term "non-acute stroke" refers to a stroke that has occurred more than 12 hours ago, preferably between 12 and 48 hours ago, and most preferably between 12 and 24 hours ago. Preferred markers for differentiating between acute and non-acute strokes, referred to herein as stroke "time of onset markers" are described hereinafter.

A marker panel may be analyzed in a number of fashions well known to those of skill in the art. For example, each member of a panel may be compared to a "normal" value, or a value indicating a particular outcome. A particular diagnosis/prognosis may depend upon the comparison of each marker to this value; alternatively, if only a subset of markers are outside of a normal range, this subset may be indicative of a particular diagnosis/prognosis. The skilled artisan will also understand that diagnostic markers, differential diagnostic markers, prognostic markers, time of onset markers, stroke differentiating markers, etc., may be combined in a single assay or device. For example, certain markers in a panel may be commonly used to diagnose the existence of a stroke, while other members of the panel may indicate if an acute stroke has occurred, while still other members of the panel may indicate if a non-acute stroke has occurred. Markers may also be commonly used for multiple purposes by, for example, applying a different threshold or a different weighting factor to the marker for the different purpose(s). For example, a marker at one concentration or weighting may be used, alone or as part of a larger panel, to indicate if an acute stroke has occurred, and the same marker at a different concentration or weighting may be used, alone or as part of a larger panel, to indicate if a non-acute stroke has occurred.

Preferred panels comprise markers for the following purposes: diagnosis of cerebral ischemia, diagnosis of stroke; diagnosis of stroke and indication if an acute stroke has occurred; diagnosis of stroke and indication if an non-acute stroke has occurred; diagnosis of stroke, indication if an acute stroke has occurred, and indication if an non-acute stroke has occurred; diagnosis of stroke and indication if an ischemic stroke has occurred; diagnosis of stroke and indication if a hemorrhagic stroke has occurred; diagnosis of stroke, indication if an ischemic stroke has occurred, and indication if a hemorrhagic stroke has occurred; diagnosis of cerebral ischemia and prognosis of a subsequent adverse outcome; diagnosis of stroke and prognosis of a subsequent adverse outcome; diagnosis of stroke and prognosis of a subsequent cerebral vasospasm; and diagnosis of stroke, indication if a hemorrhagic stroke has occurred, and prognosis of a subsequent cerebral vasospasm.

As noted above, panels may also comprise differential diagnosis of cerebral ischemia, differential diagnosis of stroke; differential diagnosis of stroke and indication if an acute stroke has occurred; differential diagnosis of stroke and indication if an non-acute stroke has occurred; differential diagnosis of stroke, indication if an acute stroke has occurred, and indication if an non-acute stroke has occurred; differential diagnosis of stroke and indication if an ischemic stroke has occurred; differential diagnosis of stroke and indication if a hemorrhagic stroke has occurred; differential diagnosis of stroke, indication if an ischemic stroke has occurred, and indication if a hemorrhagic stroke has occurred; differential diagnosis of cerebral ischemia and prognosis of a subsequent adverse outcome; differential diagnosis of stroke and prognosis of a subsequent adverse outcome; differential diagnosis of stroke and prognosis of a subsequent cerebral vasospasm; differential diagnosis of stroke, indication if a hemorrhagic stroke has occurred, and prognosis of a subsequent cerebral vasospasm.

In certain embodiments, one or more diagnostic or prognostic indicators are correlated to a condition or disease by merely the presence or absence of the indicator(s). In other embodiments, threshold level(s) of a diagnostic or prognostic indicator(s) can be established, and the level of the indicator(s) in a patient sample can simply be compared to the threshold level(s). The sensitivity and specificity of a diagnostic and/or prognostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in "normal" and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create an ROC curve. For example, results of a test on "disease" samples might be ranked according to degree (say 1=low, 2=normal, and 3=high). This ranking can be correlated to results in the "normal" population, and a ROC curve created. These methods are well known in the art. See, e.g., Hanley et al., *Radiology* 143: 29-36 (1982).

One or more markers may lack diagnostic or prognostic value when considered alone, but when used as part of a panel, such markers may be of great value in determining a particular diagnosis/prognosis. In preferred embodiments, particular thresholds for one or more markers in a panel are not relied upon to determine if a profile of marker levels obtained from a subject are indicative of a particular diagnosis/prognosis. Rather, the present invention may utilize an evaluation of the entire marker profile by plotting ROC curves for the sensitivity of a particular panel of markers versus 1-(specificity) for the panel at various cutoffs. In these methods, a profile of marker measurements from a subject is considered together to provide a global probability (expressed either as a numeric score or as a percentage risk) that an individual has had a stroke, is at risk for a stroke, the type of stroke (ischemic or hemorrhagic) which the individual has had or is at risk for, has had a TIA and not a stroke, etc. In such embodiments, an increase in a certain subset of markers may be sufficient to indicate a particular diagnosis/prognosis in one patient, while an increase in a different subset of markers may be sufficient to indicate the same or a different diagnosis/prognosis in another patient. Weighting factors may also be applied to one or more markers in a panel, for example, when a marker is of particularly high utility in identifying a particular diagnosis/prognosis, it may be weighted so that at a given level it alone is sufficient to signal a positive result. Likewise, a weighting factor may provide that no given level of a particular marker is sufficient to signal a positive result, but only signals a result when another marker also contributes to the analysis.

In preferred embodiments, markers and/or marker panels are selected to exhibit at least 70% sensitivity, more preferably at least 80% sensitivity, even more preferably at least 85% sensitivity, still more preferably at least 90% sensitivity, and most preferably at least 95% sensitivity, combined with at least 70% specificity, more preferably at least 80% specificity, even more preferably at least 85% specificity, still more preferably at least 90% specificity, and most preferably at least 95% specificity. In particularly preferred embodiments, both the sensitivity and specificity are at least 75%, more preferably at least 80%, even more preferably at least 85%, still more preferably at least 90%, and most preferably at least 95%.

The term "test sample" as used herein refers to a sample of bodily fluid obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine and saliva. In addition, one of skill in the art would realize that some test samples would be more readily analyzed following a fractionation or purification procedure, for example, separation of whole blood into serum or plasma components.

The term "specific marker of neural tissue injury" as used herein refers to proteins or polypeptides that are associated with brain tissue and neural cells, and which can be correlated with a neural tissue injury, but are not correlated with other types of injury. Such specific markers of neural tissue injury include adenylate kinase, brain-derived neurotrophic factor, calbindin-D, NOGO receptor, creatine kinase-BB, glial fibrillary acidic protein, lactate dehydrogenase, RNA binding protein regulatory subunit (also known as RAGE and DJ-1), myelin basic protein, neural cell adhesion molecule, c-tau, neuropeptide Y, neuron-specific enolase, neurotrophin-3, β-chimerin, proteolipid protein, S-100β, thrombomodulin, protein kinase C gamma, and the like. These specific markers are described in detail hereinafter.

Preferred marker(s) related to blood pressure regulation for use in the methods described herein comprise, for example, one or more marker(s) selected from the group consisting of atrial natriuretic peptide ("ANP"), pro-ANP, B-type natriuretic peptide ("BNP"), NT-pro BNP, pro-BNP C-type natriuretic peptide, urotensin II, arginine vasopressin, aldosterone, angiotensin I, angiotensin II, angiotensin III, bradykinin, calcitonin, procalcitonin, calcitonin gene related peptide, adrenomedullin, calcyphosine, endothelin-2, endothelin-3, renin, and urodilatin, or markers related thereto.

Preferred marker(s) markers related to inflammation for use in the methods described herein comprise, for example, one or more marker(s) selected from the group consisting of acute phase reactants, cell adhesion molecules such as vascular cell adhesion molecule ("VCAM"), intercellular adhesion molecule-1 ("ICAM-1"), intercellular adhesion molecule-2 ("ICAM-2"), and intercellular adhesion molecule-3 ("ICAM-3"), myeloperoxidase (MPO), C-reactive protein, interleukins such as IL-1β, IL-6, and IL-8, interleukin-1 receptor agonist, monocyte chemoattractant protein-1, myeloperoxidase, lipocalin-type prostaglandin D synthase, mast cell tryptase, eosinophil cationic protein, haptoglobin, tumor necrosis factor α, tumor necrosis factor β, Fas ligand, soluble Fas (Apo-1), TRAIL, TWEAK, RAGE, fibronectin, macrophage migration inhibitory factor (MIF), nitrotyrosine, and vascular endothelial growth factor ("VEGF"), or markers related thereto.

The term "acute phase reactants" as used herein refers to proteins whose concentrations are elevated in response to stressful or inflammatory states that occur during various insults that include infection, injury, surgery, trauma, tissue necrosis, and the like. Acute phase reactant expression and serum concentration elevations are not specific for the type of insult, but rather as a part of the homeostatic response to the insult. In addition to those acute phase reactants listed above as "markers related to inflammation," one or more markers related to inflammation may also be selected from the group of acute phase reactants consisting of hepcidin, HSP-60, HSP-65, HSP-70, asymmetric dimethylarginine (an endogenous inhibitor of nitric oxide synthase), matrix metalloproteins 11, 3, and 9, defensin HBD 1, defensin HBD 2, serum amyloid A, oxidized LDL, insulin like growth factor, transforming growth factor β, e-selectin, glutathione-S-transferase, hypoxia-inducible factor-1α, inducible nitric oxide synthase ("I-NOS"), intracellular adhesion molecule, lactate dehydrogenase, monocyte chemoattractant peptide-1 ("MCP-1"), n-acetyl aspartate, prostaglandin E2, receptor activator of nuclear factor ("RANK") ligand, TNF receptor superfamily member 1A, lipopolysaccharide binding protein ("LBP"), and cystatin C, or markers related thereto.

Preferred marker(s) related to coagulation and hemostasis for use in the methods described herein comprise, for example, one or more marker(s) selected from the group consisting of plasmin, fibrinogen, thrombus precursor protein, D-dimer, β-thromboglobulin, platelet factor 4, fibrinopeptide A, platelet-derived growth factor, prothrombin fragment 1+2, plasmin-α2-antiplasmin complex, thrombin-antithrombin III complex, P-selectin, thrombin, and von Willebrand factor, tissue factor, or markers related thereto.

Preferred marker(s) related to apoptosis for use in the methods described herein comprise, for example, one or more marker(s) selected from the group consisting of spectrin, cathepsin D, caspase 3, cytochrome c, s-acetyl glutathione, NDKA, and ubiquitin fusion degradation protein 1 homolog.

The phrase "diagnosis" as used herein refers to methods by which the skilled artisan can estimate and/or determine whether or not a patient is suffering from a given disease or condition. The skilled artisan often makes a diagnosis on the basis of one or more diagnostic indicators, i.e., a marker, the presence, absence, or amount of which is indicative of the presence, severity, or absence of the condition.

Similarly, a prognosis is often determined by examining one or more "prognostic indicators." These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for experiencing a future stroke in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient. Preferred prognostic markers can predict the onset of delayed neurologic deficits in a patient after stroke, or the chance of future stroke.

The term "correlating," as used herein in reference to the use of diagnostic and prognostic indicators, refers to relating one or more marker levels to the presence (or absence) of a particular disease or prognosis. In certain embodiments, correlating comprises comparing the presence or amount of the indicator in a patient to its presence or amount in persons known to suffer from, or known to be at risk of, a given condition; or in persons known to be free of a given condition. As discussed above, a marker level in a patient sample can be compared to a level known to be associated with a specific type of stroke. The sample's marker level is said to have been correlated with a diagnosis; that is, the skilled artisan can use the marker level to determine whether the patient suffers from a specific type of stroke, and respond accordingly. Alternatively, the sample's marker level can be compared to a marker level known to be associated with a good outcome (e.g., the absence of stroke, etc.). In preferred embodiments, a profile of marker levels are correlated to a global probability or a particular outcome using ROC curves.

While exemplary panels are described herein, one or more markers may be replaced, added, or subtracted from these exemplary panels wile still providing clinically useful results. Panels may comprise both specific markers of a disease and/ or non-specific markers. A particular "fingerprint" pattern of changes in such a panel of markers may, in effect, act as a specific indicator of disease. As discussed above, that pattern of changes may be obtained from a single sample, or from temporal changes in one or more members of the panel (or a panel response value).

In yet other embodiments, multiple determinations of one or more diagnostic or prognostic markers can be made, and a temporal change in the marker can be used to determine a diagnosis or prognosis. For example, a diagnostic indicator may be determined at an initial time, and again at a second time. In such embodiments, an increase in the marker from the initial time to the second time may be diagnostic of a particular type of stroke, or a given prognosis. Likewise, a decrease in the marker from the initial time to the second time may be indicative of a particular type of stroke, or a given prognosis. This "temporal change" parameter can be included as a marker in a marker panel.

In yet another embodiment, multiple determinations of one or more diagnostic or prognostic markers can be made, and a temporal change in the marker can be used to monitor the efficacy of neuroprotective, thrombolytic, or other appropriate therapies. In such an embodiment, one might expect to see a decrease or an increase in the marker(s) over time during the course of effective therapy.

The skilled artisan will understand that, while in certain embodiments comparative measurements are made of the same diagnostic marker at multiple time points, one could also measure a given marker at one time point, and a second marker at a second time point, and a comparison of these markers may provide diagnostic information. Similarly, the skilled artisan will understand that serial measurements and changes in markers or the combined result over time may also be of diagnostic and/or prognostic value.

The phrase "determining the prognosis" as used herein refers to methods by which the skilled artisan can predict the course or outcome of a condition in a patient. The term "prognosis" does not refer to the ability to predict the course or outcome of a condition with 100% accuracy, or even that a given course or outcome is more likely to occur than not. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. For example, in individuals not exhibiting the condition, the chance of a given outcome may be about 3%. In preferred embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, and about a 95% chance. The term "about" in this context refers to ±1%.

The skilled artisan will understand that associating a prognostic indicator with a predisposition to an adverse outcome is a statistical analysis. For example, a marker level of greater than 80 pg/mL may signal that a patient is more likely to suffer from an adverse outcome than patients with a level less than or equal to 80 pg/mL, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001. Exemplary statistical tests for associating a prognostic indicator with a predisposition to an adverse outcome are described hereinafter.

In other embodiments, a threshold degree of change in the level of a prognostic or diagnostic indicator can be established, and the degree of change in the level of the indicator in a patient sample can simply be compared to the threshold degree of change in the level. A preferred threshold change in the level for markers of the invention is about 5%, about 10%, about 15%, about 20%, about 25%, about 30%, about 50%, about 75%, about 100%, and about 150%. The term "about" in this context refers to ±10%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In yet another aspect, the invention relates to methods for determining a treatment regimen for use in a patient diagnosed with stroke. The methods preferably comprise determining a level of one or more diagnostic or prognostic markers as described herein, and using the markers to determine a diagnosis for a patient. For example, a prognosis might include the development or predisposition to delayed neurologic deficits after stroke onset. One or more treatment regimens that improve the patient's prognosis by reducing the increased disposition for an adverse outcome associated with the diagnosis can then be used to treat the patient. Such methods may also be used to screen pharmacological compounds for agents capable of improving the patient's prognosis as above.

In another aspect, the invention relates to methods of identifying a patient at risk for cerebral vasospasm. Such methods preferably comprise comparing an amount of one or more marker(s) predictive of a subsequent cerebral vasospasm in a test sample from a patient diagnosed with a subarachnoid hemorrhage. Such markers may be one or more markers related to blood pressure regulation, markers related to inflammation, markers related to apoptosis, and/or specific markers of neural tissue injury. As discussed herein, such marker may be used in panels comprising 2, 3, 4, 5, 6, 7, 8, 9, 10, 15, 20, or more or individual markers. Preferred marker(s) may be selected from the group consisting of IL-1ra, C-reactive protein, von Willebrand factor (vWF), vascular endothelial growth factor (VEGF), matrix metalloprotease-9 (MMP-9), neural cell adhesion molecule (NCAM), BNP, and caspase-3, or markers related thereto. The levels of one or more markers may be compared to a predictive level of said marker(s), wherein said patient is identified as being at risk for cerebral vasospasm by a level of said marker(s) equal to or greater than said predictive level. In the alternative, a panel response value for a plurality of such markers may be determined, optionally considering a change in the level of one or more such markers as an additional independent marker.

In yet another aspect, the invention relates to methods of differentiating ischemic stroke from hemorrhagic stroke using such marker panels.

In a further aspect, the invention relates to kits for determining the diagnosis or prognosis of a patient. These kits preferably comprise devices and reagents for measuring one or more marker levels in a patient sample, and instructions for performing the assay. Optionally, the kits may contain one or more means for converting marker level(s) to a prognosis. Such kits preferably contain sufficient reagents to perform one or more such determinations, and/or Food and Drug Administration (FDA)-approved labeling.

BRIEF DESCRIPTION OF THE FIGURES

FIGS. 1A-G show box and whisker plots representing measured concentrations of .beta.-chimerin, myeloperoxidase, NDKA, Nogo receptor, RAGE, RNA-BP, and UFDP1H, respectively. The "box" portion of each plot represents the values between the 25th percentile and the 75th percentile of measured concentrations; a line within the box represents the median; bars below and above the box represent the smallest and largest measured concentrations that are not "outliers" (values more than 1.5 box lengths from the 25th percentile and the 75th percentile). Each plot shows values for ischemic stroke, hemorrhagic stroke, and age-matched normal cohorts.

DETAILED DESCRIPTION OF THE INVENTION

In accordance with the present invention, there are provided methods and compositions for the identification and use of markers that are associated with the diagnosis, prognosis, or differentiation of cerebral ischemia in a subject. Such markers can be used in diagnosing and treating a subject and/or to monitor the course of a treatment regimen; for screening subjects for the occurrence or risk of a particular disease; and for screening compounds and pharmaceutical compositions that might provide a benefit in treating or preventing such conditions.

Stroke is a pathological condition with acute onset that is caused by the occlusion or rupture of a vessel supplying blood, and thus oxygen and nutrients, to the brain. The immediate area of injury is referred to as the "core," which contains brain cells that have died as a result of ischemia or physical damage. The "penumbra" is composed of brain cells that are neurologically or chemically connected to cells in the core. Cells within the penumbra are injured, but still have the ability to completely recover following removal of the insult caused during stroke. However, as ischemia or bleeding from hemorrhage continues, the core of dead cells can expand from the site of insult, resulting in a concurrent expansion of cells in the penumbra. The initial volume and rate of core expansion is related to the severity of the stroke and, in most cases, neurological outcome.

The brain contains two major types of cells, neurons and glial cells. Neurons are the most important cells in the brain, and are responsible for maintaining communication within the brain via electrical and chemical signaling. Glial cells function mainly as structural components of the brain, and they are approximately 10 times more abundant than neurons. Glial cells of the central nervous system (CNS) are astrocytes and oligodendrocytes. Astrocytes are the major interstitial cells of the brain, and they extend cellular processes that are intertwined with and surround neurons, isolating them from other neurons. Astrocytes can also form "end feet" at the end of their processes that surround capillaries. Oligodendrocytes are cells that form myelin sheathes around axons in the CNS. Each oligodendrocyte has the ability to ensheathe up to 50 axons. Schwann cells are glial cells of the peripheral nervous system (PNS). Schwann cells form myelin sheathes around axons in the periphery, and each Schwann cell ensheathes a single axon.

Cell death during stroke occurs as a result of ischemia or physical damage to the cells of the CNS. During ischemic stroke, an infarct occurs, greatly reducing or stopping blood flow beyond the site of infarction. The zone immediately beyond the infarct soon lacks suitable blood concentrations of the nutrients essential for cell survival. Cells that lack nutrients essential for the maintenance of important functions like metabolism soon perish. Hemorrhagic stroke can induce cell death by direct trauma, elevation in intracranial pressure, and the release of damaging biochemical substances in blood. When cells die, they release their cytosolic contents into the extracellular milieu.

The barrier action of tight junctions between the capillary endothelial cells of the central nervous system is referred to as the "blood-brain barrier". This barrier is normally impermeable to proteins and other molecules, both large and small. In other tissues such as skeletal, cardiac, and smooth muscle, the junctions between endothelial cells are loose enough to allow passage of most molecules, but not proteins.

Substances that are secreted by the neurons and glial cells (intracellular brain compartment) of the central nervous system (CNS) can freely pass into the extracellular milieu (extracellular brain compartment). Likewise, substances from the extracellular brain compartment can pass into the intracellular brain compartment. The passage of substances between the intracellular and extracellular brain compartments are restricted by the normal cellular mechanisms that regulate substance entry and exit. Substances that are found in the extracellular brain compartment also are able to pass freely into the cerebrospinal fluid, and vice versa. This movement is controlled by diffusion.

The movement of substances between the vasculature and the CNS is restricted by the blood-brain barrier. This restriction can be circumvented by facilitated transport mechanisms in the endothelial cells that transport, among other substances, nutrients like glucose and amino acids across the barrier for consumption by the cells of the CNS. Furthermore, lipid-soluble substances such as molecular oxygen and carbon dioxide, as well as any lipid-soluble drugs or narcotics can freely diffuse across the blood-brain barrier.

Depending upon their size, specific markers of neural tissue injury that are released from injured brain cells during stroke or other neuropathies will only be found in peripheral blood when CNS injury is coupled with or followed by an increase in the permeability of the blood-brain barrier. This is particularly true of larger molecules. Smaller molecules may appear in the peripheral blood as a result of passive diffusion, active transport, or an increase in the permeability of the blood-brain barrier. Increases in blood-brain barrier permeability can arise as a result of physical disruption in cases such as tumor invasion and extravasation or vascular rupture, or as a result of endothelial cell death due to ischemia. During stroke, the blood-brain barrier is compromised by endothelial cell death, and any cytosolic components of dead cells that are present within the local extracellular milieu can enter the bloodstream.

Therefore, specific markers of neural tissue injury may also be found in the blood or in blood components such as serum and plasma, as well as the CSF of a patient experiencing stroke or TIAs. Furthermore, clearance of the obstructing object in ischemic stroke can cause injury from oxidative insult during reperfusion, and patients with ischemic stroke can sometimes experience hemorrhagic transformation as a result of reperfusion or thrombolytic therapy. Additionally, injury can be caused by vasospasm, which is a focal or diffuse narrowing of the large capacity arteries at the base of the brain following hemorrhage. The increase in blood-brain barrier permeability is related to the insult severity, and its integrity is reestablished following the resolution of insult. Specific markers of neural tissue injury will only be present in peripheral blood if there has been a sufficient increase in the permeability of the blood-brain barrier that allows these large molecules to diffuse across. In this regard, most specific markers of neural tissue injury can be found in cerebrospinal fluid after stroke or any other neuropathy that affects the CNS. Furthermore, many investigations of coagulation or fibrinolysis markers in stroke are performed using cerebrospinal fluid.

The Coagulation Cascade in Cerebral Ischemia

There are essentially two mechanisms that are used to halt or prevent blood loss following vessel injury. The first mechanism involves the activation of platelets to facilitate adherence to the site of vessel injury. The activated platelets then aggregate to form a platelet plug that reduces or temporarily stops blood loss. The processes of platelet aggregation, plug formation and tissue repair are all accelerated and enhanced by numerous factors secreted by activated platelets. Platelet aggregation and plug formation is mediated by the formation of a fibrinogen bridge between activated platelets. Concurrent activation of the second mechanism, the coagulation cascade, results in the generation of fibrin from fibrinogen and the formation of an insoluble fibrin clot that strengthens the platelet plug.

The coagulation cascade is an enzymatic pathway that involves numerous serine proteinases normally present in an inactive, or zymogen, form. The presence of a foreign surface in the vasculature or vascular injury results in the activation of the intrinsic and extrinsic coagulation pathways, respectively. A final common pathway is then followed, which results in the generation of fibrin by the serine proteinase thrombin and, ultimately, a crosslinked fibrin clot. In the coagulation cascade, one active enzyme is formed initially, which can activate other enzymes that active others, and this process, if left unregulated, can continue until all coagulation enzymes are activated. Fortunately, there are mechanisms in place, including fibrinolysis and the action of endogenous proteinase inhibitors that can regulate the activity of the coagulation pathway and clot formation.

Fibrinolysis is the process of proteolytic clot dissolution. In a manner analogous to coagulation, fibrinolysis is mediated by serine proteinases that are activated from their zymogen form. The serine proteinase plasmin is responsible for the degradation of fibrin into smaller degradation products that are liberated from the clot, resulting in clot dissolution. Fibrinolysis is activated soon after coagulation in order to regulate clot formation. Endogenous serine proteinase inhibitors also function as regulators of fibrinolysis.

The presence of a coagulation or fibrinolysis marker in cerebrospinal fluid would indicate that activation of coagulation or fibrinolysis, depending upon the marker used, coupled with increased permeability of the blood-brain barrier has occurred. In this regard, more definitive conclusions regarding the presence of coagulation or fibrinolysis markers associated with acute stroke may be obtained using cerebrospinal fluid.

Platelets are round or oval disks with an average diameter of 2-4 µm that are normally found in blood at a concentration of 200,000-300,000/µl. They play an essential role in maintaining hemostasis by maintaining vascular integrity, initially stopping bleeding by forming a platelet plug at the site of vascular injury, and by contributing to the process of fibrin formation to stabilize the platelet plug. When vascular injury occurs, platelets adhere to the site of injury and each other and are stimulated to aggregate by various agents released from adherent platelets and injured endothelial cells. This is followed by the release reaction, in which platelets secrete the contents of their intracellular granules, and formation of the platelet plug. The formation of fibrin by thrombin in the coagulation cascade allows for consolidation of the plug, followed by clot retraction and stabilization of the plug by crosslinked fibrin. Active thrombin, generated in the concurrent coagulation cascade, also has the ability to induce platelet activation and aggregation.

The coagulation cascade can be activated through either the extrinsic or intrinsic pathways. These enzymatic pathways share one final common pathway. The result of coagulation activation is the formation of a crosslinked fibrin clot. Fibrinolysis is the process of proteolytic clot dissolution that is activated soon after coagulation activation, perhaps in an effort to control the rate and amount of clot formation. Urokinase-type plasminogen activator (uPA) and tissue-type plasminogen activator (tPA) proteolytically cleave plasminogen, generating the active serine proteinase plasmin. Plasmin proteolytically digests crosslinked fibrin, resulting in clot dissolution and the production and release of fibrin degradation products.

The first step of the common pathway of the coagulation cascade involves the proteolytic cleavage of prothrombin by the factor Xa/factor Va prothrombinase complex to yield active thrombin. Thrombin is a serine proteinase that proteolytically cleaves fibrinogen to form fibrin, which is ultimately integrated into a crosslinked network during clot formation.

Exemplary Markers

The term "related marker" as used herein refers to one or more fragments of a particular marker or its biosynthetic parent that may be detected as a surrogate for the marker itself or as independent markers. For example, human BNP is derived by proteolysis of a 108 amino acid precursor molecule, referred to hereinafter as $BNP_{1-108}$. Mature BNP, or "the BNP natriuretic peptide," or "BNP-32" is a 32 amino acid molecule representing amino acids 77-108 of this precursor, which may be referred to as $BNP_{77-108}$. The remaining residues 1-76 are referred to hereinafter as $BNP_{1-76}$.

The sequence of the 108 amino acid human BNP precursor pro-BNP ($BNP_{1-108}$) is as follows, with mature BNP ($BNP_{77-108}$) underlined:

```
                                                        (SEQ ID NO: 1)
HPLGSPGSAS DLETSGLQEQ RNHLQGKLSE LQVEQTSLEP LQESPRPTGV        50

WKSREVATEG IRGHRKMVLY TLRAPRSPKM VQGSGCFGRK MDRISSSSGL       100

GCKVLRRH.                                                   108
```

$BNP_{1-108}$ is synthesized as a larger precursor pre-pro-BNP having the following sequence (with the "pre" sequence shown in bold):

```
                                                        (SEQ ID NO: 2)
MDPQTAPSPA LLLLLFLHLA FLGGRSHPLG SPGSASDLET SGLQEQRNHL        50

QGKLSELQVE QTSLEPLQES PRPTGVWKSR EVATEGIRGH RKMVLYTLRA       100

PRSPKMVQGS GCFGRKMDRT SSSSGLGCKV LRRH.                      134
```

While mature BNP itself may be used as a marker in the present invention, the prepro-BNP, $BNP_{1-108}$ and $BNP_{1-76}$ molecules represent BNP-related markers that may be measured either as surrogates for mature BNP or as markers in and of themselves. In addition, one or more fragments of these molecules, including BNP-related polypeptides selected from the group consisting of $BNP_{77-106}$, $BNP_{79-106}$, $BNP_{76-107}$, $BNP_{69-108}$, $BNP_{79-108}$, $BNP_{80-108}$, $BNP_{81-108}$, $BNP_{83-108}$, $BNP_{39-86}$, $BNP_{53-85}$, $BNP_{66-98}$, $BNP_{30-103}$, $BNP_{11-107}$, $BNP_{9-106}$, and $BNP_{3-108}$ may also be present in circulation. In addition, natriuretic peptide fragments, including BNP fragments, may comprise one or more oxidizable methionines, the oxidation of which to methionine sulfoxide or methionine sulfone produces additional BNP-related markers. See, e.g., U.S. Pat. No. 10/419,059, filed Apr. 17, 2003, which is hereby incorporated by reference in its entirety including all tables, figures and claims.

Because production of marker fragments is an ongoing process that may be a function of, inter alia, the elapsed time between onset of an event triggering marker release into the tissues and the time the sample is obtained or analyzed; the elapsed time between sample acquisition and the time the sample is analyzed; the type of tissue sample at issue; the storage conditions; the quantity of proteolytic enzymes present; etc., it may be necessary to consider this degradation when both designing an assay for one or more markers, and when performing such an assay, in order to provide an accurate prognostic or diagnostic result. In addition, individual antibodies that distinguish amongst a plurality of marker fragments may be individually employed to separately detect the presence or amount of different fragments. The results of this individual detection may provide a more accurate prognostic or diagnostic result than detecting the plurality of fragments in a single assay. For example, different weighting factors may be applied to the various fragment measurements to provide a more accurate estimate of the amount of natriuretic peptide originally present in the sample.

In a similar fashion, many of the markers described herein are synthesized as larger precursor molecules, which are then processed to provide mature marker; and/or are present in circulation in the form of fragments of the marker. Thus, "related markers" to each of the markers described herein may be identified and used in an analogous fashion to that described above for BNP.

The failure to consider the degradation fragments that may be present in a clinical sample may have serious consequences for the accuracy of any diagnostic or prognostic method. Consider for example a simple case, where a sandwich immunoassay is provided for BNP, and a significant amount (e.g., 50%) of the biologically active BNP that had been present has now been degraded into an inactive form. An immunoassay formulated with antibodies that bind a region common to the biologically active BNP and the inactive fragment(s) will overestimate the amount of biologically active BNP present in the sample by 2-fold, potentially resulting in a "false positive" result. Overestimation of the biologically active form(s) present in a sample may also have serious consequences for patient management. Considering the BNP example again, the BNP concentration may be used to determine if therapy is effective (e.g., by monitoring BNP to see if an elevated level is returning to normal upon treatment). The same "false positive" BNP result discussed above may lead the physician to continue, increase, or modify treatment because of the false impression that current therapy is ineffective.

Preferred markers of the invention can differentiate between ischemic stroke, hemorrhagic stroke, and TIA. Such markers are referred to herein as "stroke differentiating markers." Particularly preferred are markers that differentiate between thrombotic, embolic, lacunar, hypoperfusion, intracerebral hemorrhage, and subarachnoid hemorrhage types of strokes.

Still other preferred markers of the invention can identify those subjects at risk for a subsequent adverse outcome. For example, a subset of subjects presenting with intracerebral hemorrhage or subarachnoid hemorrhage types of strokes may be susceptible to later vascular injury caused by cerebral vasospasm. In another example, a clinically normal subject may be screened in order to identify a risk of an adverse outcome. Particularly preferred markers are those predictive of a subsequent cerebral vasospasm in patients presenting with subarachnoid hemorrhage, such as von Willebrand factor, vascular endothelial growth factor, matrix metalloprotein-9, or combinations of these markers. Other particularly preferred markers are those that distinguish ischemic stroke from hemorrhagic stroke.

Yet other preferred markers can distinguish the approximate time since stroke onset. Preferred markers for differentiating between acute and non-acute strokes, referred to herein as stroke "time of onset markers" are described hereinafter.

In the exemplary embodiments described hereinafter, a plurality of markers are combined in a "marker panel" to increase the predictive value of the analysis in comparison to that obtained from the markers individually or in smaller groups. The skilled artisan will understand that certain markers in a panel may be commonly used to diagnose the existence of a stroke, while other members of the panel may indicate if an acute stroke has occurred, while still other members of the panel may indicate if an non-acute stroke has occurred. Markers may also be commonly used for multiple purposes by, for example, applying a different threshold or a different weighting factor to the marker for the different purpose(s). For example, a marker at one concentration or weighting may be used, alone or as part of a larger panel, to indicate if an acute stroke has occurred, and the same marker at a different concentration or weighting may be used, alone or as part of a larger panel, to indicate if a non-acute stroke has occurred.

(i) Exemplary Markers Related to Blood Pressure Regulation

In addition to BNP and markers related thereto, discussed in detail above, the following represent exemplary markers that are known in the art to be related to blood pressure regulation. This list is not meant to be limiting.

A-type natriuretic peptide (ANP) (also referred to as atrial natriuretic peptide or cardiodilatin (Forssmann et al *Histochem Cell Biol* 110: 335-357, 1998) is a 28 amino acid peptide that is synthesized, stored, and released atrial myocytes in response to atrial distension, angiotensin II stimulation, endothelin, and sympathetic stimulation (beta-adrenoceptor mediated). ANP is synthesized as a precursor molecule (pro-ANP) that is converted to an active form, ANP, by proteolytic cleavage and also forming N-terminal ANP (1-98). N-terminal ANP and ANP have been reported to increase in patients exhibiting atrial fibrillation and heart failure (Rossi et al. *Journal of the American College of Cardiology* 35: 1256-62, 2000). In addition to atrial natriuretic peptide (ANP99-126) itself, linear peptide fragments from its N-terminal prohormone segment have also been reported to have biological activity. As the skilled artisan will recognize, however, because of its relationship to ANP, the concentration of N-terminal ANP molecule can also provide diagnostic or prognostic information in patients. The phrase "marker related to ANP or ANP related peptide" refers to any polypeptide that originates from the pro-ANP molecule (1-126), other than the 28-amino acid ANP molecule itself. Proteolytic degradation of ANP and of peptides related to ANP have also been described in the literature and these proteolytic fragments are also encompassed it the term "ANP related peptides."

Elevated levels of ANP are found during hypervolemia, atrial fibrillation and congestive heart failure. ANP is involved in the long-term regulation of sodium and water balance, blood volume and arterial pressure. This hormone decreases aldosterone release by the adrenal cortex, increases glomerular filtration rate (GFR), produces natriuresis and diuresis (potassium sparing), and decreases renin release thereby decreasing angiotensin II. These actions contribute to reductions in blood volume and therefore central venous pressure (CVP), cardiac output, and arterial blood pressure. Several isoforms of ANP have been identified, and their relationship to stroke incidence studied. See, e.g., Rubatu et al., *Circulation* 100:1722-6, 1999; Estrada et al., *Am. J. Hypertens.* 7:1085-9, 1994.

Chronic elevations of ANP appear to decrease arterial blood pressure primarily by decreasing systemic vascular resistance. The mechanism of systemic vasodilation may involve ANP receptor-mediated elevations in vascular smooth muscle cGMP as well as by attenuating sympathetic vascular tone. This latter mechanism may involve ANP acting upon sites within the central nervous system as well as through inhibition of norepinephrine release by sympathetic nerve terminals. ANP may be viewed as a counter-regulatory system for the renin-angiotensin system.

C-type natriuretic peptide (CNP) is a 22-amino acid peptide that is the primary active natriuretic peptide in the human brain; CNP is also considered to be an endothelium-derived relaxant factor, which acts in the same way as nitric oxide (NO) (Davidson et al., *Circulation* 93:1155-9, 1996). CNP is structurally related to Atrial natriuretic peptide (ANP) and B-type natriuretic peptide (BNP); however, while ANP and BNP are synthesized predominantly in the myocardium, CNP is synthesized in the vascular endothelium as a precursor (pro-CNP) (Prickett et al., *Biochem. Biophys. Res. Commun.* 286:513-7, 2001). CNP is thought to possess vasodilator effects on both arteries and veins and has been reported to act mainly on the vein by increasing the intracellular cGMP concentration in vascular smooth muscle cells.

Urotensin II is a peptide having the sequence Ala-Gly-Thr-Ala-Asp-Cys-Phe-Trp-Lys-Tyr-Cys-Val, with a disulfide bridge between Cys6 and Cys 11. Human urotensin 2 (UTN) is synthesized in a prepro form. Processed urotensin 2 has potent vasoactive and cardiostimulatory effects, acting on the G protein-linked receptor GPR14.

Vasopressin (arginine vasopressin, AVP; antidiuretic hormone, ADH) is a peptide hormone released from the posterior pituitary. Its primary function in the body is to regulate extracellular fluid volume by affecting renal handling of water. There are several mechanisms regulating release of AVP. Hypovolemia, as occurs during hemorrhage, results in a decrease in atrial pressure. Specialized stretch receptors within the atrial walls and large veins (cardiopulmonary baroreceptors) entering the atria decrease their firing rate when there is a fall in atrial pressure. Afferent from these receptors synapse within the hypothalamus; atrial receptor firing normally inhibits the release of AVP by the posterior pituitary. With hypovolemia or decreased central venous pressure, the decreased firing of atrial stretch receptors leads to an increase in AVP release. Hypothalamic osmoreceptors sense extracellular osmolarity and stimulate AVP release when osmolarity rises, as occurs with dehydration. Finally, angiotensin II receptors located in a region of the hypothalamus regulate AVP release—an increase in angiotensin II simulates AVP release.

AVP has two principle sites of action: kidney and blood vessels. The most important physiological action of AVP is that it increases water reabsorption by the kidneys by increasing water permeability in the collecting duct, thereby permitting the formation of a more concentrated urine. This is the antidiuretic effect of AVP. This hormone also constricts arterial blood vessels; however, the normal physiological concentrations of AVP are below its vasoactive range.

Calcitonin gene related peptide (CGRP) is a polypeptide of 37 amino acids that is a product of the calcitonin gene derived by alternative splicing of the precursor mRNA. The calcitonin gene (CALC-I) primary RNA transcript is processed into different mRNA segments by inclusion or exclusion of different exons as part of the primary transcript. Calcitonin-encoding mRNA is the main product of CALC-I transcription in C-cells of the thyroid, whereas CGRP-I mRNA (CGRP=calcitonin-gene-related peptide) is produced in nervous tissue of the central and peripheral nervous systems (FIGS. 2.2.1) (9). In the third mRNA sequence, the calcitonin sequence is lost and alternatively the sequence of CGRP is encoded in the mRNA. CGRP is a markedly vasoactive peptide with vasodilatative properties. CGRP has no effect on calcium and phosphate metabolism and is synthesised predominantly in nerve cells related to smooth muscle cells of the blood vessels (149). ProCGRP, the precursor of CGRP, and PCT have partly identical N-terminal amino acid sequences.

Procalcitonin is a 116 amino acid (14.5 kDa) protein encoded by the Calc-I gene located on chromosome 11p15.4. The Calc-1 gene produces two transcripts that are the result of alternative splicing events. Pre-procalcitonin contains a 25 amino acid signal peptide which is processed by C-cells in the thyrois to a 57 amino acid N-terminal fragment, a 32 amino acid calcitonin fragment, and a 21 amino acid katacalcin fragment. Procalcitonin is secreted intact as a glycosylated product by other body cells. Whicher et al., Ann. Clin. Biochem. 38: 483-93 (2001). Plasma procalcitonin has been identified as a marker of sepsis and its severity (Yukioka et al., Ann. Acad. Med. Singapore 30: 528-31 (2001)), with day 2 procalcitonin levels predictive of mortality (Pettila et al., Intensive Care Med. 28: 1220-25 (2002).

Angiotensin II is an octapeptide hormone formed by renin action upon a circulating substrate, angiotensinogen, that undergoes proteolytic cleavage to from the decapeptide angiotensin I. Vascular endothelium, particularly in the lungs, has an enzyme, angiotensin converting enzyme (ACE), that cleaves off two amino acids to form the octapeptide, angiotensin II (AII).

AII has several very important functions: Constricts resistance vessels (via AII receptors) thereby increasing systemic vascular resistance and arterial pressure; Acts upon the adrenal cortex to release aldosterone, which in turn acts upon the kidneys to increase sodium and fluid retention; Stimulates the release of vasopressin (antidiuretic hormone, ADH) from the posterior pituitary which acts upon the kidneys to increase fluid retention; Stimulates thirst centers within the brain; Facilitates norepinephrine release from sympathetic nerve endings and inhibits norepinephrine re-uptake by nerve endings, thereby enhancing sympathetic adrenergic function; and Stimulates cardiac hypertrophy and vascular hypertrophy.

Adrenomedullin (AM) is a 52-amino acid peptide which is produced in many tissues, including adrenal medulla, lung, kidney and heart (Yoshitomi et al., Clin. Sci. (Colch) 94:135-9, 1998). Intravenous administration of AM causes a long-lasting hypotensive effect, accompanied with an increase in the cardiac output in experimental animals. AM has been reported to enhance the stretch-induced release of ANP from the right atrium, but not to affect ventricular BNP expression. AM is synthesized as a precursor molecule (pro-AM). The N-terminal peptide processed from the AM precursor has also been reported to act as a hypotensive peptide (Kuwasako et al., Ann. Clin. Biochem. 36:622-8, 1999).

The endothelins are three related peptides (endothelin-1, endothelin-2, and endothelin-3) encoded by separate genes that are produced by vascular endothelium, each of which exhibit potent vasoconstricting activity. Endothelin-1 (ET-1) is a 21 amino acid residue peptide, synthesized as a 212 residue precursor (preproET-1), which contains a 17 residue signal sequence that is removed to provide a peptide known as big ET-1. This molecule is further processed by hydrolysis between trp21 and val22 by endothelin converting enzyme. Both big ET-1 and ET-1 exhibit biological activity; however the mature ET-1 form exhibits greater vasoconstricting activity (Brooks and Ergul, J. Mol. Endocrinol. 21:307-15, 1998). Similarly, endothelin-2 and endothelin-3 are also 21 amino acid residues in length, and are produced by hydrolysis of big endothelin-2 and big endothelin-3, respectively (Yap et al., Br. J. Pharmacol. 129:170-6, 2000; Lee et al., Blood 94:1440-50, 1999).

(ii) Exemplary Markers Related to Coagulation and Hemostasis

The following are exemplary markers related to coagulation and hemostasis. This list is not meant to be limiting.

D-dimer is a crosslinked fibrin degradation product with an approximate molecular mass of 200 kDa. The normal plasma concentration of D-dimer is <150 ng/ml (750 pM). The plasma concentration of D-dimer is elevated in patients with acute myocardial infarction and unstable angina, but not stable angina. Hoffmeister, H. M. et al., Circulation 91: 2520-27 (1995); Bayes-Genis, A. et al., Thromb. Haemost. 81: 865-68 (1999); Gurfinkel, E. et al., Br. Heart J. 71: 151-55 (1994); Kruskal, J. B. et al., N. Engl. J. Med. 317: 1361-65 (1987); Tanaka, M. and Suzuki, A., Thromb. Res. 76: 289-98 (1994).

The plasma concentration of D-dimer also will be elevated during any condition associated with coagulation and fibrinolysis activation, including sepsis, stroke, surgery, atherosclerosis, trauma, and thrombotic thrombocytopenic purpura. D-dimer is released into the bloodstream immediately following proteolytic clot dissolution by plasmin. The plasma concentration of D-dimer can exceed 2 μg/ml in patients with unstable angina. Gurfinkel, E. etal., Br. Heart J. 71: 151-55 (1994). Plasma D-dimer is a specific marker of fibrinolysis and indicates the presence of a prothrombotic state associated with acute myocardial infarction and unstable angina. The plasma concentration of D-dimer is also nearly always elevated in patients with acute pulmonary embolism; thus, normal levels of D-dimer may allow the exclusion of pulmonary embolism. Egermayer et al., Thorax 53: 830-34 (1998).

Plasmin is a 78 kDa serine proteinase that proteolytically digests crosslinked fibrin, resulting in clot dissolution. The 70 kDa serine proteinase inhibitor α2-antiplasmin (α2AP) regulates plasmin activity by forming a covalent 1:1 stoichiometric complex with plasmin. The resulting ~150 kDa plasmin-α2AP complex (PAP), also called plasmin inhibitory complex (PIC) is formed immediately after α2AP comes in contact with plasmin that is activated during fibrinolysis. The normal serum concentration of PAP is <1 μg/ml (6.9 nM). Elevations in the serum concentration of PAP can be attributed to the activation of fibrinolysis. Elevations in the serum concentration of PAP may be associated with clot presence, or any condition that causes or is a result of fibrinolysis activation. These conditions can include atherosclerosis, disseminated intravascular coagulation, acute myocardial infarction, surgery, trauma, unstable angina, stroke, and thrombotic thrombocytopenic purpura. PAP is formed immediately following proteolytic activation of plasmin. PAP is a specific marker for fibrinolysis activation and the presence of a recent or continual hypercoagulable state.

β-thromboglobulin (βTG) is a 36 kDa platelet α granule component that is released upon platelet activation. The normal plasma concentration of βTG is <40 ng/ml (1.1 nM). Plasma levels of β-TG appear to be elevated in patients with unstable angina and acute myocardial infarction, but not stable angina (De Caterina, R. et al., *Eur. Heart J.* 9:913-922, 1988; Bazzan, M. et al., *Cardiologia* 34, 217-220, 1989). Plasma β-TG elevations also seem to be correlated with episodes of ischemia in patients with unstable angina (Sobel, M. et al., *Circulation* 63:300-306, 1981). Elevations in the plasma concentration of βTG may be associated with clot presence, or any condition that causes platelet activation. These conditions can include atherosclerosis, disseminated intravascular coagulation, surgery, trauma, and thrombotic thrombocytopenic purpura, and stroke (Landi, G. et al., *Neurology* 37:1667-1671, 1987). βTG is released into the circulation immediately after platelet activation and aggregation. It has a biphasic half-life of 10 minutes, followed by an extended 1 hour half-life in plasma (Switalska, H. I. et al., *J. Lab. Clin. Med.* 106:690-700, 1985). Plasma βTG concentration is reportedly elevated dring unstable angina and acute myocardial infarction. Special precautions must be taken to avoid platelet activation during the blood sampling process. Platelet activation is common during regular blood sampling, and could lead to artificial elevations of plasma βTG concentration. In addition, the amount of βTG released into the bloodstream is dependent on the platelet count of the individual, which can be quite variable. Plasma concentrations of PTG associated with ACS can approach 70 ng/ml (2 nM), but this value may be influenced by platelet activation during the sampling procedure.

Platelet factor 4 (PF4) is a 40 kDa platelet a granule component that is released upon platelet activation. PF4 is a marker of platelet activation and has the ability to bind and neutralize heparin. The normal plasma concentration of PF4 is <7 ng/ml (175 pM). The plasma concentration of PF4 appears to be elevated in patients with acute myocardial infarction and unstable angina, but not stable angina (Gallino, A. et al., *Am. Heart J.* 112:285-290, 1986; Sakata, K. et al., *Jpn. Circ. J.* 60:277-284, 1996; Bazzan, M. et al., *Cardiologia* 34:217-220, 1989). Plasma PF4 elevations also seem to be correlated with episodes of ischemia in patients with unstable angina (Sobel, M. et al., *Circulation* 63:300-306, 1981). Elevations in the plasma concentration of PF4 may be associated with clot presence, or any condition that causes platelet activation. These conditions can include atherosclerosis, disseminated intravascular coagulation, surgery, trauma, thrombotic thrombocytopenic purpura, and acute stroke (Carter, A. M. et al., *Arterioscler. Thromb. Vasc. Biol.* 18:1124-1131, 1998). PF4 is released into the circulation immediately after platelet activation and aggregation. It has a biphasic half-life of 1 minute, followed by an extended 20 minute half-life in plasma. The half-life of PF4 in plasma can be extended to 20-40 minutes by the presence of heparin (Rucinski, B. et al., *Am. J. Physiol.* 251:H800-H807, 1986). Plasma PF4 concentration is reportedly elevated during unstable angina and acute myocardial infarction, but these studies may not be completely reliable. Special precautions must be taken to avoid platelet activation during the blood sampling process. Platelet activation is common during regular blood sampling, and could lead to artificial elevations of plasma PF4 concentration. In addition, the amount of PF4 released into the bloodstream is dependent on the platelet count of the individual, which can be quite variable. Plasma concentrations of PF4 associated with disease can exceed 100 ng/ml (2.5 nM), but it is likely that this value may be influenced by platelet activation during the sampling procedure.

Fibrinopeptide A (FPA) is a 16 amino acid, 1.5 kDa peptide that is liberated from amino terminus of fibrinogen by the action of thrombin. Fibrinogen is synthesized and secreted by the liver. The normal plasma concentration of FPA is <5 ng/ml (3.3 nM). The plasma FPA concentration is elevated in patients with acute myocardial infarction, unstable angina, and variant angina, but not stable angina (Gensini, G. F. et al., *Thromb. Res.* 50:517-525, 1988; Gallino, A. et al., *Am. Heart J.* 112:285-290, 1986; Sakata, K. et al., *Jpn. Circ. J.* 60:277-284, 1996; Theroux, P. et al., *Circulation* 75:156-162, 1987; Merlini, P. A. et al., *Circulation* 90:61-68, 1994; Manten, A. et al., *Cardiovasc. Res.* 40:389-395, 1998). Furthermore, plasma FPA may indicate the severity of angina (Gensini, G. F. et al., *Thromb. Res.* 50:517-525, 1988). Elevations in the plasma concentration of FPA are associated with any condition that involves activation of the coagulation pathway, including stroke, surgery, cancer, disseminated intravascular coagulation, nephrosis, sepsis, and thrombotic thrombocytopenic purpura. FPA is released into the circulation following thrombin activation and cleavage of fibrinogen. Because FPA is a small polypeptide, it is likely cleared from the bloodstream rapidly. FPA has been demonstrated to be elevated for more than one month following clot formation, and maximum plasma FPA concentrations can exceed 40 ng/ml in active angina (Gensini, G. F. et al., *Thromb. Res.* 50:517-525, 1988; Tohgi, H. et al., *Stroke* 21:1663-1667, 1990).

Platelet-derived growth factor (PDGF) is a 28 kDa secreted homo- or heterodimeric protein composed of the homologous subunits A and/or B (Mahadevan, D. et al., *J. Biol. Chem.* 270:27595-27600, 1995). PDGF is a potent mitogen for mesenchymal cells, and has been implicated in the pathogenesis of atherosclerosis. PDGF is released by aggregating platelets and monocytes near sites of vascular injury. The normal plasma concentration of PDGF is <0.4 ng/ml (15 pM). Plasma PDGF concentrations are higher in individuals with acute myocardial infarction and unstable angina than in healthy controls or individuals with stable angina (Ogawa, H. et al., *Am. J. Cardiol.* 69:453-456, 1992; Wallace, J. M. et al., *Ann. Clin. Biochem.* 35:236-241, 1998; Ogawa, H. et al., *Coron. Artery Dis.* 4:437-442, 1993). Changes in the plasma PDGF concentration in these individuals is most likely due to increased platelet and monocyte activation. Plasma PDGF is elevated in individuals with brain tumors, breast cancer, and hypertension (Kurimoto, M. et al., *Acta Neurochir. (Wien)* 137:182-187, 1995; Seymour, L. et al., *Breast Cancer Res. Treat.* 26:247-252, 1993; Rossi, E. et al., *Am. J. Hypertens.* 11:1239-1243, 1998). Plasma PDGF may also be elevated in any pro-inflammatory condition or any condition that causes platelet activation including surgery, trauma, sepsis, disseminated intravascular coagulation, and thrombotic thrombocytopenic purpura. PDGF is released from the secretory granules of platelets and monocytes upon activation. PDGF has a biphasic half-life of approximately 5 minutes and 1 hour in animals (Cohen, A. M. et al., *J. Surg Res.* 49:447-452, 1990; Bowen-Pope, D. F. et al., *Blood* 64:458-469, 1984). The plasma PDGF concentration in ACS can exceed 0.6 ng/ml (22 pM) (Ogawa, H. et al., *Am. J. Cardiol.* 69:453-456, 1992).

PDGF may be a sensitive and specific marker of platelet activation. In addition, it may be a sensitive marker of vascular injury, and the accompanying monocyte and platelet activation.

Prothrombin fragment 1+2 is 32 kDa polypeptide that is liberated from the amino terminus of thrombin during thrombin activation. The normal plasma concentration of F1+2 is <32 ng/ml (1 nM). The plasma concentration of F1+2 is reportedly elevated in patients with acute myocardial infarction and unstable angina, but not stable angina, but the changes were not robust (Merlini, P. A. et al., *Circulation* 90:61-68, 1994). Other reports have indicated that there is no significant change in the plasma F1+2 concentration in cardiovascular disease (Biasucci, L. M. et al., *Circulation* 93:2121-2127, 1996; Manten, A. et al., *Cardiovasc. Res.* 40:389-395, 1998). The concentration of F1+2 in plasma can be elevated during any condition associated with coagulation activation, including stroke, surgery, trauma, thrombotic thrombocytopenic purpura, and disseminated intravascular coagulation. F1+2 is released into the bloodstream immediately upon thrombin activation. F1+2 has a half-life of approximately 90 minutes in plasma, and it has been suggested that this long half-life may mask bursts of thrombin formation (Biasucci, L. M. et al., *Circulation* 93:2121-2127, 1996).

P-selectin, also called granule membrane protein-140, GMP-140, PADGEM, and CD-62P, is a ~140 kDa adhesion molecule expressed in platelets and endothelial cells. P-selectin is stored in the alpha granules of platelets and in the Weibel-Palade bodies of endothelial cells. Upon activation, P-selectin is rapidly translocated to the surface of endothelial cells and platelets to facilitate the "rolling" cell surface interaction with neutrophils and monocytes. Membrane-bound and soluble forms of P-selectin have been identified. Soluble P-selectin may be produced by shedding of membrane-bound P-selectin, either by proteolysis of the extracellular P-selectin molecule, or by proteolysis of components of the intracellular cytoskeleton in close proximity to the surface-bound P-selectin molecule (Fox, J. E., *Blood Coagul. Fibrinolysis* 5:291-304, 1994). Additionally, soluble P-selectin may be translated from mRNA that does not encode the N-terminal transmembrane domain (Dunlop, L. C. et al., *J. Exp. Med.* 175:1147-1150, 1992; Johnston, G. I. et al., *J. Biol. Chem.* 265:21381-21385, 1990).

Activated platelets can shed membrane-bound P-selectin and remain in the circulation, and the shedding of P-selectin can elevate the plasma P-selectin concentration by approximately 70 ng/ml (Michelson, A. D. et al., *Proc. Natl. Acad. Sci. U S. A.* 93:11877-11882, 1996). Soluble P-selectin may also adopt a different conformation than membrane-bound P-selectin. Soluble P-selectin has a monomeric rod-like structure with a globular domain at one end, and the membrane-bound molecule forms rosette structures with the globular domain facing outward (Ushiyama, S. et al., *J. Biol. Chem.* 268:15229-15237, 1993). Soluble P-selectin may play an important role in regulating inflammation and thrombosis by blocking interactions between leukocytes and activated platelets and endothelial cells (Gamble, J. R. et al., *Science* 249:414-417, 1990). The normal plasma concentration of soluble P-selectin is <200 ng/ml. Blood is normally collected using citrate as an anticoagulant, but some studies have used EDTA plasma with additives such as prostaglandin E to prevent platelet activation. EDTA may be a suitable anticoagulant that will yield results comparable to those obtained using citrate. Furthermore, the plasma concentration of soluble P-selectin may not be affected by potential platelet activation during the sampling procedure. The plasma soluble P-selectin concentration was significantly elevated in patients with acute myocardial infarction and unstable angina, but not stable angina, even following an exercise stress test (Ikeda, H. et al., *Circulation* 92:1693-1696, 1995; Tomoda, H. and Aoki, N., *Angiology* 49:807-813, 1998; Hollander, J. E. et al., *J. Am. Coil. Cardiol.* 34:95-105, 1999; Kaikita, K. et al., *Circulation* 92:1726-1730, 1995; Ikeda, H. et al., *Coron. Artery Dis.* 5:515-518, 1994). The sensitivity and specificity of membrane-bound P-selectin versus soluble P-selectin for acute myocardial infarction is 71% versus 76% and 32% versus 45% (Hollander, J. E. et al., *J. Am. Coll. Cardiol.* 34:95-105, 1999). The sensitivity and specificity of membrane-bound P-selectin versus soluble P-selectin for unstable angina+ acute myocardial infarction is 71% versus 79% and 30% versus 35% (Hollander, J. E. et al., *J. Am. Coil. Cardiol.* 34:95-105, 1999). P-selectin expression is greater in coronary atherectomy specimens from individuals with unstable angina than stable angina (Tenaglia, A. N. et al., *Am. J. Cardiol.* 79:742-747, 1997). Furthermore, plasma soluble P-selectin may be elevated to a greater degree in patients with acute myocardial infarction than in patients with unstable angina. Plasma soluble and membrane-bound P-selectin also is elevated in individuals with non-insulin dependent diabetes mellitus and congestive heart failure (Nomura, S. et al., *Thromb. Haemost.* 80:388-392, 1998; O'Connor, C. M. et al., *Am. J. Cardiol.* 83:1345-1349, 1999). Soluble P-selectin concentration is elevated in the plasma of individuals with idiopathic thrombocytopenic purpura, rheumatoid arthritis, hypercholesterolemia, acute stroke, atherosclerosis, hypertension, acute lung injury, connective tissue disease, thrombotic thrombocytopenic purpura, hemolytic uremic syndrome, disseminated intravascular coagulation, and chronic renal failure (Katayama, M. et al., *Br. J. Haematol.* 84:702-710, 1993; Haznedaroglu, I. C. et al., *Acta Haematol.* 101:16-20, 1999; Ertenli, I. et al., *J. Rheumatol.* 25:1054-1058, 1998; Davi, G. et al., *Circulation* 97:953-957, 1998; Frijns, C. J. et al., *Stroke* 28:2214-2218, 1997; Blann, A. D. et al., *Thromb. Haemost.* 77:1077-1080, 1997; Blann, A. D. et al., *J. Hum. Hypertens.* 11:607-609, 1997; Sakamaki, F. et al., *A. J. Respir. Crit. Care Med.* 151:1821-1826, 1995; Takeda, I. et al., *Int. Arch. Allergy Immunol.* 105:128-134, 1994; Chong, B. H. et al., *Blood* 83:1535-1541, 1994; Bonomini, M. et al., *Nephron* 79:399-407, 1998). Additionally, any condition that involves platelet activation can potentially be a source of plasma elevations in P-selectin. P-selectin is rapidly presented on the cell surface following platelet of endothelial cell activation. Soluble P-selectin that has been translated from an alternative mRNA lacking a transmembrane domain is also released into the extracellular space following this activation. Soluble P-selectin can also be formed by proteolysis involving membrane-bound P-selectin, either directly or indirectly.

Plasma soluble P-selectin is elevated on admission in patients with acute myocardial infarction treated with tPA or coronary angioplasty, with a peak elevation occurring 4 hours after onset (Shimomura, H. et al., *Am. J. Cardiol.* 81:397-400, 1998). Plasma soluble P-selectin was elevated less than one hour following an anginal attack in patients with unstable angina, and the concentration decreased with time, approaching baseline more than 5 hours after attack onset (Ikeda, H. et al., *Circulation* 92:1693-1696, 1995). The plasma concentration of soluble P-selectin can approach 1 µg/ml in ACS (Ikeda, H. et al., *Coron. Artery Dis.* 5:515-518, 1994). Further investigation into the release of soluble P-selectin into and its removal from the bloodstream need to be conducted. P-selectin may be a sensitive and specific marker of platelet and endothelial cell activation, conditions that support thrombus formation and inflammation. It is not, however, a specific marker of ACS. When used with another marker that is specific for cardiac tissue injury, P-selectin may be useful in the discrimination of unstable angina and acute myocardial infarction from stable angina. Furthermore, soluble P-selectin may be elevated to a greater degree in acute myocardial infarction than in unstable angina. P-selectin normally exists in two forms, membrane-bound and soluble. Published investigations note that a soluble form of P-selectin is produced by platelets and endothelial cells, and by shedding of membrane-bound P-selectin, potentially through a proteolytic mechanism. Soluble P-selectin may prove to be the most useful currently identified marker of platelet activation, since its plasma concentration may not be as influenced by the blood sampling procedure as other markers of platelet activation, such as PF4 and β-TG.

Thrombin is a 37 kDa serine proteinase that proteolytically cleaves fibrinogen to form fibrin, which is ultimately integrated into a crosslinked network during clot formation. Antithrombin III (ATIII) is a 65 kDa serine proteinase inhibitor that is a physiological regulator of thrombin, factor XIa, factor XIIa, and factor IXa proteolytic activity. The inhibitory activity of ATIII is dependent upon the binding of heparin. Heparin enhances the inhibitory activity of ATIII by 2-3 orders of magnitude, resulting in almost instantaneous inactivation of proteinases inhibited by ATIII. ATIII inhibits its target proteinases through the formation of a covalent 1:1 stoichiometric complex. The normal plasma concentration of the approximately 100 kDa thrombin-ATIII complex (TAT) is <5 ng/ml (50 pM). TAT concentration is elevated in patients with acute myocardial infarction and unstable angina, especially during spontaneous ischemic episodes (Biasucci, L. M. et al., *Am. J. Cardiol.* 77:85-87, 1996; Kienast, J. et al., *Thromb. Haemost.* 70:550-553, 1993). Furthermore, TAT may be elevated in the plasma of individuals with stable angina (Manten, A. et al., *Cardiovasc. Res.* 40:389-395, 1998). Other published reports have found no significant differences in the concentration of TAT in the plasma of patients with ACS (Manten, A. et al., *Cardiovasc. Res.* 40:389-395, 1998; Hoffmeister, H. M. et al., *Atherosclerosis* 144:151-157, 1999). Further investigation is needed to determine plasma TAT concentration changes associated with ACS. Elevation of the plasma TAT concentration is associated with any condition associated with coagulation activation, including stroke, surgery, trauma, disseminated intravascular coagulation, and thrombotic thrombocytopenic purpura. TAT is formed immediately following thrombin activation in the presence of heparin, which is the limiting factor in this interaction. TAT has a half-life of approximately 5 minutes in the bloodstream (Biasucci, L. M. et al., *Am. J. Cardiol.* 77:85-87, 1996). TAT concentration is elevated in, exhibits a sharp drop after 15 minutes, and returns to baseline less than 1 hour following coagulation activation. The plasma concentration of TAT can approach 50 ng/ml in ACS (Biasucci, L. M. et al., *Circulation* 93:2121-2127, 1996). TAT is a specific marker of coagulation activation, specifically, thrombin activation.

von Willebrand factor (vWF) is a plasma protein produced by platelets, megakaryocytes, and endothelial cells composed of 220 kDa monomers that associate to form a series of high molecular weight multimers. These multimers normally range in molecular weight from 600-20,000 kDa. vWF participates in the coagulation process by stabilizing circulating coagulation factor VIII and by mediating platelet adhesion to exposed subendothelium, as well as to other platelets. The A1 domain of vWF binds to the platelet glycoprotein Ib-IX-V complex and non-fibrillar collagen type VI, and the A3 domain binds fibrillar collagen types I and III (Emsley, J. et al., *J. Biol. Chem.* 273:10396-10401, 1998). Other domains present in the vWF molecule include the integrin binding domain, which mediates platelet-platelet interactions, the protease cleavage domain, which appears to be relevant to the pathogenesis of type 11A von Willebrand disease. The interaction of vWF with platelets is tightly regulated to avoid interactions between vWF and platelets in normal physiologic conditions. vWF normally exists in a globular state, and it undergoes a conformation transition to an extended chain structure under conditions of high sheer stress, commonly found at sites of vascular injury. This conformational change exposes intramolecular domains of the molecule and allows vWF to interact with platelets. Furthermore, shear stress may cause vWF release from endothelial cells, making a larger number of vWF molecules available for interactions with platelets. The conformational change in vWF can be induced in vitro by the addition of non-physiological modulators like ristocetin and botrocetin (Miyata, S. et al., *J. Biol. Chem.* 271:9046-9053, 1996). At sites of vascular injury, vWF rapidly associates with collagen in the subendothelial matrix, and virtually irreversibly binds platelets, effectively forming a bridge between platelets and the vascular subendothelium at the site of injury. Evidence also suggests that a conformational change in vWF may not be required for its interaction with the subendothelial matrix (Sixma, J. J. and de Groot, P. G., *Mayo Clin. Proc.* 66:628-633, 1991). This suggests that vWF may bind to the exposed subendothelial matrix at sites of vascular injury, undergo a conformational change because of the high localized shear stress, and rapidly bind circulating platelets, which will be integrated into the newly formed thrombus.

Measurement of the total amount of vWF would allow one who is skilled in the art to identify changes in total vWF concentration. This measurement could be performed through the measurement of various forms of the vWF molecule. Measurement of the A1 domain would allow the measurement of active vWF in the circulation, indicating that a pro-coagulant state exists because the A1 domain is accessible for platelet binding. In this regard, an assay that specifically measures vWF molecules with both the exposed A1 domain and either the integrin binding domain or the A3 domain would also allow for the identification of active vWF that would be available for mediating platelet-platelet interactions or mediate crosslinking of platelets to vascular subendothelium, respectively. Measurement of any of these vWF forms, when used in an assay that employs antibodies specific for the protease cleavage domain may allow assays to be used to determine the circulating concentration of various vWF forms in any individual, regardless of the presence of von Willebrand disease. The normal plasma concentration of vWF is 5-10 µg/ml, or 60-110% activity, as measured by platelet aggregation. The measurement of specific forms of vWF may be of importance in any type of vascular disease, including stroke and cardiovascular disease. The plasma vWF concentration is reportedly elevated in individuals with acute myocardial infarction and unstable angina, but not stable angina (Goto, S. et al., *Circulation* 99:608-613, 1999; Tousoulis, D. et al., *Int. J. Cardiol.* 56:259-262, 1996; Yazdani, S. et al., *J. Am Coll Cardiol* 30:1284-1287, 1997; Montalescot, G. et al., *Circulation* 98:294-299).

The plasma concentration of vWF may be elevated in conjunction with any event that is associated with endothelial cell damage or platelet activation. vWF is present at high concentration in the bloodstream, and it is released from platelets and endothelial cells upon activation. vWF would likely have the greatest utility as a marker of platelet activation or, specifically, conditions that favor platelet activation and adhesion to sites of vascular injury. The conformation of VWF is also known to be altered by high shear stress, as would be associated with a partially stenosed blood vessel. As the blood flows past a stenosed vessel, it is subjected to shear stress considerably higher than is encountered in the circulation of an undiseased individual.

Tissue factor (TF) is a 45 kDa cell surface protein expressed in brain, kidney, and heart, and in a transcriptionally regulated manner on perivascular cells and monocytes. TF forms a complex with factor VIIa in the presence of $Ca^{2+}$ ions, and it is physiologically active when it is membrane bound. This complex proteolytically cleaves factor X to form factor Xa. It is normally sequestered from the bloodstream. Tissue factor can be detected in the bloodstream in a soluble form, bound to factor VIIa, or in a complex with factor VIIa, and tissue factor pathway inhibitor that can also include factor Xa. TF also is expressed on the surface of macrophages, which are commonly found in atherosclerotic plaques. The normal serum concentration of TF is <0.2 ng/ml (4.5 pM). The plasma TF concentration is elevated in patients with ischemic heart disease (Falciani, M. et al., *Thromb. Haemost.* 79:495-499, 1998). TF is elevated in patients with unstable angina and acute myocardial infarction, but not in patients with stable angina (Falciani, M. et al., *Thromb. Haemost.* 79:495-499, 1998; Suefuji, H. et al., *Am. Heart J.* 134:253-259, 1997; Misumi, K. et al., *Am. J. Cardiol.* 81:22-26, 1998). Furthermore, TF expression on macrophages and TF activity in atherosclerotic plaques is more common in unstable angina than stable angina (Soejima, H. et al., *Circulation* 99:2908-2913, 1999; Kaikita, K. et al., *Arterioscler. Thromb. Vasc. Biol.* 17:2232-2237, 1997; Ardissino, D. et al., *Lancet* 349: 769-771, 1997).

The differences in plasma TF concentration in stable versus unstable angina may not be of statistical significance. Elevations in the serum concentration of TF are associated with any condition that causes or is a result of coagulation activation through the extrinsic pathway. These conditions can include subarachnoid hemorrhage, disseminated intravascular coagulation, renal failure, vasculitis, and sickle cell disease (Hirashima, Y. et al., *Stroke* 28:1666-1670, 1997; Takahashi, H. et al., *Am. J. Hematol.* 46:333-337, 1994; Koyama, T. et al., *Br. J. Haematol.* 87:343-347, 1994). TF is released immediately when vascular injury is coupled with extravascular cell injury. TF levels in ischemic heart disease patients can exceed 800 pg/ml within 2 days of onset (Falciani, M. et al., *Thromb. Haemost.* 79:495-499, 1998. TF levels were decreased in the chronic phase of acute myocardial infarction, as compared with the chronic phase (Suefuji, H. et al., *Am. Heart J.* 134:253-259, 1997). TF is a specific marker for activation of the extrinsic coagulation pathway and the presence of a general hypercoagulable state. It may be a sensitive marker of vascular injury resulting from plaque rupture The coagulation cascade can be activated through either the extrinsic or intrinsic pathways. These enzymatic pathways share one final common pathway. The first step of the common pathway involves the proteolytic cleavage of prothrombin by the factor Xa/factor Va prothrombinase complex to yield active thrombin. Thrombin is a serine proteinase that proteolytically cleaves fibrinogen. Thrombin first removes fibrinopeptide A from fibrinogen, yielding desAA fibrin monomer, which can form complexes with all other fibrinogen-derived proteins, including fibrin degradation products, fibrinogen degradation products, desAA fibrin, and fibrinogen. The desAA fibrin monomer is generically referred to as soluble fibrin, as it is the first product of fibrinogen cleavage, but it is not yet crosslinked via factor XIIIa into an insoluble fibrin clot. DesAA fibrin monomer also can undergo further proteolytic cleavage by thrombin to remove fibrinopeptide B, yielding desAABB fibrin monomer. This monomer can polymerize with other desAABB fibrin monomers to form soluble desAABB fibrin polymer, also referred to as "soluble fibrin" or "thrombus precursor protein" (TpP™). TpP™ is the immediate precursor to insoluble fibrin, which forms a "mesh-like" structure to provide structural rigidity to the newly formed thrombus. In this regard, measurement of TpP™ in plasma is a direct measurement of active clot formation.

The normal plasma concentration of TpP™ is <6 ng/ml (Laurino, J. P. et al., *Ann. Clin. Lab. Sci.* 27:338-345, 1997). American Biogenetic Sciences has developed an assay for TpP™ (U.S. Pat. Nos. 5,453,359 and 5,843,690) and states that its TpP™ assay can assist in the early diagnosis of acute myocardial infarction, the ruling out of acute myocardial infarction in chest pain patients, and the identification of patients with unstable angina that will progress to acute myocardial infarction. Other studies have confirmed that TpP™ is elevated in patients with acute myocardial infarction, most often within 6 hours of onset (Laurino, J. P. et al., *Ann. Clin. Lab. Sci.* 27:338-345, 1997; Carville, D. G. et al., *Clin. Chem.* 42:1537-1541, 1996). The plasma concentration of TpP™ is also elevated in patients with unstable angina, but these elevations may be indicative of the severity of angina and the eventual progression to acute myocardial infarction (Laurino, J. P. et al., *Ann. Clin. Lab. Sci.* 27:338-345, 1997). The concentration of TpP™ in plasma will theoretically be elevated during any condition that causes or is a result of coagulation activation, including disseminated intravascular coagulation, deep venous thrombosis, congestive heart failure, surgery, cancer, gastroenteritis, and cocaine overdose (Laurino, J. P. et al., *Ann. Clin. Lab. Sci.* 27:338-345, 1997). TpP™ is released into the bloodstream immediately following thrombin activation. TpP™ likely has a short half-life in the bloodstream because it will be rapidly converted to insoluble fibrin at the site of clot formation. Plasma TpP™ concentrations peak within 3 hours of acute myocardial infarction onset, returning to normal after 12 hours from onset. The plasma concentration of TpP™ can exceed 30 ng/ml in CVD (Laurino, J. P. et al., *Ann. Clin. Lab. Sci.* 27:338-345, 1997). TpP™ is a sensitive and specific marker of coagulation activation. It has been demonstrated that TpP™ is useful in the diagnosis of acute myocardial infarction, but only when it is used in conjunction with a specific marker of cardiac tissue injury.

(iii) Exemplary Markers Related to the Acute Phase Response

Acute phase proteins are a group of proteins, such as C-reactive protein and mannose-binding protein, produced by cells in the liver and that promote inflammation, activate the complement cascade, and stimulate chemotaxis of phagocytes. The following are exemplary markers related to the acute phase response. This list is not meant to be limiting.

Human neutrophil elastase (HNE) is a 30 kDa serine proteinase that is normally contained within the azurophilic granules of neutrophils. HNE is released upon neutrophil activation, and its activity is regulated by circulating $\alpha_1$-proteinase inhibitor. Activated neutrophils are commonly found in atherosclerotic plaques, and rupture of these plaques may result in the release of HNE. The plasma HNE concentration is usually measured by detecting HNE-$\alpha_1$-PI complexes. The normal concentration of these complexes is 50 ng/ml, which indicates a normal concentration of approximately 25 ng/ml (0.8 nM) for HNE. HNE release also can be measured through the specific detection of fibrinopeptide $B\beta_{30-43}$, a specific HNE-derived fibrinopeptide, in plasma. Plasma HNE is elevated in patients with coronary stenosis, and its elevation is greater in patients with complex plaques than those with simple plaques (Kosar, F. et al., *Angiology* 49:193-201, 1998; Amaro, A. et al., *Eur. Heart J.* 16:615-622, 1995). Plasma HNE is not significantly elevated in patients with stable angina, but is elevated inpatients with unstable angina and acute myocardial infarction, as determined by measuring fibrinopeptide B$\beta_{30-43}$, with concentrations in unstable angina being 2.5-fold higher than those associated with acute myocardial infarction (Dinerman, J. L. et al., *J. Am. Coll. Cardiol.* 15:1559-1563, 1990; Mehta, J. et al., *Circulation* 79:549-556, 1989). Serum HNE is elevated in cardiac surgery, exercise-induced muscle damage, giant cell arteritis, acute respiratory distress syndrome, appendicitis, pancreatitis, sepsis, smoking-associated emphysema, and cystic fibrosis (Genereau, T. et al., *J. Rheumatol.* 25:710-713, 1998; Mooser, V. et al., *Arterioscler. Thromb. Vasc. Biol.* 19:1060-1065, 1999; Gleeson, M. et al. *Eur. J. Appl. Physiol.* 77:543-546, 1998; Gando, S. et al., *J. Trauma* 42:1068-1072, 1997; Eriksson, S. et al., *Eur. J. Surg.* 161:901-905, 1995; Liras, G. et al., *Rev. Esp. Enferm. Dig.* 87:641-652, 1995; Endo, S. et al., *J. Inflamm.* 45:136-142, 1995; Janoff, A., *Annu Rev Med* 36:207-216, 1985). HNE may also be released during blood coagulation (Plow, E. F. and Plescia, J., *Thromb. Haemost.* 59:360-363, 1988; Plow, E. F., *J. Clin. Invest.* 69:564-572, 1982). Serum elevations of HNE could also be associated with any non-specific infection or inflammatory state that involves neutrophil recruitment and activation. It is most likely released upon plaque rupture, since activated neutrophils are present in atherosclerotic plaques. HNE is presumably cleared by the liver after it has formed a complex with $\alpha_1$-PI.

Inducible nitric oxide synthase (iNOS) is a 130 kDa cytosolic protein in epithelial cells macrophages whose expression is regulated by cytokines, including interferon-$\gamma$, interleukin-1$\beta$, interleukin-6, and tumor necrosis factor $\alpha$, and lipopolysaccharide. iNOS catalyzes the synthesis of nitric oxide (NO) from L-arginine, and its induction results in a sustained high-output production of NO, which has antimicrobial activity and is a mediator of a variety of physiological and inflammatory events. NO production by iNOS is approximately 100 fold more than the amount produced by constitutively-expressed NOS (Depre, C. et al., *Cardiovasc. Res.* 41:465-472, 1999). There are no published investigations of plasma iNOS concentration changes associated with ACS. iNOS is expressed in coronary atherosclerotic plaque, and it may interfere with plaque stability through the production of peroxynitrate, which is a product of NO and superoxide and enhances platelet adhesion and aggregation (Depre, C. et al., *Cardiovasc. Res.* 41:465-472, 1999). iNOS expression during myocardial ischemia may not be elevated, suggesting that iNOS may be useful in the differentiation of angina from acute myocardial infarction (Hammerman, S. I. et al., *Am. J. Physiol.* 277:H1579-H1592, 1999; Kaye, D. M. et al., *Life Sci* 62:883-887, 1998). Elevations in the plasma iNOS concentration may be associated with cirrhosis, iron-deficiency anemia, or any other condition that results in macrophage activation, including bacterial infection (Jimenez, W. et al., *Hepatology* 30:670-676, 1999; Ni, Z. et al., *Kidney Int.* 52:195-201, 1997). iNOS may be released into the bloodstream as a result of atherosclerotic plaque rupture, and the presence of increased amounts of iNOS in the bloodstream may not only indicate that plaque rupture has occurred, but also that an ideal environment has been created to promote platelet adhesion. However, iNOS is not specific for atherosclerotic plaque rupture, and its expression can be induced during non-specific inflammatory conditions.

Lysophosphatidic acid (LPA) is a lysophospholipid intermediate formed in the synthesis of phosphoglycerides and triacylglycerols. It is formed by the acylation of glycerol-3 phosphate by acyl-coenzyme A and during mild oxidation of low-density lipoprotein (LDL). LPA is a lipid second messenger with vasoactive properties, and it can function as a platelet activator. LPA is a component of atherosclerotic lesions, particularly in the core, which is most prone to rupture (Siess, W., *Proc. Natl. Acad. Sci. U.S.A.* 96, 6931-6936, 1999). The normal plasma LPA concentration is 540 nM. Serum LPA is elevated in renal failure and in ovarian cancer and other gynecologic cancers (Sasagawa, T. et al., *J. Nutr. Sci. Vitaminol.* (Tokyo) 44:809-818, 1998; Xu, Y. et al., *JAMA* 280:719-723, 1998). In the context of unstable angina, LPA is most likely released as a direct result of plaque rupture. The plasma LPA concentration can exceed 60 µM in patients with gynecologic cancers (Xu, Y. et al., *JAMA* 280:719-723, 1998). Serum LPA may be a useful marker of atherosclerotic plaque rupture.

Malondialdehyde-modified low-density lipoprotein (MDA-modified LDL) is formed during the oxidation of the apoB-100 moiety of LDL as a result of phospholipase activity, prostaglandin synthesis, or platelet activation. MDA-modified LDL can be distinguished from oxidized LDL because MDA modifications of LDL occur in the absence of lipid peroxidation (Holvoet, P., *Acta Cardiol.* 53:253-260, 1998). The normal plasma concentration of MDA-modified LDL is less than 4 µg/ml (~10 µM). Plasma concentrations of oxidized LDL are elevated in stable angina, unstable angina, and acute myocardial infarction, indicating that it may be a marker of atherosclerosis (Holvoet, P., *Acta Cardiol.* 53:253-260, 1998; Holvoet, P. et al., *Circulation* 98:1487-1494, 1998). Plasma MDA-modified LDL is not elevated in stable angina, but is significantly elevated in unstable angina and acute myocardial infarction (Holvoet, P., *Acta Cardiol.* 53:253-260, 1998; Holvoet, P. et al., *Circulation* 98:1487-1494, 1998; Holvoet, P. et al., *JAMA* 281:1718-1721, 1999). Plasma MDA-modified LDL is elevated in individuals with beta-thallasemia and in renal transplant patients (Livrea, M. A. et al., *Blood* 92:3936-3942, 1998; Ghanem, H. et al., *Kidney Int.* 49:488-493, 1996; van den Dorpel, M. A. et al., *Transpl. Int. 9 Suppl.* 1:S54-S57, 1996). Furthermore, serum MDA-modified LDL may be elevated during hypoxia (Balagopalakrishna, C. et al., *Adv. Exp. Med. Biol.* 411:337-345, 1997). The plasma concentration of MDA-modified LDL is elevated within 6-8 hours from the onset of chest pain. Plasma concentrations of MDA-modified LDL can approach 20 µg/ml (~50 µM) in patients with acute myocardial infarction, and 15 µg/ml (~40 µM) in patients with unstable angina (Holvoet, P. et al., *Circulation* 98:1487-1494, 1998). Plasma MDA-modified LDL has a half-life of less than 5 minutes in mice (Ling, W. et al., *J. Clin. Invest.* 100:244-252, 1997). MDA-modified LDL appears to be a specific marker of atherosclerotic plaque rupture in acute coronary symptoms. It is unclear, however, if elevations in the plasma concentration of MDA-modified LDL are a result of plaque rupture or platelet activation. The most reasonable explanation is that the presence of increased amounts of MDA-modified LDL is an indication of both events. MDA-modified LDL may be useful in discriminating unstable angina and acute myocardial infarction from stable angina.

Matrix metalloproteinase-1 (MMP-1), also called collagenase-1, is a 41/44 kDa zinc- and calcium-binding proteinase that cleaves primarily type I collagen, but can also cleave collagen types II, III, VII and X. The active 41/44 kDa enzyme can undergo autolysis to the still active 22/27 kDa form. MMP-1 is synthesized by a variety of cells, including smooth muscle cells, mast cells, macrophage-derived foam cells, T lymphocytes, and endothelial cells (Johnson, J. L. et al., *Arterioscler. Thromb. Vasc. Biol. 18:1707-1715, 1998). MMP-1, like other MMPs, is involved in extracellular matrix remodeling, which can occur following injury or during intervascular cell migration. MMP-1 can be found in the bloodstream either in a free form or in complex with TIMP-1, its natural inhibitor. MMP-1 is normally found at a concentration of <25 ng/ml in plasma. MMP-1 is found in the shoulder region of atherosclerotic plaques, which is the region most prone to rupture, and may be involved in atherosclerotic plaque destabilization (Johnson, J. L. et al., *Arterioscler. Thromb. Vasc. Biol.* 18:1707-1715, 1998). Furthermore, MMP-1 has been implicated in the pathogenesis of myocardial reperfusion injury (Shibata, M. et al., *Angiology* 50:573-582, 1999). Serum MMP-1 may be elevated inflammatory conditions that induce mast cell degranulation. Serum MMP-1 concentrations are elevated in patients with arthritis and systemic lupus erythematosus (Keyszer, G. et al., *Z Rheumatol* 57:392-398, 1998; Keyszer, G. *J. Rheumatol.* 26:251-258, 1999). Serum MMP-1 also is elevated in patients with prostate cancer, and the degree of elevation corresponds to the metastatic potential of the tumor (Baker, T. et al., *Br. J. Cancer* 70:506-512, 1994). The serum concentration of MMP-1 may also be elevated in patients with other types of cancer. Serum MMP-1 is decreased in patients with hemochromatosis and also in patients with chronic viral hepatitis, where the concentration is inversely related to the severity (George, D. K. et al., *Gut* 42:715-720, 1998; Murawaki, Y. et al., *J. Gastroenterol. Hepatol.* 14:138-145, 1999). Serum MMP-1 was decreased in the first four days following acute myocardial infarction, and increased thereafter, reaching peak levels 2 weeks after the onset of acute myocardial infarction (George, D. K. et al., *Gut* 42:715-720, 1998).

Lipopolysaccharide binding protein (LBP) is a ~60 kDa acute phase protein produced by the liver. LBP binds to lipopolysaccharide and is involved in LPS handling in humans. LBP has been reported to mediate transfer of LPS to the LPS receptor (CD14) on mononuclear cells, and into HDL. LBP has also been reported to protect mice from septic shock caused by LPS.

Matrix metalloproteinase-2 (MMP-2), also called gelatinase A, is a 66 kDa zinc- and calcium-binding proteinase that is synthesized as an inactive 72 kDa precursor. Mature MMP-3 cleaves type I gelatin and collagen of types IV, V, VII, and X. MMP-2 is synthesized by a variety of cells, including vascular smooth muscle cells, mast cells, macrophage-derived foam cells, T lymphocytes, and endothelial cells (Johnson, J. L. et al., *Arterioscler. Thromb. Vasc. Biol.* 18:1707-1715, 1998). MMP-2 is usually found in plasma in complex with TIMP-2, its physiological regulator (Murawaki, Y. et al., *J. Hepatol.* 30:1090-1098, 1999). The normal plasma concentration of MMP-2 is <~550 ng/ml (8 nM). MMP-2 expression is elevated in vascular smooth muscle cells within atherosclerotic lesions, and it may be released into the bloodstream in cases of plaque instability (Kai, H. et al., *J. Am. Coll. Cardiol.* 32:368-372, 1998). Furthermore, MMP-2 has been implicated as a contributor to plaque instability and rupture (Shah, P. K. et al., *Circulation* 92:1565-1569, 1995). Serum MMP-2 concentrations were elevated in patients with stable angina, unstable angina, and acute myocardial infarction, with elevations being significantly greater in unstable angina and acute myocardial infarction than in stable angina (Kai, H. et al., *J. Am. Coll. Cardiol.* 32:368-372, 1998). There was no change in the serum MMP-2 concentration in individuals with stable angina following a treadmill exercise test (Kai, H. et al., *J. Am. Coll. Cardiol.* 32:368-372, 1998). Serum and plasma MMP-2 is elevated in patients with gastric cancer, hepatocellular carcinoma, liver cirrhosis, urothelial carcinoma, rheumatoid arthritis, and lung cancer (Murawaki, Y. et al., *J. Hepatol.* 30:1090-1098, 1999; Endo, K. et al., *Anticancer Res.* 17:2253-2258, 1997; Gohji, K. et al., *Cancer* 78:2379-2387, 1996; Gruber, B. L. et al., *Clin. Immunol. Immunopathol.* 78:161-171, 1996; Garbisa, S. et al., *Cancer Res.* 52:4548-4549, 1992). Furthermore, MMP-2 may also be translocated from the platelet cytosol to the extracellular space during platelet aggregation (Sawicki, G. et al., *Thromb. Haemost.* 80:836-839, 1998). MMP-2 was elevated on admission in the serum of individuals with unstable angina and acute myocardial infarction, with maximum levels approaching 1.5 µg/ml (25 nM) (Kai, H. et al., *J. Am. Coll. Cardiol.* 32:368-372, 1998). The serum MMP-2 concentration peaked 1-3 days after onset in both unstable angina and acute myocardial infarction, and started to return to normal after 1 week (Kai, H. et al., *J. Am. Coll. Cardiol.* 32:368-372, 1998).

Matrix metalloproteinase-3 (MMP-3), also called stromelysin-1, is a 45 kDa zinc- and calcium-binding proteinase that is synthesized as an inactive 60 kDa precursor. Mature MMP-3 cleaves proteoglycan, fibrinectin, laminin, and type IV collagen, but not type I collagen. MMP-3 is synthesized by a variety of cells, including smooth muscle cells, mast cells, macrophage-derived foam cells, T lymphocytes, and endothelial cells (Johnson, J. L. et al., *Arterioscler. Thromb. Vasc. Biol.* 18:1707-1715, 1998). MMP-3, like other MMPs, is involved in extracellular matrix remodeling, which can occur following injury or during intervascular cell migration. MMP-3 is normally found at a concentration of <125 ng/ml in plasma. The serum MMP-3 concentration also has been shown to increase with age, and the concentration in males is approximately 2 times higher in males than in females (Manicourt, D. H. et al., *Arthritis Rheum.* 37:1774-1783, 1994). MMP-3 is found in the shoulder region of atherosclerotic plaques, which is the region most prone to rupture, and may be involved in atherosclerotic plaque destabilization (Johnson, J. L. et al., *Arterioscler. Thromb. Vasc. Biol.* 18:1707-1715, 1998). Therefore, MMP-3 concentration may be elevated as a result of atherosclerotic plaque rupture in unstable angina. Serum MMP-3 may be elevated inflammatory conditions that induce mast cell degranulation. Serum MMP-3 concentrations are elevated in patients with arthritis and systemic lupus erythematosus (Zucker, S. et al. *J. Rheumatol.* 26:78-80, 1999; Keyszer, G. et al., *Z Rheumatol.* 57:392-398, 1998; Keyszer, G. et al. *J. Rheumatol.* 26:251-258, 1999). Serum MMP-3 also is elevated in patients with prostate and urothelial cancer, and also glomerulonephritis (Lein, M. et al., *Urologe A* 37:377-381, 1998; Gohji, K. et al., *Cancer* 78:2379-2387, 1996; Akiyama, K. et al., *Res. Commun. Mol. Pathol. Pharmacol.* 95:115-128, 1997). The serum concentration of MMP-3 may also be elevated in patients with other types of cancer. Serum MMP-3 is decreased in patients with hemochromatosis (George, D. K. et al., *Gut* 42:715-720, 1998).

Matrix metalloproteinase-9 (MMP-9) also called gelatinase B, is an 84 kDa zinc- and calcium-binding proteinase that is synthesized as an inactive 92 kDa precursor. Mature MMP-9 cleaves gelatin types I and V, and collagen types IV and V. MMP-9 exists as a monomer, a homodimer, and a heterodimer with a 25 kDa $\alpha_2$-microglobulin-related protein (Triebel, S. et al., *FEBS Lett.* 314:386-388, 1992). MMP-9 is synthesized by a variety of cell types, most notably by neutrophils. The normal plasma concentration of MMP-9 is <35 ng/ml (400 pM). MMP-9 expression is elevated in vascular smooth muscle cells within atherosclerotic lesions, and it may be released into the bloodstream in cases of plaque instability (Kai, H. et al., *J. Am. Coll. Cardiol.* 32:368-372, 1998). Furthermore, MMP-9 may have a pathogenic role in the development of ACS (Brown, D. L. et al., *Circulation* 91:2125-2131, 1995). Plasma MMP-9 concentrations are significantly elevated in patients with unstable angina and acute myocardial infarction, but not stable angina (Kai, H. et al., *J. Am. Coll. Cardiol.* 32:368-372, 1998). The elevations in patients with acute myocardial infarction may also indicate that those individuals were suffering from unstable angina. Elevations in the plasma concentration of MMP-9 may also be greater in unstable angina than in acute myocardial infarction. There was no significant change in plasma MMP-9 levels after a treadmill exercise test in patients with stable angina (Kai, H. et al., *J. Am. Coll. Cardiol.* 32:368-372, 1998). Plasma MMP-9 is elevated in individuals with rheumatoid arthritis, septic shock, giant cell arteritis and various carcinomas (Gruber, B. L. et al., *Clin. Immunol. Immunopathol.* 78:161-171, 1996; Nakamura, T. et al., *Am. J. Med. Sci.* 316:355-360, 1998; Blankaert, D. et al., *J. Acquir. Immune Defic. Syndr. Hum. Retrovirol.* 18:203-209, 1998; Endo, K. et al. *Anticancer Res.* 17:2253-2258, 1997; Hayasaka, A. et al., *Hepatology* 24:1058-1062, 1996; Moore, D. H. et al., *Gynecol. Oncol.* 65:78-82, 1997; Sorbi, D. et al., *Arthritis Rheum.* 39:1747-1753, 1996; Iizasa, T. et al., *Clin., Cancer Res.* 5:149-153, 1999). Furthermore, the plasma MMP-9 concentration may be elevated in stroke and cerebral hemorrhage (Mun-Bryce, S. and Rosenberg, G. A., *J. Cereb. Blood Flow Metab.* 18:1163-1172, 1998; Romanic, A. M. et al., *Stroke* 29:1020-1030, 1998; Rosenberg, G. A., *J. Neurotrauma* 12:833-842, 1995). MMP-9 was elevated on admission in the serum of individuals with unstable angina and acute myocardial infarction, with maximum levels approaching 150 ng/ml (1.7 nM) (Kai, H. et al., *J. Am. Coll. Cardiol.* 32:368-372, 1998). The serum MMP-9 concentration was highest on admission in patients unstable angina, and the concentration decreased gradually after treatment, approaching baseline more than 1 week after onset (Kai, H. etal., *J. Am. Coll. Cardiol.* 32:368-372, 1998).

The balance between matrix metalloproteinases and their inhibitors is a critical factor which affects tumor invasion and metastasis. The TIMP family represents a class of small (21-28 kDa) related proteins that inhibit the metalloproteinases. Tissue inhibitor of metalloproteinase 1 (TIMP1) is reportedly involved in the regulation of bone modeling and remodeling in normal developing human bone, involved in the invasive phenotype of acute myelogenous leukemia, demonstrating polymorphic X-chromosome inactivation. TIMP1 is known to act on mmp-1, mmp-2, mmp-3, mmp-7, mmp-8, mmp-9, mmp-10, mmp-11, mmp-12, mmp-13 and mmp-16. Tissue inhibitor of metalloproteinase 2 (TIMP2) complexes with metalloproteinases (such as collagenases) and irreversibly inactivates them. TIMP2 is known to act on mmp-1, mmp-2, mmp-3, mmp-7, mmp-8, mmp-9, mmp-10, mmp-13, mmp-14, mmp-15, mmp-16 and mmp-19. Two alternatively spliced forms may be associated with SYN4, and involved in the invasive phenotype of acute myelogenous leukemia. Unlike the inducible expression of some other TIMP gene family members, the expression of this gene is largely constitutive. Tissue inhibitor of metalloproteinase 3 (TIMP3) antagonizes matrix metalloproteinase activity and can suppress tumor growth, angiogenesis, invasion, and metastasis. Loss of TIMP-3 has been related to the acquisition of tumorigenesis.

(iv) Exemplary Markers Related to Inflammation

Acute phase proteins are part of a larger group of proteins that are related to local or systemic inflammation. The following exemplary list is not meant to be limiting.

Interleukins (ILs) are part of a larger class of polypeptides known as cytokines. These are messenger molecules that transmit signals between various cells of the immune system. They are mostly secreted by macrophages and lymphocytes and their production is induced in response to injury or infection. Their actions influence other cells of the immune system as well as other tissues and organs including the liver and brain. There are at least 18 ILs described. IL-1β, IL-2, IL-4, IL-6, IL-8 and IL-10 are preferred for use as markers in the present invention. The following table shows selected functions of representative interleukins.

TABLE 1

Selected Functions of Representative Interleukins*

| Functions | IL-1 | IL-2 | IL-4 | IL-6 | IL-8 | IL-10 |
| --- | --- | --- | --- | --- | --- | --- |
| Enhance immune responses | + | + | + | + | − | + |
| Suppress immune responses | − | − | − | − | − | + |
| Enhance inflammation | + | + | + | + | + | − |
| Suppress inflammation | − | − | − | − | − | + |
| Promote cell growth | + | + | − | − | − | − |
| Chemotactic (chemokines) | − | − | − | − | + | − |
| Pyrogenic | + | − | − | − | − | − |

Interleukin-1β (IL-1β) is a 17 kDa secreted proinflammatory cytokine that is involved in the acute phase response and is a pathogenic mediator of many diseases. IL-1β is normally produced by macrophages and epithelial cells. IL-1β is also released from cells undergoing apoptosis. The normal serum concentration of IL-1β is <30 pg/ml (1.8 pM). In theory, IL-1β would be elevated earlier than other acute phase proteins such as CRP in unstable angina and acute myocardial infarction, since IL-1β is an early participant in the acute phase response. Furthermore, IL-1β is released from cells undergoing apoptosis, which may be activated in the early stages of ischemia. In this regard, elevation of the plasma IL-1β concentration associated with ACS requires further investigation using a high-sensitivity assay. Elevations of the plasma IL-1β concentration are associated with activation of the acute phase response in proinflammatory conditions such as trauma and infection. IL-1β has a biphasic physiological half-life of 5 minutes followed by 4 hours (Kudo, S. et al., *Cancer Res.* 50:5751-5755, 1990). IL-1β is released into the extracellular milieu upon activation of the inflammatory response or apoptosis.

Interleukin-1 receptor antagonist (IL-1ra) is a 17 kDa member of the IL-1 family predominantly expressed in hepatocytes, epithelial cells, monocytes, macrophages, and neutrophils. IL-1ra has both intracellular and extracellular forms produced through alternative splicing. IL-1ra is thought to participate in the regulation of physiological IL-1 activity. IL-1ra has no IL-1-like physiological activity, but is able to bind the IL-1 receptor on T-cells and fibroblasts with an affinity similar to that of IL-1β, blocking the binding of IL-1α and IL-1β and inhibiting their bioactivity (Stockman, B. J. et al., *Biochemistry* 31:5237-5245, 1992; Eisenberg, S. P. et al., *Proc. Natl. Acad. Sci. U.S.A.* 88:5232-5236, 1991; Carter, D. B. et al., *Nature* 344:633-638, 1990). IL-1ra is normally present in higher concentrations than IL-1 in plasma, and it has been suggested that IL-1ra levels are a better correlate of disease severity than IL-1 (Biasucci, L. M. et al., *Circulation* 99:2079-2084, 1999). Furthermore, there is evidence that IL-1ra is an acute phase protein (Gabay, C. et al., *J. Clin. Invest.* 99:2930-2940, 1997). The normal plasma concentration of IL-1ra is <200 pg/ml (12 pM). The plasma concentration of IL-1ra is elevated in patients with acute myocardial infarction and unstable angina that proceeded to acute myocardial infarction, death, or refractory angina (Biasucci, L. M. et al., *Circulation* 99:2079-2084, 1999; Latini, R. et al., *J.*

Cardiovasc. Pharmacol. 23:1-6, 1994). Furthermore, IL-1ra was significantly elevated in severe acute myocardial infarction as compared to uncomplicated acute myocardial infarction (Latini, R. et al., J. Cardiovasc. Pharmacol. 23:1-6, 1994). Elevations in the plasma concentration of IL-1ra are associated with any condition that involves activation of the inflammatory or acute phase response, including infection, trauma, and arthritis. IL-1ra is released into the bloodstream in pro-inflammatory conditions, and it may also be released as a participant in the acute phase response. The major sources of clearance of IL-1ra from the bloodstream appear to be kidney and liver (Kim, D. C. et al., J. Pharm. Sci. 84:575-580, 1995). IL-1ra concentrations were elevated in the plasma of individuals with unstable angina within 24 hours of onset, and these elevations may even be evident within 2 hours of onset (Biasucci, L. M. et al., Circulation 99:2079-2084, 1999). In patients with severe progression of unstable angina, the plasma concentration of IL-1ra was higher 48 hours after onset than levels at admission, while the concentration decreased in patients with uneventful progression (Biasucci, L. M. et al., Circulation 99:2079-2084, 1999). In addition, the plasma concentration of IL-1ra associated with unstable angina can approach 1.4 ng/ml (80 pM). Changes in the plasma concentration of IL-1ra appear to be related to disease severity. Furthermore, it is likely released in conjunction with or soon after IL-1 release in pro-inflammatory conditions, and it is found at higher concentrations than IL-1. This indicates that IL-1ra may be a useful indirect marker of IL-1 activity, which elicits the production of IL-6.

Interleukin-6 (IL-6) is a 20 kDa secreted protein that is a hematopoietin family proinflammatory cytokine. IL-6 is an acute-phase reactant and stimulates the synthesis of a variety of proteins, including adhesion molecules. Its major function is to mediate the acute phase production of hepatic proteins, and its synthesis is induced by the cytokine IL-1. IL-6 is normally produced by macrophages and T lymphocytes. The normal serum concentration of IL-6 is <3 pg/ml (0.15 pM). The plasma concentration of IL-6 is elevated in patients with acute myocardial infarction and unstable angina, to a greater degree in acute myocardial infarction (Biasucci, L. M. et al., Circulation 94:874-877, 1996; Manten, A. et al., Cardiovasc. Res. 40:389-395, 1998; Biasucci, L. M. et al., Circulation 99:2079-2084, 1999). IL-6 is not significantly elevated in the plasma of patients with stable angina (Biasucci, L. M. et al., Circulation 94:874-877, 1996; Manten, A. et al., Cardiovasc. Res. 40:389-395, 1998). Furthermore, IL-6 concentrations increase over 48 hours from onset in the plasma of patients with unstable angina with severe progression, but decrease in those with uneventful progression (Biasucci, L. M. et al., Circulation 99:2079-2084, 1999). This indicates that IL-6 may be a useful indicator of disease progression. Plasma elevations of IL-6 are associated with any nonspecific proinflammatory condition such as trauma, infection, or other diseases that elicit an acute phase response. IL-6 has a half-life of 4.2 hours in the bloodstream and is elevated following acute myocardial infarction and unstable angina (Manten, A. et al., Cardiovasc. Res. 40:389-395, 1998). The plasma concentration of IL-6 is elevated within 8-12 hours of acute myocardial infarction onset, and can approach 100 pg/ml. The plasma concentration of IL-6 in patients with unstable angina was elevated at peak levels 72 hours after onset, possibly due to the severity of insult (Biasucci, L. M. et al., Circulation 94:874-877, 1996).

Interleukin-8 (IL-8) is a 6.5 kDa chemokine produced by monocytes, endothelial cells, alveolar macrophages and fibroblasts. IL-8 induces chemotaxis and activation of neutrophils and T cells.

Tumor necrosis factor α (TNFα) is a 17 kDa secreted proinflammatory cytokine that is involved in the acute phase response and is a pathogenic mediator of many diseases. TNFα is normally produced by macrophages and natural killer cells. TNF-alpha is a protein of 185 amino acids glycosylated at positions 73 and 172. It is synthesized as a precursor protein of 212 amino acids. Monocytes express at least five different molecular forms of TNF-alpha with molecular masses of 21.5-28 kDa. They mainly differ by post-translational alterations such as glycosylation and phosphorylation. The normal serum concentration of TNFα is <40 pg/ml (2 pM). The plasma concentration of TNFα is elevated in patients with acute myocardial infarction, and is marginally elevated in patients with unstable angina (Li, D. et al., Am. Heart J. 137:1145-1152, 1999; Squadrito, F. et al., Inflamm. Res. 45:14-19, 1996; Latini, R. et al., J. Cardiovasc. Pharmacol. 23:1-6, 1994; Carlstedt, F. et al., J. Intern. Med. 242:361-365, 1997). Elevations in the plasma concentration of TNFα are associated with any proinflammatory condition, including trauma, stroke, and infection. TNFα has a half-life of approximately 1 hour in the bloodstream, indicating that it may be removed from the circulation soon after symptom onset. In patients with acute myocardial infarction, TNFα was elevated 4 hours after the onset of chest pain, and gradually declined to normal levels within 48 hours of onset (Li, D. et al., Am. Heart J. 137:1145-1152, 1999). The concentration of TNFα in the plasma of acute myocardial infarction patients exceeded 300 pg/ml (15 pM) (Squadrito, F. et al., Inflamm. Res. 45:14-19, 1996). Release of TNFα by monocytes has also been related to the progression of pneumoconiosis in coal workers. Schins and Borm, Occup. Environ. Med. 52:441-50 (1995).

Myeloperoxidase ("MPO") (EC 1.11.1.7) is a tetrameric glycosylated heme-containing protein of about 150 kDa. The sequence of human myeloperoxidase precursor may be obtained from Swiss-Prot accession number P05164. At least three alternative splice forms and several variant forms (e.g., 173 Y→C; 251 M→T; 569 R→W; 717 I→V; and an insert of 32 residues following N182) are known. MPO catalyzes the oxidation of an organic substrate with the concomitant reduction of hydrogen peroxide. MPO forms part of the host defense system to microbes, and is abundant in neutrophils and monocytes, and has been reported to be associated with risk in cardiovascular disease. See, e.g., U.S. 2002/0164662 A1.

Soluble intercellular adhesion molecule (sICAM-1), also called CD54, is a 85-110 kDa cell surface-bound immunoglobulin-like integrin ligand that facilitates binding of leukocytes to antigen-presenting cells and endothelial cells during leukocyte recruitment and migration. sICAM-1 is normally produced by vascular endothelium, hematopoietic stem cells and non-hematopoietic stem cells, which can be found in intestine and epidermis. sICAM-1 can be released from the cell surface during cell death or as a result of proteolytic activity. The normal plasma concentration of sICAM-1 is approximately 250 ng/ml (2.9 nM). The plasma concentration of sICAM-1 is significantly elevated in patients with acute myocardial infarction and unstable angina, but not stable angina (Pellegatta, F. et al., J. Cardiovasc. Pharmacol. 30:455-460, 1997; Miwa, K. et al., Cardiovasc. Res. 36:37-44, 1997; Ghaisas, N. K. et al., Am. J. Cardiol. 80:617-619, 1997; Ogawa, H. et al., Am. J. Cardiol. 83:38-42, 1999). Furthermore, ICAM-1 is expressed in atherosclerotic lesions and in areas predisposed to lesion formation, so it may be released into the bloodstream upon plaque rupture (Iiyama, K. et al., Circ. Res. 85:199-207, 1999; Tenaglia, A. N. et al., Am. J. Cardiol. 79:742-747, 1997). Elevations of the plasma concentration of sICAM-1 are associated with ischemic stroke, head trauma, atherosclerosis, cancer, preeclampsia, multiple sclerosis, cystic fibrosis, and other nonspecific inflammatory states (Kim, J. S., *J. Neurol. Sci.* 137:69-78, 1996; Laskowitz, D. T. et al., *J. Stroke Cerebrovasc. Dis.* 7:234-241, 1998). The plasma concentration of sICAM-1 is elevated during the acute stage of acute myocardial infarction and unstable angina. The elevation of plasma sICAM-1 reaches its peak within 9-12 hours of acute myocardial infarction onset, and returns to normal levels within 24 hours (Pellegatta, F. et al., *J. Cardiovasc. Pharmacol.* 30:455-460, 1997). The plasma concentration of sICAM can approach 700 ng/ml (8 nM) in patients with acute myocardial infarction (Pellegatta, F. et al., *J. Cardiovasc. Pharmacol.* 30:455-460, 1997). sICAM-1 is elevated in the plasma of individuals with acute myocardial infarction and unstable angina, but it is not specific for these diseases. It may, however, be useful marker in the differentiation of acute myocardial infarction and unstable angina from stable angina since plasma elevations are not associated with stable angina. Interestingly, ICAM-1 is present in atherosclerotic plaques, and may be released into the bloodstream upon plaque rupture. Additional ICAM molecules are well known in the art, including ICAM-2 (also called CD102) and ICAM-3 (also called CD50), which may also be present in the blood.

Vascular cell adhesion molecule (VCAM), also called CD106, is a 100-110 kDa cell surface-bound immunoglobulin-like integrin ligand that facilitates binding of B lymphocytes and developing T lymphocytes to antigen-presenting cells during lymphocyte recruitment. VCAM is normally produced by endothelial cells, which line blood and lymph vessels, the heart, and other body cavities. VCAM-1 can be released from the cell surface during cell death or as a result of proteolytic activity. The normal serum concentration of sVCAM is approximately 650 ng/ml (6.5 nM). The plasma concentration of sVCAM-1 is marginally elevated in patients with acute myocardial infarction, unstable angina, and stable angina (Mulvihill, N. et al., *Am. J. Cardiol.* 83:1265-7, A9, 1999; Ghaisas, N. K. et al., *Am. J. Cardiol.* 80:617-619, 1997). However, sVCAM-1 is expressed in atherosclerotic lesions and its plasma concentration may correlate with the extent of atherosclerosis (Iiyama, K. et al., *Circ. Res.* 85:199-207, 1999; Peter, K. et al., *Arterioscler. Thromb. Vasc. Biol.* 17:505-512, 1997). Elevations in the plasma concentration of sVCAM-1 are associated with ischemic stroke, cancer, diabetes, preeclampsia, vascular injury, and other nonspecific inflammatory states (Bitsch, A. et al., *Stroke* 29:2129-2135, 1998; Otsuki, M. et al., *Diabetes* 46:2096-2101, 1997; Banks, R. E. et al., *Br. J. Cancer* 68:122-124, 1993; Steiner, M. et al., *Thromb. Haemost.* 72:979-984, 1994; Austgulen, R. et al., *Eur. J. Obstet. Gynecol. Reprod. Biol.* 71:53-58, 1997).

Monocyte chemotactic protein-1 (MCP-1) is a 10 kDa chemotactic factor that attracts monocytes and basophils, but not neutrophils or eosiniphils. MCP-1 is normally found in equilibrium between a monomeric and homodimeric form, and it is normally produced in and secreted by monocytes and vascular endothelial cells (Yoshimura, T. et al., *FEBS Lett.* 244:487-493, 1989; Li, Y.S. et al., *Mol. Cell. Biochem.* 126: 61-68, 1993). MCP-1 has been implicated in the pathogenesis of a variety of diseases that involve monocyte infiltration, including psoriasis, rheumatoid arthritis, and atherosclerosis. The normal concentration of MCP-1 in plasma is <0.1 ng/ml. The plasma concentration of MCP-1 is elevated in patients with acute myocardial infarction, and may be elevated in the plasma of patients with unstable angina, but no elevations are associated with stable angina (Soejima, H. et al., *J. Am. Coll. Cardiol.* 34:983-988, 1999; Nishiyama, K. et al., *Jpn. Circ. J.* 62:710-712, 1998; Matsumori, A. et al., *J. Mol. Cell. Cardiol.* 29:419-423, 1997). Interestingly, MCP-1 also may be involved in the recruitment of monocytes into the arterial wall during atherosclerosis. Elevations of the serum concentration of MCP-1 are associated with various conditions associated with inflammation, including alcoholic liver disease, interstitial lung disease, sepsis, and systemic lupus erythematosus (Fisher, N. C. et al., *Gut* 45:416-420, 1999; Suga, M. et al., *Eur. Respir. J.* 14:376-382, 1999; Bossink, A. W. et al., *Blood* 86:3841-3847, 1995; Kaneko, H. et al. *J. Rheumatol.* 26:568-573, 1999). MCP-1 is released into the bloodstream upon activation of monocytes and endothelial cells. The concentration of MCP-1 in plasma form patients with acute myocardial infarction has been reported to approach 1 ng/ml (100 pM), and can remain elevated for one month (Soejima, H. et al., *J. Am. Coll. Cardiol.* 34:983-988, 1999). MCP-1 is a specific marker of the presence of a pro-inflammatory condition that involves monocyte migration.

Macrophage migration inhibitory factor (MIF) is a lymphokine involved in cell-mediated immunity, immunoregulation, and inflammation. It plays a role in the regulation of macrophage function in host defense through the suppression of anti-inflammatory effects of glucocorticoids. Monocytes and macrophages are reported to be a significant source of MIF after stimulation with endotoxin (lipopolysaccharide, or LPS) or with the cytokines tumor necrosis factor $\alpha$ (TNF$\alpha$) and interferon-$\gamma$ (IFN$\gamma$). MIF also was described to mediate certain pro-inflammatory effects, stimulating macrophages to produce TNF$\alpha$ and nitric oxide when given in combination with IFN$\gamma$ (8, 9). Like TNF$\alpha$ and IL-1$\beta$, MIF plays a central role in the host response to endotoxemia. Coinjection of recombinant MIF and LPS exacerbates LPS lethality, whereas neutralizing anti-MIF antibodies fully protect mice from endotoxic shock.

Receptor for advanced glycation end products ("RAGE", human sequence: Swiss-Prot Q15109) mediates the effects of various nonenzymatically glycosylated proteins (advanced glycation end products, or AGEs) that accumulate in vascular tissues under certain conditions such as diabetes and age-related disorders such as Alzheimer's disease. There are soluble variants, including two resulting from alternative splicing events. RAGE overexpression has been reported to be associated with inflammatory responses that contribute to atherosclerotic plaque destabilization. See, e.g., Cipollone et al., *Circulation* 108: 1070-77, 2003.

Hemoglobin (Hb) is an oxygen-carrying iron-containing globular protein found in erythrocytes. It is a heterodimer of two globin subunits. $\alpha_2\gamma_2$ is referred to as fetal Hb, $\alpha_2\beta_2$ is called adult HbA, and $\alpha_2\delta_2$ is called adult HbA$_2$. 90-95% of hemoglobin is HbA, and the $\alpha_2$ globin chain is found in all Hb types, even sickle cell hemoglobin. Hb is responsible for carrying oxygen to cells throughout the body. Hb$\alpha_2$ is not normally detected in serum.

Human lipocalin-type prostaglandin D synthase (hPDGS), also called $\beta$-trace, is a 30 kDa glycoprotein that catalyzes the formation of prostaglandin D2 from prostaglandin H. The upper limit of hPDGS concentrations in apparently healthy individuals is reported to be approximately 420 ng/ml (Patent No. EP0999447A1). Elevations of hPDGS have been identified in blood from patients with unstable angina and cerebral infarction (Patent No. EP0999447A1). Furthermore, hPDGS appears to be a useful marker of ischemic episodes, and concentrations of hPDGS were found to decrease over time in a patient with angina pectoris following percutaneous transluminal coronary angioplasty (PTCA), suggesting that the hPGDS concentration decreases as ischemia is resolved (Patent No. EP0999447A1).

Mast cell tryptase, also known as alpha tryptase, is a 275 amino acid (30.7 kDa) protein that is the major neutral protease present in mast cells. Mast cell tryptase is a specific marker for mast cell activation, and is a marker of allergic airway inflammation in asthma and in allergic reactions to a diverse set of allergens. See, e.g., Taira et al., *J. Asthma* 39: 315-22 (2002); Schwartz et al., *N. Engl. J. Med.* 316: 1622-26 (1987). Elevated serum tryptase levels (>1 ng/mL) between 1 and 6 hours after an event provides a specific indication of mast cell degranulation.

Eosinophil cationic protein (ECP) is a heterogeneous protein with molecular weight variants from 16-24 kDa and a pI of pH 10.8. ECP is highly cytotoxic and is released by activated eosinophils. Venge, *Clinical and experimental allergy*, 23 (suppl. 2): 3-7 (1993). Concentrations of ECP in the bronchoalveolar lavage fluid (BALF) of asthma patients vary with the severity of their disease, and ECP concentrations in sputum have also been shown to reflect the pathophysiology of the disease. Bousquet et al., *New Engl. J Med.* 323: 1033-9 (1990). Virchow et al., *Am. Rev. Respir. Dis.* 146: 604-6 (1992). Assessment of serum ECP may be assumed to reflect pulmonary inflammation in bronchial asthma. Koller et al., *Arch. Dis. Childhood* 73: 413-7 (1995); see also, Sorkness et al., *Clin. Exp. Allergy* 32: 1355-59 (2002); Badr-elDin et al., East Mediterr. Health J. 5: 664-75 (1999).

KL-6 (also referred to as MUC1) is a high molecular weight (>300 kDa) mucinous glycoprotein expressed on pneumonocytes. Serum levels of KL-6 are reportedly elevated in interstitial lung diseases, which are characterized by exertional dyspnea. KL-6 has been shown to be a marker of various interstitial lung diseases, including pulmonary fibrosis, interstitial pneumonia, sarcoidosis, and interstitial pneumonitis. See, e.g., Kobayashi and Kitamura, *Chest* 108: 311-15 (1995); Kohno, *J. Med. Invest.* 46: 151-58 (1999); Bandoh et al., *Ann. Rheum. Dis.* 59: 257-62 (2000); and Yamane et al., *J. Rheumatol.* 27: 930-4 (2000).

Interleukin 10 ("IL-10") is a 160 amino acid (18.5 kDa predicted mass) cytokine that is a member of the four α-helix bundle family of cytokines. In solution, IL-10 forms a homodimer having an apparent molecular weight of 39 kDa. The human IL-10 gene is located on chromosome 1. Viera et al., *Proc. Natl. Acad Sci. USA* 88: 1172-76 (1991); Kim et al., J. Immunol. 148: 3618-23 (1992). Overproduction of IL-10 has been identified as a marker in sepsis, and is predictive of severity and mortality. Gogos et al., *J. Infect. Dis.* 181: 176-80 (2000).

The term "nitrotyrosine" as used herein refers to the modification of tyrosine residues in proteins to create 3-nitro-L-tyrosine residues. Peroxynitrite reacts with the phenolic ring of tyrosine residues in proteins to create this stable adduct. Measurement of nitrotyrosine in samples may be performed as a competitive assay using a single antibody specific for the modification. Alternatively, sandwich assays may use a first antibody that binds to the modified tyrosine residues and a second antibody specific for a protein of interest (e.g., albumin) to identify the nitrated forms of the protein. In certain embodiments, a sandwich may be formed in which both the first and second antibodies bind to the modified tyrosine residues. Such assays will measure proteins comprising at least two modified residues. The formation of peroxynitrite has been reported to be associated with inflammatory states, and with certain neurologic and cardiovascular disorders. See, e.g., Kuhn et al., *J. Neurochem.* 89: 529-36, 2004; Shishehbor et al., *JAMA* 289: 1675-80, 2003; Kooy et al., *Crit. Care. Med.* 25: 812-19, 1997.

(v) Exemplary Specific Markers for Neural Tissue Injury

Adenylate kinase (AK) is a ubiquitous 22 kDa cytosolic enzyme that catalyzes the interconversion of ATP and AMP to ADP. Four isoforms of adenylate kinase have been identified in mammalian tissues (Yoneda, T. et al., *Brain Res Mol Brain Res* 62:187-195, 1998). The AK1 isoform is found in brain, skeletal muscle, heart, and aorta. The normal serum mass concentration of AK1 is currently unknown, because a functional assay is typically used to measure total AK concentration. The normal serum AK concentration is <5 units/liter and AK elevations have been performed using CSF (Bollensen, E. et al., *Acta Neurol Scand* 79:53-582, 1989). Serum AK1 appears to have the greatest specificity of the AK isoforms as a marker of neural tissue injury. AK may be best suited as a cerebrospinal fluid marker of cerebral ischemia, where its dominant source would be neural tissue.

β-Chimerin (also known as "β-Chimaerin" and "chimerin-2", human sequence Swiss-Prot P52757) is reported to be a non-protein kinase C phorbol ester receptor. See, e.g., Caloca et al., *Proc. Natl. Acad. Sci. USA* 96: 11854-59, 1999. Two forms, β-2-chimerin and β-1-chimerin, are formed by alternative splicing events. β-Chimerin is expressed at highest levels in the brain and pancreas, with reduced expression seen in the heart, kidney and liver.

Neurotrophins are a family of growth factors expressed in the mammalian nervous system. Some examples include nerve growth factor (NGF), brain-derived neurotrophic factor (BDNF), neurotrophin-3 (NT-3) and neurotrophin-4/5 (NT-4/5). Neurotrophins exert their effects primarily as target-derived paracrine or autocrine neurotrophic factors. The role of the neurotrophins in survival, differentiation and maintenance of neurons is well known. They exhibit partially overlapping but distinct patterns of expression and cellular targets. In addition to the effects in the central nervous system, neurotrophins also affect peripheral afferent and efferent neurons.

Nogo receptor (also known as "reticulon 4 receptor," human sequence Swiss-Prot Q9BZR6) is a receptor that mediates the function of reticulon 4 (also known as "neurite outgrowth inhibitor" and "Nogo protein") and oligodendrocyte-myelin glycoprotein. The receptor is attached to the cell membrane via a GPI anchor, and soluble forms circulate as a result of cleavage of this anchor linkage. Nogo receptor contains 9 "leucine rich repeats." It is expressed primarily in the brain, with highest levels present in the grey matter. Lower levels of expression are seen in heart and kidney.

BDNF is a potent neurotrophic factor which supports the growth and survivability of nerve and/or glial cells. BDNF is expressed as a 32 kDa precursor "pro-BDNF" molecule that is cleaved to a mature BDNF form. Mowla et al., J. Biol. Chem. 276: 12660-6 (2001). The most abundant active form of human BDNF is a 27 kDa homodimer, formed by two identical 119 amino acid subunits, which is held together by strong hydrophobic interactions; however, pro-BDNF is also released extracellularly and is biologically active. BDNF is widely distributed throughout the CNS and displays in vitro trophic effects on a wide range of neuronal cells, including hippocampal, cerebellar, and cortical neurons. In vivo, BDNF has been found to rescue neural cells from traumatic and toxic brain injury. For example, studies have shown that after transient middle cerebral artery occlusion, BDNF mRNA is upregulated in cortical neurons (Schabiltz et al., *J. Cereb. Blood Flow Metab.* 14:500-506, 1997). In experimentally induced focal, unilateral thrombotic stroke, BDNF mRNA was increased from 2 to 18 h following the stroke. Such results suggest that BDNF potentially plays a neuroprotective role in focal cerebral ischemia.

NT-3 is also a 27 kDa homodimer consisting of two 119-amino acid subunits. The addition of NT-3 to primary cortical cell cultures has been shown to exacerbate neuronal death caused by oxygen-glucose deprivation, possible via oxygen free radical mechanisms (Bates et al., *Neurobiol. Dis.* 9:24-37, 2002). NT-3 is expressed as an inactive pro-NT-3 molecule, which is cleaved to the mature biologically active form.

Calbindin-D is a 28 kDa cytosolic vitamin D-dependent $Ca^{2+}$-binding protein that may serve a cellular protective function by stabilizing intracellular calcium levels. Calbindin-D is found in the central nervous system, mainly in glial cells, and in cells of the distal renal tubule (Hasegawa, S. et al., *J. Urol.* 149:1414-1418, 1993). The normal serum concentration of calbindin-D is <20 pg/ml (0.7 pM). Serum calbindin-D concentration is reportedly elevated following cardiac arrest, and this elevation is thought to be a result of CNS damage due to cerebral ischemia (Usui, A. et al., *J. Neurol. Sci.* 123:134-139, 1994). Elevations of serum calbindin-D are elevated and plateau soon after reperfusion following ischemia. Maximum serum calbindin-D concentrations can be as much as 700 pg/ml (25 pM).

Creatine kinase (CK) is a cytosolic enzyme that catalyzes the reversible formation of ADP and phosphocreatine from ATP and creatine. The brain-specific CK isoform (CK-BB) is an 85 kDa cytosolic protein that accounts for approximately 95% of the total brain CK activity. It is also present in significant quantities in cardiac tissue, intestine, prostate, rectum, stomach, smooth muscle, thyroid uterus, urinary bladder, and veins (Johnsson, P. J., *Cardiothorac. Vasc. Anesth.* 10:120-126, 1996). The normal serum concentration of CK-BB is <10 ng/ml (120 pM). Serum CK-BB is elevated after hypoxic and ischemic brain injury, but a further investigation is needed to identify serum elevations in specific stroke types (Laskowitz, D.T. et al., *J. Stroke Cerebrovasc. Dis.* 7:234-241, 1998). Elevations of CK-BB in serum can be attributed to neural tissue injury due to ischemia, coupled with increased permeability of the blood brain barrier. No correlation of the serum concentration of CK-BB with the extent of damage (infarct volume) or neurological outcome has been established. CK-BB has a half-life of 1-5 hours in serum and is normally detected in serum at a concentration of <10 ng/ml (120 pM). In severe stroke, serum concentrations CK-BB are elevated and peak soon after the onset of stroke (within 24 hours), gradually returning to normal after 3-7 days (4). CK-BB concentrations in the serum of individuals with head injury peak soon after injury and return to normal between 3.5-12 hours after injury, depending on the injury severity (Skogseid, I. M. et al., *Acta Neurochir. (Wien.)* 115:106-111, 1992). Maximum serum CK-BB concentrations can exceed 250 ng/ml (3 nM). CK-BB may be best suited as a CSF marker of cerebral ischemia, where its dominant source would be neural tissue. CKBB might be more suitable as a serum marker of CNS damage after head injury because it is elevated for a short time in these individuals, with its removal apparently dependent upon the severity of damage.

Glial fibrillary acidic protein (GFAP) is a 55 kDa cytosolic protein that is a major structural component of astroglial filaments and is the major intermediate filament protein in astrocytes. GFAP is specific to astrocytes, which are interstitial cells located in the CNS and can be found near the blood-brain barrier. GFAP is not normally detected in serum. Serum GFAP is elevated following ischemic stroke (Niebroj-Dobosz, I., et al., *Folia Neuropathol.* 32:129-137, 1994). Current reports investigating serum GFAP elevations associated with stroke are severely limited, and much further investigation is needed to establish GFAP as a serum marker for all stroke types. Most studies investigating GFAP as a stroke marker have been performed using cerebrospinal fluid. Elevations of GFAP in serum can be attributed to neural tissue injury due to ischemia, coupled with increased permeability of the blood brain barrier. No correlation of the serum concentration of GFAP with the extent of damage (infarct volume) or neurological outcome has been established. GFAP is elevated in cerebrospinal fluid of individuals with various neuropathies affecting the CNS, but there are no reports currently available describing the release of GFAP into the serum of individuals with diseases other than stroke (Albrechtsen, M. and Bock, E. J., *Neuroimmunol.* 8:301-309, 1985). Serum concentrations GFAP appear to be elevated soon after the onset of stroke, continuously increase and persist for an amount of time (weeks) that may correlate with the severity of damage. GFAP appears to a very specific marker for severe CNS injury, specifically, injury to astrocytes due to cell death caused by ischemia or physical damage.

Lactate dehydrogenase (LDH) is a ubiquitous 135 kDa cytosolic enzyme. It is a tetramer of A and B chains that catalyzes the reduction of pyruvate by NADH to lactate. Five isoforms of LDH have been identified in mammalian tissues, and the tissue-specific isoforms are made of different combinations of A and B chains. The normal serum mass concentration of LDH is currently unknown, because a functional assay is typically used to measure total LDH concentration. The normal serum LDH concentration is <600 units/liter (Ray, P. et al., *Cancer Detect. Prev.* 22:293-304, 1998). A great majority of investigations into LDH elevations in the context of stroke have been performed using cerebrospinal fluid, and elevations correlate with the severity of injury. Elevations in serum LDH activity are reported following both ischemic and hemorrhagic stroke, but further studies are needed in serum to confirm this observation and to determine a correlation with the severity of injury and neurological outcome (Aggarwal, S. P. et al., *J. indian Med. Assoc.* 93:331-332, 1995; Maiuri, F. et al., *Neurol. Res.* 11:6-8, 1989). LDH may be best suited as a cerebrospinal fluid marker of cerebral ischemia, where its dominant source would be neural tissue.

Myelin basic protein (MBP) is actually a 14-21 kDa family of cytosolic proteins generated by alternative splicing of a single MBP gene that is likely involved in myelin compaction around axons during the myelination process. MBP is specific to oligodendrocytes in the CNS and in Schwann cells of the peripheral nervous system (PNS). It accounts for approximately 30% of the total myelin protein in the CNS and approximately 10% of the total myelin protein in the PNS. The normal serum concentration of MBP is <7 ng/ml (400 pM). Serum MBP is elevated after all types of severe stroke, specifically thrombotic stroke, embolic stroke, intracerebral hemorrhage, and subarachnoid hemorrhage, while elevations in MBP concentration are not reported in the serum of individuals with strokes of minor to moderate severity, which would include lacunar infarcts or transient ischemic attacks (Palfreyman, J. W. et al., *Clin. Chim. Acta* 92:403-409, 1979). Elevations of MBP in serum can be attributed to neural tissue injury due to physical damage or ischemia caused by infarction or cerebral hemorrhage, coupled with increased permeability of the blood brain barrier. The serum concentration of MBP has been reported to correlate with the extent of damage (infarct volume), and it may also correlate with neurological outcome. The amount of available information regarding serum MBP elevations associated with stroke is limited, because most investigations have been performed using cerebrospinal fluid. MBP is normally detected in serum at an upper limit of 7 ng/ml (400 pM), is elevated after severe stroke and neural tissue injury. Serum MBP is thought to be elevated within hours after stroke onset, with concentrations increasing to a maximum level within 2-5 days after onset. After the serum concentration reaches its maximum, which can exceed 120 ng/ml (6.9 nM), it can take over one week to gradually decrease to normal concentrations. Because the severity of damage has a direct effect on the release of MBP, it will affect the release kinetics by influencing the length of time that MBP is elevated in the serum. MBP will be present in the serum for a longer period of time as the severity of injury increases. The release of MBP into the serum of patients with head injury is thought to follow similar kinetics as those described for stroke, except that serum MBP concentrations reportedly correlate with the neurological outcome of individuals with head injury (Thomas, D. G. et al., *Acta Neurochir. Suppl.* (*Wien*) 28:93-95, 1979). The release of MBP into the serum of patients with intracranial tumors is thought to be persistent, but still needs investigation. Finally, serum MBP concentrations can sometimes be elevated in individuals with demyelinating diseases, but no conclusive investigations have been reported. As reported in individuals with multiple sclerosis, MBP is frequently elevated in the cerebrospinal fluid, but matched elevations in serum are often not present (Jacque, C. et al., *Arch. Neurol.* 39:557-560, 1982). This could indicate that cerebral damage has to be accompanied by an increase in the permeability of the blood-brain barrier to result in elevation of serum MBP concentrations. However, MBP can also be elevated in the population of individuals having intracranial tumors. The presence of these individuals in the larger population of individuals that would be candidates for an assay using this marker for stroke is rare. These individuals, in combination with individuals undergoing neurosurgical procedures or with demyelinating diseases, would nonetheless have an impact on determining the specificity of MBP for neural tissue injury. Additionally, serum MBP may be useful as a marker of severe stroke, potentially identifying individuals that would not benefit from stroke therapies and treatments, such as tPA administration.

Neural cell adhesion molecule (NCAM), also called CD56, is a 170 kDa cell surface-bound immunoglobulin-like integrin ligand that is involved in the maintenance of neuronal and glial cell interactions in the nervous system, where it is expressed on the surface of astrocytes, oligodendrocytes, Schwann cells, neurons, and axons. NCAM is also localized to developing skeletal muscle myotubes, and its expression is upregulated in skeletal muscle during development, denervation and renervation. The normal serum mass concentration of NCAM has not been reported. NCAM is commonly measured by a functional enzyme immunoassay and is reported to have a normal serum concentration of <20 units/ml. Changes in serum NCAM concentrations specifically related to stroke have not been reported. NCAM may be best suited as a CSF marker of cerebral ischemia, where its dominant source would be neural tissue.

RNA-binding protein regulatory subunit ("RNA-BP," also known as "DJ-1," human sequences Swiss-Prot O14805 and Q99497) was first identified as a gene that resulted in a transformed phenotype when cotransfected with H-ras or c-myc. Mutation of RNA-BP are reported to correlate with the PARK7 form of early onset Parkinson's disease. Although the molecular effect of RNA-BP remains unproven, it is believed to be linked to responses to oxidative stress. See, e.g., Tao and Tong, *J. Biol. Chem.* 278: 31372-79, 2003; Taira et al., *EMBO Rep.* 5: 213-18, 2004.

Enolase is a 78 kDa homo- or heterodimeric cytosolic protein produced from α, β, and γ subunits. It catalyzes the interconversion of 2-phosphoglycerate and phosphoenolpyruvate in the glycolytic pathway. Enolase can be present as αα, ββ, αγ, and γγ isoforms. The α subunit is found in glial cells and most other tissues, the β subunit is found in muscle tissue, and the γ subunit if found mainly in neuronal and neuroendocrine cells (Quinn, G. B. et al., *Clin. Chem.* 40:790-795, 1994). The γγ enolase isoform is most specific for neurons, and is referred to as neuron-specific enolase (NSE). NSE, found predominantly in neurons and neuroendocrine cells, is also present in platelets and erythrocytes. The normal serum concentration of NSE is <12.5 ng/ml (160 pM).

NSE is made up of two subunits; thus, the most feasible immunological assay used to detect NSE concentrations would be one that is directed against one of the subunits. In this case, the γ subunit would be the ideal choice. However, the γ subunit alone is not as specific for cerebral tissue as the γγ isoform, since a measurement of the γ subunit alone would detect both the αγ and γγ isoforms. In this regard, the best immunoassay for NSE would be a two-site assay that could specifically detect the γγ isoform. Serum NSE is reportedly elevated after all stroke types, including TIAs, which are cerebral in origin and are thought to predispose an individual to having a more severe stroke at a later date (Isgro, F. et al., *Eur. J. Cardiothorac. Surg.* 11:640-644, 1997). Elevations of NSE in serum can be attributed to neural tissue injury due to physical damage or ischemia caused by infarction or cerebral hemorrhage, coupled with increased permeability of the blood brain barrier, and the serum concentration of NSE has been reported to correlate with the extent of damage (infarct volume) and neurological outcome (Martens, P. et al., *Stroke* 29:2363-2366, 1998). Additionally, a secondary elevation of serum NSE concentration may be an indicator of delayed neuronal injury resulting from cerebral vasospasm (Laskowitz, D.T. et al., *J. Stroke Cerebrovasc. Dis.* 7, 234-241, 1998). NSE, which has a biological half-life of 48 hours and is normally detected in serum at an upper limit of 12.5 ng/ml (160 pM), is elevated after stroke and neural tissue injury. Serum NSE is elevated after 4 hours from stroke onset, with concentrations reaching a maximum 1-3 days after onset (Missler, U. et al., *Stroke* 28:1956-1960, 1997). After the serum concentration reaches its maximum, which can exceed 300 ng/ml (3.9 nM), it gradually decreases to normal concentrations over approximately one week. Because the severity of damage has a direct effect on the release of NSE, it will affect the release kinetics by influencing the length of time that NSE is elevated in the serum. NSE will be present in the serum for a longer period of time as the severity of injury increases.

The release of NSE into the serum of patients with head injury follows different kinetics as seen with stroke, with the maximum serum concentration being reached within 1-6 hours after injury, often returning to baseline within 24 hours (Skogseid, I. M. et al., *Acta Neurochir.* (*Wien.*) 115:106-111, 1992). NSE is a specific marker for neural tissue injury, specifically, injury to neuronal cells due to cell death caused by ischemia or physical damage. Neurons are about 10-fold less abundant in the brain than glial cells, so any neural tissue injury coupled with increased permeability of the blood-brain barrier will have to occur in a region that has a significant regional population of neurons to significantly increase the serum NSE concentration. In addition, elevated serum concentrations of NSE can also indicate complications related to neural tissue injury after AMI and cardiac surgery. Elevations in the serum concentration of NSE correlate with the severity of damage and the neurological outcome of the individual. NSE can be used as a marker of all stroke types, including TIAs.

Proteolipid protein (PLP) is a 30 kDa integral membrane protein that is a major structural component of CNS myelin. PLP is specific to oligodendrocytes in the CNS and accounts for approximately 50% of the total CNS myelin protein in the central sheath, although extremely low levels of PLP have been found (<1%) in peripheral nervous system (PNS) myelin. The normal serum concentration of PLP is <9 ng/ml (300 pM). Serum PLP is elevated after cerebral infarction, but not after transient ischemic attack (Trotter, J. L. et al., *Ann. Neurol.* 14:554-558, 1983). Current reports investigating serum PLP elevations associated with stroke are severely limited. Elevations of PLP in serum can be attributed to neural tissue injury due to physical damage or ischemia caused by infarction or cerebral hemorrhage, coupled with increased permeability of the blood brain barrier. Correlation of the serum concentration of PLP with the extent of damage (infarct volume) or neurological outcome has not been established. No investigations examining the release kinetics of PLP into serum and its subsequent removal have been reported, but maximum concentrations approaching 60 ng/ml (2 nM) have been reported in encephalitis patients, which nearly doubles the concentrations found following stroke. PLP appears to a very specific marker for severe CNS injury, specifically, injury to oligodendrocytes. The available information relating PLP serum elevations and stroke is severely limited. PLP is also elevated in the serum of individuals with various neuropathies affecting the CNS. The undiagnosed presence of these individuals in the larger population of individuals that would be candidates for an assay using this marker for stroke is rare.

S-100 is a 21 kDa homo- or heterodimeric cytosolic $Ca^{2+}$-binding protein produced from α and β subunits. It is thought to participate in the activation of cellular processes along the Ca2+-dependent signal transduction pathway (Bonfrer, J. M. et al., *Br. J. Cancer* 77:2210-2214, 1998). S-100ao (αα isoform) is found in striated muscles, heart and kidney, S-100a (αβ isoform) is found in glial cells, but not in Schwann cells, and S-100b (ββ isoform) is found in high concentrations in glial cells and Schwann cells, where it is a major cytosolic component. The β subunit is specific to the nervous system, predominantly the CNS, under normal physiological conditions and, in fact, accounts for approximately 96% of the total S-100 protein found in the brain (Jensen, R. et al., *J. Neurochem.* 45:700-705, 1985). In addition, S-100β can be found in tumors of neuroendocrine origin, such as gliomas, melanomas, Schwannomas, neurofibromas, and highly differentiated neuroblastomas, like ganglioneuroblastoma and ganglioneuroma (Persson, L. et al., *Stroke* 18:911-918, 1987). The normal serum concentration of S-100β is <0.2 ng/ml (19 pM), which is the detection limit of the immunological detection assays used. Serum S-100β is elevated after all stroke types, including TIAs. Elevations of S-100β in serum can be attributed to neural tissue injury due to physical damage or ischemia caused by infarction or cerebral hemorrhage, coupled with increased permeability of the blood-brain barrier, and the serum concentration of S-100b has been shown to correlate with the extent of damage (infarct volume) and neurological outcome (Martens, P. et al., *Stroke* 29:2363-2366, 1998; Missler, U. et al., *Stroke* 28:1956-1960, 1997).

S-100β has a biological half-life of 2 hours and is not normally detected in serum, but is elevated after stroke and neural tissue injury. Serum S-100β is elevated after 4 hours from stroke onset, with concentrations reaching a maximum 2-3 days after onset. After the serum concentration reaches its maximum, which can approach 20 ng/ml (1.9 mM), it gradually decreases to normal over approximately one week. Because the severity of damage has a direct effect on the release of S-100b, it will affect the release kinetics by influencing the length of time that S-100b is elevated in the serum. S-100b will be present in the serum for a longer period of time as the seventy of injury increases. The release of S-100b into the serum of patients with head injury seems to follow somewhat similar kinetics as reported with stroke, with the only exception being that serum S-100β can be detected within 2.5 hours of onset and the maximum serum concentration is reached approximately 1 day after onset (Woertgen, C. et al., *Acta Neurochir. (Wien)* 139:1161-1164, 1997). S-100β is a specific marker for neural tissue injury, specifically, injury to glial cells due to cell death caused by ischemia or physical damage. Glial cells are about 10 times more abundant in the brain than neurons, so any neural tissue injury coupled with increased permeability of the blood-brain barrier will likely produce elevations of serum S-100β. Furthermore, elevated serum concentrations of S-100b can indicate complications related to neural tissue injury after AMI and cardiac surgery. S-100b has been virtually undetectable in normal individuals, and elevations in its serum concentration correlate with the seventy of damage and the neurological outcome of the individual. S-100b can be used as a marker of all stroke types, including TIAs.

Thrombomodulin (TM) is a 70 kDa single chain integral membrane glycoprotein found on the surface of vascular endothelial cells. TM demonstrates anticoagulant activity by changing the substrate specificity of thrombin. The formation of a 1:1 stoichiometric complex between thrombin and TM changes thrombin function from procoagulant to anticoagulant. This change is facilitated by a change in thrombin substrate specificity that causes thrombin to activate protein C (an inactivator of factor Va and factor VIIIa), but not cleave fibrinogen or activate other coagulation factors (Davie, E. W. et al., *Biochem.* 30:10363-10370, 1991). The normal serum concentration of TM is 25-60 ng/ml (350-850 pM). Current reports describing serum TM concentration alterations following ischemic stroke are mixed, reporting no changes or significant increases (Seki, Y. et al., *Blood Coagul. Fibrinolysis* 8:391-396, 1997). Serum elevations of TM concentration reflect endothelial cell injury and would not indicate coagulation or fibrinolysis activation.

The gamma isoform of protein kinase C (PKCg) is specific for CNS tissue and is not normally found in the circulation. PKCg is activated during cerebral ischemia and is present in the ischemic penumbra at levels 2-24-fold higher than in contralateral tissue, but is not elevated in infarcted tissue (Krupinski, J. et al., *Acta Neurobiol. Exp. (Warz)* 58:13-21, 1998). In addition, animal models have identified increased levels of PKCg in the peripheral circulation of rats following middle cerebral artery occlusion (Cornell-Bell, A. et al., Pat. No. WO 01/16599 A1). Additional isoforms of PKC, beta I and beta II were found in increased levels in the infarcted core of brain tissue from patients with cerebral ischemia (Krupinski, J. et al., *Acta Neurobiol. Exp. (Warz)* 58:13-21, 1998). Furthermore, the alpha and delta isoforms of PKC (PKCa and PKCd, respectively) have been implicated in the development of vasospasm following subarachnoid hemorrhage using a canine model of hemorrhage. PKCd expression was significantly elevated in the basilar artery during the early stages of vasospasm, and PKCa was significantly elevated as vasospasm progressed (Nishizawa, S. et al., *Eur. J. Pharmacol.* 398:113-119, 2000). Therefore, it may be of benefit to measure various isoforms of PKC, either individually or in various combinations thereof, for the identification of cerebral damage, the presence of the ischemic penumbra, as well as the development and progression of cerebral vasospasm following subarachnoid hemorrhage. Ratios of PKC isoforms such as PKCg and either PKCbI, PKCbII, or both also may be of benefit in identifying a progressing stroke, where the ischemic penumbra is converted to irreversibly damaged infarcted tissue. In this regard, PKCg may be used to identify the presence and volume of the ischemic penumbra, and either PKCbI, PKCbII, or both may be used to identify the presence and volume of the infarcted core of irreversibly damaged tissue during stroke. PKCd, PKCa, and ratios of PKCd and PKCa may be useful in identifying the presence and progression of cerebral vasospasm following subarachnoid hemorrhage.

(vi) Other Non-Specific Markers for Cellular Injury

Human vascular endothelial growth factor (VEGF) is a dimeric protein, the reported activities of which include stimulation of endothelial cell growth, angiogenesis, and capillary permeability. VEGF is secreted by a variety of vascularized tissues. In an oxygen-deficient environment, vascular endothelial cells may be damaged and may not ultimately survive. However, such endothelial damage stimulates VEGF production by vascular smooth muscle cells. Vascular endothelial cells may exhibit increased survival in the presence of VEGF, an effect that is believed to be mediated by expression of Bcl-2. VEGF can exist as a variety of splice variants known as VEGF(189), VEGF(165), VEGF(164), VEGFB(155), VEGF(148), VEGF(145), and VEGF(121).

Insulin-like growth factor-1 (IGF-1) is a ubiquitous 7.5 kDa secreted protein that mediates the anabolic and somatogenic effects of growth hormone during development (1, 2). In the circulation, IGF-1 is normally bound to an IGF-binding protein that regulates IGF activity. The normal serum concentration of IGF-1 is approximately 160 ng/ml (21.3 nM). Serum IGF-1 concentrations are reported to be significantly decreased in individuals with ischemic stroke, and the magnitude of reduction appears to correlate with the severity of injury (Schwab, S. et al., *Stroke* 28:1744-1748, 1997). Decreased IGF-1 serum concentrations have been reported in individuals with trauma and massive activation of the immune system. Due to its ubiquitous expression, serum IGF-1 concentrations could also be decreased in cases of non-cerebral ischemia. Interestingly, IGF-1 serum concentrations are decreased following ischemic stroke, even though its cellular expression is upregulated in the infarct zone (Lee, W. H. and Bondy, C., *Ann. N. Y Acad. Sci.* 679:418-422, 1993). The decrease in serum concentration could reflect an increased demand for growth factors or an increased metabolic clearance rate. Serum levels were significantly decreased 24 hours after stroke onset, and remained decreased for over 10 days (Schwab, S. et al., *Stroke* 28:1744-1748, 1997). Serum IGF-1 may be a sensitive indicator of neural tissue injury. However, the ubiquitous expression pattern of IGF-1 indicates that all tissues can potentially affect serum concentrations of IGF-1, compromising the specificity of any assay using IGF-1 as a marker for stroke. In this regard, IGF-1 may be best suited as a cerebrospinal fluid marker of cerebral ischemia, where its dominant source would be neural tissue.

Adhesion molecules are involved in the inflammatory response can also be considered as acute phase reactants, as their expression levels are altered as a result of insult. Examples of such adhesion molecules include E-selectin, intercellular adhesion molecule-1, vascular cell adhesion molecule, and the like.

E-selectin, also called ELAM-1 and CD62E, is a 140 kDa cell surface C-type lectin expressed on endothelial cells in response to IL-1 and TNFα that mediates the "rolling" interaction of neutrophils with endothelial cells during neutrophil recruitment. The normal serum concentration of E-selectin is approximately 50 ng/ml (2.9 nM). Investigations into the changes on serum E-selectin concentrations following stroke have reported mixed results. Some investigations report increases in serum E-selectin concentration following ischemic stroke, while others find it unchanged (Bitsch, A. et al., *Stroke* 29:2129-2135, 1998; Kim, J. S., *J. Neurol. Sci.* 137:69-78, 1996; Shyu, K. G. et al., *J. Neurol.* 244:90-93, 1997). E-selectin concentrations are elevated in the CSF of individuals with subarachnoid hemorrhage and may predict vasospasm (Polin, R. S. et al., *J. Neurosurg.* 89:559-567, 1998). Elevations in the serum concentration of E-selectin would indicate immune system activation. Serum E-selectin concentrations are elevated in individuals with, atherosclerosis, various forms of cancer, preeclampsia, diabetes, cystic fibrosis, AMI, and other nonspecific inflammatory states (Hwang, S. J. et al., *Circulation* 96:4219-4225, 1997; Banks, R. E. et al., *Br. J. Cancer* 68:122-124, 1993; Austgulen, R. et al., *Eur. J. Obstet. Gynecol. Reprod. Biol.* 71:53-58, 1997; Steiner, M. et al., *Thromb. Haemost.* 72:979-984, 1994; De Rose, V. et al., *Am. J. Respir. Crit. Care Med.* 157:1234-1239, 1998). The serum concentration of E-selectin may be elevated following ischemic stroke, but it is not clear if these changes are transient or regulated by an as yet unidentified mechanism. Serum E-selectin may be a specific marker of endothelial cell injury. It is not, however, a specific marker for stroke or neural tissue injury, since it is elevated in the serum of individuals with various conditions causing the generation of an inflammatory state. Furthermore, elevation of serum E-selectin concentration is associated with some of the risk factors associated with stroke.

Head activator (HA) is an 11 amino acid, 1.1 kDa neuropeptide that is found in the hypothalamus and intestine. It was originally found in the freshwater coelenterate hydra, where it acts as a head-specific growth and differentiation factor. In humans, it is thought to be a growth regulating agent during brain development. The normal serum HA concentration is <0.1 ng/ml (100 pM) Serum HA concentration is persistently elevated in individuals with tumors of neural or neuroendocrine origin (Schaller, H. C. et al., *J. Neurooncol.* 6:251-258, 1988; Winnikes, M. et al., *Eur. J. Cancer* 28:421-424, 1992). No studies have been reported regarding HA serum elevations associated with stroke. HA is presumed to be continually secreted by tumors of neural or neuroendocrine origin, and serum concentration returns to normal following tumor removal. Serum HA concentration can exceed 6.8 ng/ml (6.8 nM) in individuals with neuroendocrine-derived tumors. The usefulness of HA as part of a stroke panel would be to identify individuals with tumors of neural or neuroendocrine origin. These individuals may have serum elevations of markers associated with neural tissue injury as a result of cancer, not neural tissue injury related to stroke. Although these individuals may be a small subset of the group of individuals that would benefit from a rapid diagnostic of neural tissue injury, the use of HA as a marker would aid in their identification. Finally, angiotensin converting enzyme, a serum enzyme, has the ability to degrade HA, and blood samples would have to be drawn using EDTA as an anticoagulant to inhibit this activity.

Glycated hemoglobin HbA1c measurement provides an assessment of the degree to which blood glucose has been elevated over an extended time period, and so has been related to the extent diabetes is controlled in a patient. Glucose binds slowly to hemoglobin A, forming the A1c subtype. The reverse reaction, or decomposition, proceeds relatively slowly, so any buildup persists for roughly 4 weeks. With normal blood glucose levels, glycated hemoglobin is expected to be 4.5% to 6.7%. As blood glucose concentration rise, however, more binding occurs. Poor blood sugar control over time is suggested when the glycated hemoglobin measure exceeds 8.0%.

(vii) Markers Related to Apoptosis

Apoptosis refers to the eukaryotic "programmed cell death" pathway. The pathway is dependent upon intracellular proteases and nucleases, leading ultimately to fragmentation of genomic DNA and cell death. The following is an exemplary list of markers related to apoptosis. This list is not meant to be limiting.

Caspases are a family of proteases that relay a "doomsday" signal in a step-wise manner reminiscent of signaling by kinases. Caspases are present in all cells as latent enzymes. They are recruited to receptor-associated cytosolic complexes whose formation is initiated by receptor oligomerization (e.g., TNF receptors, FAS, and TRAIL receptors) and to other cytoplasmic adaptor proteins, such as APAF-1. Recruitment of caspases to oligomerized receptors leads to activation via dimerization or dimerization accompanied by autoproteolytic cleavage. Active caspases can proteolyze additional caspases generating a caspase cascade that cleaves proteins critical for cell survival. The final outcome of this signaling pathway is a form of controlled cell death termed apoptosis.

The subgroup of caspases involved in apoptosis has been referred to as either initiators or effectors. Caspases-8, -9, and -10 (possibly, -2 and -5) can initiate the caspase activation cascade and are therefore called initiators. Based on the prototypes, caspases-8 and -9, initiators can be activated either by dimerization alone (caspase-9) or by dimerization with concomitant autoproteolysis (caspase-8). The effector caspases-3, -6, and -7 propagate the cascade and are activated by proteolytic cleavage by other caspases. Although an initiator caspase may not be responsible for starting the caspase cascade, it can become activated and involved in later steps of the cascade. Thus, in the latter scenario, the caspase would be more appropriately termed an effector.

Members of the caspase family have several common characteristics. Caspases are present in most cells as latent forms that form homodimers during activation. They are cleaved into subunits at internal aspartates by autoproteolysis or by other caspases. Caspases are thiol-proteases that cleave at the carboxyl terminal of aspartate residues. Cleavage is specified by three or more amino acids immediately preceeding the aspartate. Additional constraints are placed on the specificity. Although many cellular proteins have the correct sequence required for caspase cleavage, only a select group are hydrolyzed. Thus, constraints on proteolysis limit hydrolysis to specific key proteins. Limitations on proteolysis results in the disassembly of the cell into membrane-limited cell fragments called apoptotic bodies. The apoptotic bodies are then engulfed and digested by phagocytic cells. It appears that limitations on proteolysis prevent the cell from lysing and releasing its contents into the surrounding environment, thereby avoiding an inflammatory response.

Caspase-3, also called CPP-32, YAMA, and apopain, is an interleukin-1β converting enzyme (ICE)-like intracellular cysteine proteinase that is activated during cellular apoptosis. Caspase-3 is present as an inactive 32 kDa precursor that is proteolytically activated during apoptosis induction into a heterodimer of 20 kDa and 11 kDa subunits (Fernandes-Alnemri, T. et al., *J. Biol. Chem.* 269:30761-30764, 1994). Its cellular substrates include poly(ADP-ribose) polymerase (PARP) and sterol regulatory element binding proteins (SREBPs) (Liu, X. et al., *J. Biol. Chem.* 271:13371-13376, 1996). The normal plasma concentration of caspase-3 is unknown. There are no published investigations into changes in the plasma concentration of caspase-3 associated with ACS. There are increasing amounts of evidence supporting the hypothesis of apoptosis induction in cardiac myocytes associated with ischemia and hypoxia (Saraste, A., *Herz* 24:189-195, 1999; Ohtsuka, T. et al., *Coron. Artery Dis.* 10:221-225, 1999; James, T. N., *Coron. Artery Dis.* 9:291-307, 1998; Bialik, S. et al., *J. Clin. Invest.* 100:1363-1372, 1997; Long, X. et al., *J. Clin. Invest.* 99:2635-2643, 1997). Elevations in the plasma caspase-3 concentration may be associated with any physiological event that involves apoptosis. There is evidence that suggests apoptosis is induced in skeletal muscle during and following exercise and in cerebral ischemia (Carraro, U. and Franceschi, C., *Aging* (*Milano*) 9:19-34, 1997; MacManus, J. P. et al., *J. Cereb. Blood Flow Metab.* 19:502-510, 1999).

Cathepsin D (E.C.3.4.23.5.) is a soluble lysosomal aspartic proteinase. It is synthesized in the endoplasmic reticulum as a preprocathepsin D. Having a mannose-6-phosphate tag, procathepsin D is recognized by a mannose-6-phosphate receptor. Upon entering into an acidic lysosome, the single-chain procathepsin D (52 KDa) is activated to cathepsin D and subsequently to a mature two-chain cathepsin D (31 and 14 KDa, respectively). The two mannose-6-phosphate receptors involved in the lysosomal targeting of procathepsin D are expressed both intracellularly and on the outer cell membrane. The glycosylation is believed to be crucial for normal intracellular trafficking. The fundamental role of cathepsin D is to degrade intracellular and internalized proteins. Cathepsin D has been suggested to take part in antigen processing and in enzymatic generation of peptide hormones. The tissue-specific function of cathepsin D seems to be connected to the processing of prolactin. Rat mammary glands use this enzyme for the formation of biologically active fragments of prolactin. Cathepsin D is functional in a wide variety of tissues during their remodeling or regression, and in apoptosis.

Brain α spectrin (also referred to as α fodrin) is a cytoskeletal protein of about 284 kDa that interacts with calmodulin in a calcium-dependent manner. Like erythroid spectrin, brain α spectrin forms oligomers (in particular dimers and tetramers). Brain α spectrin contains two EF-hand domains and 23 spectrin repeats. The caspase 3-mediated cleavage of α spectrin during apoptotic cell death may play an important role in altering membrane stability and the formation of apoptotic bodies.

Ubiquitin fusion degradation protein 1 homolog ("UFDP1H" or "UFD1L," human sequence Swiss-Prot Q92890) is a homolog of the yeast Ufd1 gene product. It is believed to be involved in the ubiquitin fusion degradation pathway and regulation of mitotic spindle disassembly. The ubiquitin-proteasome protein degradation pathway is implicated in "apoptosis-like" axonal degeneration in certain neurodegenerative diseases, but the mechanism is not well understood. See, e.g., Coleman and Ribchester, *Curr. Drug Targets CNS Neurol. Disord.* 3: 227-38, .2004. Moreover, inhibition of the ubiquitin-proteasome protein degradation pathway is reported to block degradation of certain caspases, leading to increased apoptosis. See, e.g., Kim et al., *Cell. Mol. Life Sci.* 61: 1075-81, 2004.

Nucleoside diphosphate kinase A ("NDKA," also known as nm23-H1 and granzyme A, human sequence Swiss-Prot P15531) transfers the γ-phosphate from Atp to a nucleoside diphosphate, and thus has a role in the synthesis of nucleotide triphosphates other than ATP. NDKA exists as a hexamer of A and B chains. A variant (120 S→G) is related to neuroblastoma. NDKA is reported to induce a caspase-independent cell death pathway having many of the features of apoptosis. See, e.g., Fan et al., Cell 112: 659-72, 2003.

List of Preferred Markers

The following table provides a list of preferred markers, associated with a disease or condition for which each marker can provide useful information for differential diagnosis. As understood by the skilled artisan and described herein, markers may indicate different conditions when considered with additional markers in a panel; alternatively, markers may indicate different conditions when considered in the entire clinical context of the patient.

| Marker | Classification |
| --- | --- |
| ANP | Blood pressure regulation |
| CNP | Blood pressure regulation |
| urotensin II | Blood pressure regulation |
| BNP | Blood pressure regulation |
| NT-proBNP | Blood pressure regulation |
| calcitonin gene related peptide | Blood pressure regulation |
| arg-Vasopressin | Blood pressure regulation |
| Endothelin-1 | Blood pressure regulation |
| Endothelin-2 | Blood pressure regulation |
| Endothelin-31 | Blood pressure regulation |
| procalcitonin | Blood pressure regulation |
| calcyphosine | Blood pressure regulation |
| adrenomedullin | Blood pressure regulation |
| aldosterone | Blood pressure regulation |
| angiotensin 1 | Blood pressure regulation |
| angiotensin 2 | Blood pressure regulation |
| angiotensin 3 | Blood pressure regulation |
| Bradykinin | Blood pressure regulation |
| calcitonin | Blood pressure regulation |
| Endothelin-2 | Blood pressure regulation |
| Endothelin-3 | Blood pressure regulation |
| Renin | Blood pressure regulation |
| Urodilatin | Blood pressure regulation |
| Plasmin | Coagulation and hemostasis |
| Thrombin | Coagulation and hemostasis |
| Antithrombin-III | Coagulation and hemostasis |
| Fibrinogen | Coagulation and hemostasis |
| von Willebrand factor | Coagulation and hemostasis |
| D-dimer | Coagulation and hemostasis |
| PAI-1 | Coagulation and hemostasis |
| PROTEIN C | Coagulation and hemostasis |
| TAFI | Coagulation and hemostasis |
| Fibrinopeptide A | Coagulation and hemostasis |
| Plasmin alpha 2 antiplasmin complex | Coagulation and hemostasis |
| Platelet factor 4 | Coagulation and hemostasis |
| Platelet-derived growth factor | Coagulation and hemostasis |
| P-selectin | Coagulation and hemostasis |
| Prothrombin fragment 1 + 2 | Coagulation and hemostasis |
| B-thromboglobulin | Coagulation and hemostasis |
| Thrombin antithrombin III complex | Coagulation and hemostasis |
| Thrombomodulin | Coagulation and hemostasis |
| Thrombus Precursor Protein | Coagulation and hemostasis |
| Tissue factor | Coagulation and hemostasis |
| basic calponin 1 | Vascular tissue |
| beta like 1 integrin | Vascular tissue |
| Calponin | Vascular tissue |
| CSRP2 | Vascular tissue |
| elastin | Vascular tissue |
| Fibrillin 1 | Vascular tissue |
| LTBP4 | Vascular tissue |
| smooth muscle myosin | Vascular tissue |
| transgelin | Vascular tissue |
| Carboxyterminal propeptide of type I procollagen (PICP) | Collagen synthesis |
| Collagen carboxyterminal telopeptide (ICTP) | Collagen degradation |
| Glutathione S Transferase | Inflammatory |
| HIF 1 ALPHA | Inflammatory |
| IL-10 | Inflammatory |
| IL-1-Beta | Inflammatory |
| IL-1ra | Inflammatory |
| IL-6 | Inflammatory |
| IL-8 | Inflammatory |
| Lysophosphatidic acid | Inflammatory |
| MDA-modified LDL | Inflammatory |
| Human neutrophil elastase | Inflammatory |
| C-reactive protein | Inflammatory |
| Insulin-like growth factor | Inflammatory |
| Inducible nitric oxide synthase | Inflammatory |

-continued

| Marker | Classification |
| --- | --- |
| Intracellular adhesion molecule | Inflammatory |
| Lactate dehydrogenase | Inflammatory |
| MCP-1 | Inflammatory |
| MDA-LDL | Inflammatory |
| MMP-1 | Inflammatory |
| MMP-2 | Inflammatory |
| MMP-3 | Inflammatory |
| MMP-9 | Inflammatory |
| TIMP-1 | Inflammatory |
| TIMP-2 | Inflammatory |
| TIMP-3 | Inflammatory |
| n-acetyl aspartate | Inflammatory |
| TNF Receptor Superfamily Member 1A | Inflammatory |
| Transforming growth factor beta | Inflammatory |
| Tumor necrosis factor alpha | Inflammatory |
| Vascular cell adhesion molecule | Inflammatory |
| Vascular endothelial growth factor | Inflammatory |
| cystatin C | Inflammatory |
| substance P | Inflammatory |
| Myeloperoxidase (MPO) | Inflammatory |
| macrophage inhibitory factor | Inflammatory |
| Fibronectin | Inflammatory |
| cardiotrophin 1 | Inflammatory |
| Haptoglobin | Inflammatory |
| PAPPA | Inflammatory |
| s-CD40 ligand* | Inflammatory |
| HMG | Inflammatory |
| IL-1 | Inflammatory |
| IL-2 | Inflammatory |
| IL-4 | Inflammatory |
| IL-6 | Inflammatory |
| IL-8 | Inflammatory |
| IL-10 | Inflammatory |
| IL-11 | Inflammatory |
| IL-13 | Inflammatory |
| IL-18 | Inflammatory |
| Eosinophil cationic protein | Inflammatory |
| Mast cell tryptase | Inflammatory |
| VCAM | Inflammatory |
| sICAM-1 | Inflammatory |
| TNFα | Inflammatory |
| Osteoprotegerin | Inflammatory |
| Prostaglandin D-synthase | Inflammatory |
| Prostaglandin E2 | Inflammatory |
| Receptor for advanced glycation end product (RAGE) | Inflammatory |
| RANK ligand | Inflammatory |
| Nitrotyrosine | Inflammatory |
| HSP-60 | Inflammatory |
| Serum Amyloid A | Inflammatory |
| s-iL 18 receptor | Inflammatory |
| S-iL-1 receptor | Inflammatory |
| s-TNF P55 | Inflammatory |
| s-TNF P75 | Inflammatory |
| TGF-beta | Inflammatory |
| MMP-11 | Inflammatory |
| Beta NGF | Inflammatory |
| CD44 | Inflammatory |
| EGF | Inflammatory |
| E-selectin | Inflammatory |
| Fibronectin | Inflammatory |
| MAPK10 | Neural tissue injury |
| KCNK4 | Neural tissue injury |
| KCNK9 | Neural tissue injury |
| KCNQ5 | Neural tissue injury |
| 14-3-3 | Neural tissue injury |
| 4.1B | Neural tissue injury |
| APO E4-1 | Neural tissue injury |
| myelin basic protein | Neural tissue injury |
| Atrophin 1 | Neural tissue injury |
| brain Derived neurotrophic factor | Neural tissue injury |
| Brain Fatty acid binding protein | Neural tissue injury |
| brain tubulin | Neural tissue injury |
| CACNA1A | Neural tissue injury |
| Calbindin D | Neural tissue injury |
| Calbrain | Neural tissue injury |
| Carbonic anhydrase XI | Neural tissue injury |

-continued

| Marker | Classification |
| --- | --- |
| CBLN1 | Neural tissue injury |
| Cerebellin 1 | Neural tissue injury |
| Chimerin 1 | Neural tissue injury |
| Chimerin 2 (β-chimerin) | Neural tissue injury |
| CHN1 | Neural tissue injury |
| CHN2 | Neural tissue injury |
| Ciliary neurotrophic factor | Neural tissue injury |
| CK-BB | Neural tissue injury |
| CRHR1 | Neural tissue injury |
| C-tau | Neural tissue injury |
| DRPLA | Neural tissue injury |
| GFAP | Neural tissue injury |
| GPM6B | Neural tissue injury |
| GPR7 | Neural tissue injury |
| GPR8 | Neural tissue injury |
| GRIN2C | Neural tissue injury |
| GRM7 | Neural tissue injury |
| HAPIP | Neural tissue injury |
| HIP2 | Neural tissue injury |
| LDH | Neural tissue injury |
| Myelin basic protein | Neural tissue injury |
| NCAM | Neural tissue injury |
| NT-3 | Neural tissue injury |
| NDPKA | Neural tissue injury |
| Neural cell adhesion molecule | Neural tissue injury |
| NEUROD2 | Neural tissue injury |
| Neurofiliment L | Neural tissue injury |
| Neuroglobin | Neural tissue injury |
| neuromodulin | Neural tissue injury |
| Neuron specific enolase | Neural tissue injury |
| Neuropeptide Y | Neural tissue injury |
| Neurotensin | Neural tissue injury |
| Neurotrophin 1,2,3,4 | Neural tissue injury |
| NOGO Receptor | Neural tissue injury |
| NRG2 | Neural tissue injury |
| PACE4 | Neural tissue injury |
| phosphoglycerate mutase | Neural tissue injury |
| PKC gamma | Neural tissue injury |
| proteolipid protein | Neural tissue injury |
| PTEN | Neural tissue injury |
| PTPRZ1 | Neural tissue injury |
| RGS9 | Neural tissue injury |
| RNA Binding protein Regulatory Subunit (RNA-BP, DJ-1) | Neural tissue injury |
| S-100β | Neural tissue injury |
| SCA7 | Neural tissue injury |
| secretagogin | Neural tissue injury |
| SLC1A3 | Neural tissue injury |
| SORL1 | Neural tissue injury |
| SREB3 | Neural tissue injury |
| STAC | Neural tissue injury |
| STX1A | Neural tissue injury |
| STXBP1 | Neural tissue injury |
| Syntaxin | Neural tissue injury |
| thrombomodulin | Neural tissue injury |
| transthyretin | Neural tissue injury |
| adenylate kinase-1 | Neural tissue injury |
| BDNF* | Neural tissue injury |
| neurokinin A | Neural tissue injury |
| s-acetyl Glutathione | apoptosis |
| cytochrome C | apoptosis |
| Nucleoside diphosphate kinase A (NDKA) | apoptosis |
| Caspase 3 | apoptosis |
| Cathepsin D | apoptosis |
| α-spectrin | apoptosis |
| Ubiquitin fusion degradation protein 1 homolog | apoptosis |

Ubiguitination of Markers

Ubiquitin-mediated degradation of proteins plays an important role in the control of numerous processes, such as the way in which extracellular materials are incorporated into a cell, the movement of biochemical signals from the cell membrane, and the regulation of cellular functions such as transcriptional on-off switches. The ubiquitin system has been implicated in the immune response and development. Ubiquitin is a 76-amino acid polypeptide that is conjugated to proteins targeted for degradation. The ubiquitin-protein conjugate is recognized by a 26S proteolytic complex that splits ubiquitin from the protein, which is subsequently degraded. Levels of ubiquitinated proteins generally, or of specific ubiquitin-protein conjugates or fragments thereof, can be measured as additional markers of the invention. Moreover, circulating levels of ubiquitin itself can be a useful marker in the methods described herein. See, e.g., Hu et al., *J. Cereb. Blood Flow Metab.* 21: 865-75, 2001.

The skilled artisan will recognize that an assay for ubiquitin may be designed that recognizes ubiquitin itself, ubiquitin-protein conjugates, or both ubiquitin and ubiquitin-protein conjugates. For example, antibodies used in a sandwich immunoassay may be selected so that both the solid phase antibody and the labeled antibody recognize a portion of ubiquitin that is available for binding in both unconjugated ubiquitin and ubiquitin conjugates. Alternatively, an assay specific for ubiquitin conjugates of a marker of interest could use one antibody (on a solid phase or label) that recognizes ubiquitin, and a second antibody (the other of the solid phase or label) that recognizes the marker protein.

The present invention contemplates measuring ubiquitin conjugates of any marker described herein.

Assay Measurement Strategies

Numerous methods and devices are well known to the skilled artisan for the detection and analysis of the markers of the instant invention. With regard to polypeptides or proteins in patient test samples, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing the immunoassays taught herein.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the markers is also contemplated by the present invention. The antibodies could be immobilized onto a variety of solid supports, such as magnetic or chromatographic matrix particles, the surface of an assay place (such as microtiter wells), pieces of a solid substrate material or membrane (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of markers may be carried out separately or simultaneously with one test sample. For separate or sequential assay of markers, suitable apparatuses include clinical laboratory analyzers such as the ELECSYS® (Roche), the AXSYM® (Abbott), the ACCESS® (Beckman), the ADVIA® CENTAUR® (Bayer) immunoassay systems, the NICHOLS ADVANTAGE® (Nichols Institute) immunoassay system, etc. Preferred apparatuses or protein chips perform simultaneous assays of a plurality of markers on a single surface. Particularly useful physical formats comprise surfaces having a plurality of discrete, adressable locations for the detection of a plurality of different analytes. Such formats include protein microarrays, or "protein chips" (see, e.g., Ng and Ilag, J. Cell Mol. Med. 6: 329-340 (2002)) and certain capillary devices (see e.g., U.S. Pat. No. 6,019,944). In these embodiments each discrete surface location may comprise antibodies to immobilize one or more analyte(s) (e.g., a marker) for detection at each location. Surfaces may alternatively comprise one or more discrete particles (e.g., microparticles or nanoparticles) immobilized at discrete locations of a surface, where the microparticles comprise antibodies to immobilize one analyte (e.g., a marker) for detection.

Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvageable tissue, the appropriateness of drug therapies, the effectiveness of various therapies as indicated by reperfusion or resolution of symptoms, differentiation of the various types of ACS, identification of the severity of the event, identification of the disease severity, and identification of the patient's outcome, including risk of future events.

A panel consisting of the markers referenced above may be constructed to provide relevant information related to differential diagnosis. Such a panel may be constucted using 1, 2, 3, 4, 5, 6, 7, 8, 9, 10, 15, 20, or more or individual markers. The analysis of a single marker or subsets of markers comprising a larger panel of markers could be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts (Tiete Textbook of Clinical Chemistry, $2^{Nd}$ edition, Carl Burtis and Edward Ashwood eds., W. B. Saunders and Company, p. 496).

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings.

In another embodiment, the present invention provides a kit for the analysis of markers. Such a kit preferably comprises devises and reagents for the analysis of at least one test sample and instructions for performing the assay. Optionally the kits may contain one or more means for using information obtained from immunoassays performed for a marker panel to rule in or out certain diagnoses.

Identification of Marker Panels

Methods and systems for the identification of one or more markers for the diagnosis, and in particular for the differential diagnosis, of disease have been described previously. Suitable methods for identifying markers useful for the diagnosis of disease states are described in detail in U.S. Provisional Patent Application No. 60/436,392, entitled METHOD AND SYSTEM FOR DISEASE DETECTION USING MARKER COMBINATIONS, filed Dec. 24, 2002, and U.S. patent application Ser. No. 10/331,127, entitled METHOD AND SYSTEM FOR DISEASE DETECTION USING MARKER COMBINATIONS, filed Dec. 27, 2002, each of which is hereby incorporated by reference in its entirety, including all tables, figures, and claims. One skilled in the art will also recognize that univariate analysis of markers can be performed and the data from the univariate analyses of multiple markers can be combined to form panels of markers to differentiate different disease conditions.

In developing a panel of markers useful in diagnosis, data for a number of potential markers may be obtained from a group of subjects by testing for the presence or level of certain markers. The group of subjects is divided into two sets, and preferably the first set and the second set each have an approximately equal number of subjects. The first set includes subjects who have been confirmed as having a disease or, more generally, being in a first condition state. For example, this first set of patients may be those that have recently had a stroke, or may be those having a specific type of stroke (e.g., thrombotic, embolic, lacunar, hypoperfusion, intracerebral hemorrhage, and subarachnoid hemorrhage types of strokes). The confirmation of this condition state may be made through a more rigorous and/or expensive testing such as MRI or CT. Hereinafter, subjects in this first set will be referred to as "diseased".

The second set of subjects are simply those who do not fall within the first set. Subjects in this second set may be "non-diseased;" that is, normal subjects. Alternatively, subjects in this second set may be selected to exhibit one symptom or a constellation of symptoms that mimic those symptoms exhibited by the "diseased" subjects. In the case of neurological disorders, for example, the skilled artisan will understand that neurologic dysfunction is a common symptom in various systemic disorders (e.g., alcoholism, vascular disease, stroke, a specific type of stroke (e.g., thrombotic, embolic, lacunar, hypoperfusion, intracerebral hemorrhage, and subarachnoid hemorrhage types of strokes) autoimmunity, metabolic disorders, aging, etc.).

Specific neurologic dysfunctions or "stroke-associated symptoms" may include, but are not limited to, pain, headache, aphasia, apraxia, agnosia, amnesia, stupor, confusion, vertigo, coma, delirium, dementia, seizure, migraine insomnia, hypersomnia, sleep apnea, tremor, dyskinesia, paralysis, visual disturbances, diplopia, paresthesias, dysarthria, hemiplegia, hemianesthesia, hemianopia, etc. Patients exhibiting one or more of these symptoms but that have not suffered from a stroke are referred to herein as "stroke mimics". Conditions within the differential diagnosis of stroke include brain tumor (including primary and metastatic disease), aneurysm, electrocution, burns, infections (e.g., meningitis), cerebral hypoxia, head injury (including concussion), stress, dehydration, nerve palsy (cranial or peripheral), hypoglycemia, migraine, multiple sclerosis, peripheral vascular disease, peripheral neuropathy, seizure (including grand mal seizure), subdural hematoma, syncope, and transient unilateral weakness. Preferred markers and marker panels are those that can distinguish stroke from these stroke mimicking conditions.

The data obtained from subjects in these sets includes levels of a plurality of markers. Preferably, data for the same set of markers is available for each patient. This set of markers may include all candidate markers which may be suspected as being relevant to the detection of a particular disease or condition. Actual known relevance is not required. Embodiments of the methods and systems described herein may be used to determine which of the candidate markers are most relevant to the diagnosis of the disease or condition. The levels of each marker in the two sets of subjects may be distributed across a broad range, e.g., as a Gaussian distribution. However, no distribution fit is required.

As noted above, a marker often is incapable of definitively identifying a patient as either diseased or non-diseased. For example, if a patient is measured as having a marker level that falls within the overlapping region, the results of the test will be useless in diagnosing the patient. An artificial cutoff may be used to distinguish between a positive and a negative test result for the detection of the disease or condition. Regardless of where the cutoff is selected, the effectiveness of the single marker as a diagnosis tool is unaffected. Changing the cutoff merely trades off between the number of false positives and the number of false negatives resulting from the use of the single marker. The effectiveness of a test having such an overlap is often expressed using a ROC (Receiver Operating Characteristic) curve. ROC curves are well known to those skilled in the art.

The horizontal axis of the ROC curve represents (1-specificity), which increases with the rate of false positives. The vertical axis of the curve represents sensitivity, which increases with the rate of true positives. Thus, for a particular cutoff selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

As discussed above, the measurement of the level of a single marker may have limited usefulness. The measurement of additional markers provides additional information, but the difficulty lies in properly combining the levels of two potentially unrelated measurements. In the methods and systems according to embodiments of the present invention, data relating to levels of various markers for the sets of diseased and non-diseased patients may be used to develop a panel of markers to provide a useful panel response. The data may be provided in a database such as Microsoft Access, Oracle, other SQL databases or simply in a data file. The database or data file may contain, for example, a patient identifier such as a name or number, the levels of the various markers present, and whether the patient is diseased or non-diseased.

Next, an artificial cutoff region may be initially selected for each marker. The location of the cutoff region may initially be selected at any point, but the selection may affect the optimization process described below. In this regard, selection near a suspected optimal location may facilitate faster convergence of the optimizer. In a preferred method, the cutoff region is initially centered about the center of the overlap region of the two sets of patients. In one embodiment, the cutoff region may simply be a cutoff point. In other embodiments, the cutoff region may have a length of greater than zero. In this regard, the cutoff region may be defined by a center value and a magnitude of length. In practice, the initial selection of the limits of the cutoff region may be determined according to a pre-selected percentile of each set of subjects. For example, a point above which a pre-selected percentile of diseased patients are measured may be used as the right (upper) end of the cutoff range.

Each marker value for each patient may then be mapped to an indicator. The indicator is assigned one value below the cutoff region and another value above the cutoff region. For example, if a marker generally has a lower value for non-diseased patients and a higher value for diseased patients, a zero indicator will be assigned to a low value for a particular marker, indicating a potentially low likelihood of a positive diagnosis. In other embodiments, the indicator may be calculated based on a polynomial. The coefficients of the polynomial may be determined based on the distributions of the marker values among the diseased and non-diseased subjects.

The relative importance of the various markers may be indicated by a weighting factor. The weighting factor may initially be assigned as a coefficient for each marker. As with the cutoff region, the initial selection of the weighting factor may be selected at any acceptable value, but the selection may affect the optimization process. In this regard, selection near a suspected optimal location may facilitate faster convergence of the optimizer. In a preferred method, acceptable weighting coefficients may range between zero and one, and an initial weighting coefficient for each marker may be assigned as 0.5. In a preferred embodiment, the initial weighting coefficient for each marker may be associated with the effectiveness of that marker by itself. For example, a ROC curve may be generated for the single marker, and the area under the ROC curve may be used as the initial weighting coefficient for that marker.

Next, a panel response may be calculated for each subject in each of the two sets. The panel response is a function of the indicators to which each marker level is mapped and the weighting coefficients for each marker. In a preferred embodiment, the panel response (R) for a each subject (j) is expressed as:

$$R_j = \Sigma w_i I_{ij},$$

where i is the marker index, j is the subject index, $w_i$ is the weighting coefficient for marker i, I is the indicator value to which the marker level for marker i is mapped for subject j, and $\Sigma$ is the summation over all candidate markers i.

One advantage of using an indicator value rather than the marker value is that an extraordinarily high or low marker levels do not change the probability of a diagnosis of diseased or non-diseased for that particular marker. Typically, a marker value above a certain level generally indicates a certain condition state. Marker values above that level indicate the condition state with the same certainty. Thus, an extraordinarily high marker value may not indicate an extraordinarily high probability of that condition state. The use of an indicator which is constant on one side of the cutoff region eliminates this concern.

The panel response may also be a general function of several parameters including the marker levels and other factors including, for example, race and gender of the patient. Other factors contributing to the panel response may include the slope of the value of a particular marker over time. For example, a patient may be measured when first arriving at the hospital for a particular marker. The same marker may be measured again an hour later, and the level of change may be reflected in the panel response. Further, additional markers may be derived from other markers and may contribute to the value of the panel response. For example, the ratio of values of two markers may be a factor in calculating the panel response.

Having obtained panel responses for each subject in each set of subjects, the distribution of the panel responses for each set may now be analyzed. An objective function may be defined to facilitate the selection of an effective panel. The objective function should generally be indicative of the effectiveness of the panel, as may be expressed by, for example, overlap of the panel responses of the diseased set of subjects and the panel responses of the non-diseased set of subjects. In this manner, the objective function may be optimized to maximize the effectiveness of the panel by, for example, minimizing the overlap.

In a preferred embodiment, the ROC curve representing the panel responses of the two sets of subjects may be used to define the objective function. For example, the objective function may reflect the area under the ROC curve. By maximizing the area under the curve, one may maximize the effectiveness of the panel of markers. In other embodiments, other features of the ROC curve may be used to define the objective function. For example, the point at which the slope of the ROC curve is equal to one may be a useful feature. In other embodiments, the point at which the product of sensitivity and specificity is a maximum, sometimes referred to as the "knee," may be used. In an embodiment, the sensitivity at the knee may be maximized. In further embodiments, the sensitivity at a predetermined specificity level may be used to define the objective function. Other embodiments may use the specificity at a predetermined sensitivity level may be used. In still other embodiments, combinations of two or more of these ROC-curve features may be used.

It is possible that one of the markers in the panel is specific to the disease or condition being diagnosed. When such markers are present at above or below a certain threshold, the panel response may be set to return a "positive" test result. When the threshold is not satisfied, however, the levels of the marker may nevertheless be used as possible contributors to the objective function.

An optimization algorithm may be used to maximize or minimize the objective function. Optimization algorithms are well-known to those skilled in the art and include several commonly available minimizing or maximizing functions including the Simplex method and other constrained optimization techniques. It is understood by those skilled in the art that some minimization functions are better than others at searching for global minimums, rather than local minimums. In the optimization process, the location and size of the cutoff region for each marker may be allowed to vary to provide at least two degrees of freedom per marker. Such variable parameters are referred to herein as independent variables. In a preferred embodiment, the weighting coefficient for each marker is also allowed to vary across iterations of the optimization algorithm. In various embodiments, any permutation of these parameters may be used as independent variables.

In addition to the above-described parameters, the sense of each marker may also be used as an independent variable. For example, in many cases, it may not be known whether a higher level for a certain marker is generally indicative of a diseased state or a non-diseased state. In such a case, it may be useful to allow the optimization process to search on both sides. In practice, this may be implemented in several ways. For example, in one embodiment, the sense may be a truly separate independent variable which may be flipped between positive and negative by the optimization process. Alternatively, the sense may be implemented by allowing the weighting coefficient to be negative.

The optimization algorithm may be provided with certain constraints as well. For example, the resulting ROC curve may be constrained to provide an area-under-curve of greater than a particular value. ROC curves having an area under the curve of 0.5 indicate complete randomness, while an area under the curve of 1.0 reflects perfect separation of the two sets. Thus, a minimum acceptable value, such as 0.75, may be used as a constraint, particularly if the objective function does not incorporate the area under the curve. Other constraints may include limitations on the weighting coefficients of particular markers. Additional constraints may limit the sum of all the weighting coefficients to a particular value, such as 1.0.

The iterations of the optimization algorithm generally vary the independent parameters to satisfy the constraints while minimizing or maximizing the objective function. The number of iterations may be limited in the optimization process. Further, the optimization process may be terminated when the difference in the objective function between two consecutive iterations is below a predetermined threshold, thereby indicating that the optimization algorithm has reached a region of a local minimum or a maximum.

Thus, the optimization process may provide a panel of markers including weighting coefficients for each marker and cutoff regions for the mapping of marker values to indicators. In order to develop lower-cost panels which require the measurement of fewer marker levels, certain markers may be eliminated from the panel. In this regard, the effective contribution of each marker in the panel may be determined to identify the relative importance of the markers. In one embodiment, the weighting coefficients resulting from the optimization process may be used to determine the relative importance of each marker. The markers with the lowest coefficients may be eliminated.

In certain cases, the lower weighting coefficients may not be indicative of a low importance. Similarly, a higher weighting coefficient may not be indicative of a high importance. For example, the optimization process may result in a high coefficient if the associated marker is irrelevant to the diagnosis. In this instance, there may not be any advantage that will drive the coefficient lower. Varying this coefficient may not affect the value of the objective function.

Individual panel response values may also be used as markers in the methods described herein. For example, a panel may be constructed from a plurality of markers, and each marker of the panel may be described by a function and a weighting factor to be applied to that marker (as determined by the methods described above). Each individual marker level is determined for a sample to be tested, and that level is applied to the predetermined function and weighting factor for that particular marker to arrive at a sample value for that marker. The sample values for each marker are added together to arrive at the panel response for that particular sample to be tested. For a "diseased" and "non-diseased" group of patients, the resulting panel responses may be treated as if they were just levels of another disease marker.

One could use such a method to define new "markers" based on panel responses, and even to determine a "panel response of panel responses." For example, one may divide stroke subjects and non-stroke subjects as follows: (1) ischemic stroke; (2) hemorrhagic stroke; (3) normals; (4) TIAs; (5) other stroke mimics. One would define a first panel constructed from a plurality of markers as described above, and obtain the panel responses from this first panel for all the subjects. Then, the members of any one of these 5 groups may be compared to the panel responses of the members of any other of these groups to define a function and weighting factor that best differentiates these two groups based on the panel responses. This can be repeated as all 5 groups are compared pairwise. The "markers" used to define a second panel might include any or all of the following as a new "marker": ischemic stroke versus normals as marker 1; hemorrhagic stroke versus normals as marker 2; ischemic stroke versus TIAs as marker 3; hemorrhagic stroke versus TIAs as marker 4; ischemic stroke versus other mimics as marker 5; and hemorrhagic stroke versus other mimics as marker 6.

Measures of test accuracy may be obtained as described in Fischer et al., *Intensive Care Med.* 29: 1043-51, 2003, and used to determine the effectiveness of a given marker or panel of markers. These measures include sensitivity and specificity, predictive values, likelihood ratios, diagnostic odds ratios, and ROC curve areas. As discussed above, suitable tests may exhibit one or more of the following results on these various measures:

at least 75% sensitivity, combined with at least 75% specificity;
ROC curve area of at least 0.7, more preferably at least 0.8, even more preferably at least 0.9, and most preferably at least 0.95; and/or
a positive likelihood ratio (calculated as sensitivity/(1-specificity)) of at least 5, more preferably at least 10, and most preferably at least 20, and a negative likelihood ratio (calculated as (1-sensitivity)/specificity) of less than or equal to 0.3, more preferably less than or equal to 0.2, and most preferably less than or equal to 0.1.

Selection of Antibodies

The generation and selection of antibodies may be accomplished several ways. For example, one way is to purify polypeptides of interest or to synthesize the polypeptides of interest using, e.g., solid phase peptide synthesis methods well known in the art. See, e.g., *Guide to Protein Purification*, Murray P. Deutcher, ed., *Meth. Enzymol.* Vol 182 (1990); Solid Phase Peptide Synthesis, Greg B. Fields ed., *Meth. Enzymol.* Vol 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be injected, for example, into mice or rabbits, to generate polyclonal or monoclonal antibodies. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In addition, numerous publications have reported the use of phage display technology to produce and screen libraries of polypeptides for binding to a selected target. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

Selecting a Treatment Regimen

The appropriate treatments for various types of stroke may be large and diverse. However, once a diagnosis is obtained, the clinician can readily select a treatment regimen that is compatible with the diagnosis. For example, the U.S. Food and Drug Administration has approved the clot-dissolving drug tissue plasminogen activator (tPA) to treat ischemic stroke, which constitutes 70-80 percent of all strokes. tPA carries a risk of bleeding in the brain, but its benefits outweigh the risks when an experienced doctor uses it properly. Not every stroke patient, particularly those having a hemorrhagic stroke, should be treated with tPA. tPA is effective only if given promptly. For maximum benefit, the therapy must be started within three hours of the onset of stroke symptoms, making rapid diagnosis and differentiation of stroke and stroke type critical.

This need for speed in stroke evaluation is often referred to with the shorthand Time is brain, as early treatment (within hours of stroke onset) is the single most critical factor likely to improve outcome with modern treatments. The National Institute of Neurological Disorders and Stroke has established the following goals for evaluation of stroke patients in an emergency department:

A physician should evaluate a stroke patient within 10 minutes of arrival at the ED doors.

A physician with expertise in the management of stroke should be available or notified within 15 minutes of patient arrival. Depending on the protocol established this may be accomplished by activating a stroke team.

A CT scan of the head should begin within 25 minutes of arrival. The CT interpretation should be obtained within 45 minutes of arrival. This gives adequate time to perform the scan, process the images, and interpret the results.

For ischemic stroke, treatment should be initiated within 60 minutes. There was clear consensus on this door-to-treatment guideline among participants in both the Emergency Department Panel and the Acute Hospital Care Panel.

The time from patient arrival at the ED to placement in a monitored bed should not exceed 3 hours.

Accordingly, the present invention provides methods of early differential diagnosis to allow for appropriate intervention in acute time windows (i.e., when tPA should be administered for ischemic stroke, but not hemorragic stroke). Invention methods can further be combined with CT scan(s), wherein a CT scan can be used to rule out hemorrhagic stroke, and invention methods can be used to diagnose and differentiate other types of stroke. Later time windows can further be used to determine probability of proceeding to vasospasm.

The skilled artisan is aware of appropriate treatments for numerous diseases discussed in relation to the methods of diagnosis described herein. See, e.g., *Merck Manual of Diagnosis and Therapy*, 17$^{th}$ Ed. Merck Research Laboratories, Whitehouse Station, N.J., 1999.

EXAMPLES

The following examples serve to illustrate the present invention. These examples are in no way intended to limit the scope of the invention.

Example 1

Blood Sampling

Blood specimens were collected by trained study personnel using EDTA as the anticoagulant and centrifuged for greater than or equal to 10 minutes. The plasma component was transferred into a sterile cryovial and frozen at −20° C. or colder. Clinical histories were available for each of the patients to aid in the statistical analysis of the assay data.

Example 2

Biochemical Analyses

Markers were measured using standard immunoassay techniques. These techniques involved the use of antibodies to specifically bind the protein targets. A monoclonal antibody directed against a selected marker was biotinylated using N-hydroxysuccinimide biotin (NHS-biotin) at a ratio of about 5 NHS-biotin moieties per antibody. The antibody-biotin conjugate was then added to wells of a standard avidin 384 well microtiter plate, and antibody conjugate not bound to the plate was removed. This formed the "anti-marker" in the microtiter plate. Another monoclonal antibody directed against the same marker was conjugated to alkaline phosphatase using succinimidyl 4-[N-maleimidomethyl]-cyclohexane-1-carboxylate (SMCC) and N-succinimidyl 3-[2-pyridyldithio]propionate (SPDP) (Pierce, Rockford, Ill.).

Immunoassays were performed on a TECAN Genesis RSP 200/8 Workstation. Biotinylated antibodies were pipetted into microtiter plate wells previously coated with avidin and incubated for 60 mm. The solution containing unbound antibody was removed, and the cells were washed with a wash buffer, consisting of 20 mM borate (pH 7.42) containing 150 mM NaCl, 0.1% sodium azide, and 0.02% TWEEN®-20 surface active agent (ICI Americas). The plasma samples (10 µL) were pipeted into the microtiter plate wells, and incubated for 60 min. The sample was then removed and the wells were washed with a wash buffer. The antibody-alkaline phosphatase conjugate was then added to the wells and incubated for an additional 60 min, after which time, the antibody conjugate was removed and the wells were washed with a wash buffer. A substrate, (ATTOPHOS®, Promega, Madison, Wis.) was added to the wells, and the rate of formation of the fluorescent product was related to the concentration of the marker in the patient samples.

Example 3

Statistical Analyses

Three cohorts were classified as ischemic stroke, hemorrhagic stroke, and normal, based on clinical diagnosis. Plasma samples were measured using two-site sandwich immunoassays designed to detect β-chimerin, myeloperoxidase, NDKA, Nogo receptor, RAGE, RNA-BP, and UFDP1H, and a sandwich assay using a single antibody for nitrotyrosine. Units are reported as ng/mL (MPO, RNA-BP, RAGE, Nogo receptor, UFDP1H, β-chimerin, and NDKA,), and nM (nitrotyrosine).

Exemplary receiver operator (ROC) curve analysis is summarized in the following table:

| Marker | N(nondiseased) | N(disease) | ROC curve Area | Sens (at 93% specificity) |
|---|---|---|---|---|
| MPO | 98 | 61 | 0.88 | 62.3% |
| RNA-BP | 99 | 117 | 0.80 | 60.7% |
| RAGE | 99 | 117 | 0.57 | 18.8% |
| NOGO Receptor | 99 | 52 | 0.60 | 21.2% |
| UFDP1H | 99 | 58 | 0.39 | 12.1% |
| β-chimerin | 99 | 61 | 0.54 | 16.4% |
| NDKA | 99 | 63 | 0.80 | 58.7% |
| Nitrotyrosine | 19 | 10 | 0.64 | 30.0% |

"nondiseased" group = Age-Matched Normals
"diseased" group = Ischemic and Hemorrhagic stroke)

FIGS. 1A-G provide "box and whisker" plots calculated from the assay data using SPSS 10.1 software (SPSS, Inc.) Hem=diagnosis of hemorrhagic stroke; Isc=diagnosis of ischemic stroke; Normal=age-matched normals.

The non-parametric Mann Whitney U statistic for intergroup comparison and Wilcoxon Signed-Rank test was used to compare amongst the various cohorts. The following data was obtained (U=Mann-Whitney U; W=Wilcoxon W; Z=Mann-Whitney Z; P=2-tailed significance):

| | N | Mean Rank | Sum of Ranks | U | W | Z | P |
|---|---|---|---|---|---|---|---|
| Normal vs. Ischemic Stroke | | | | | | | |
| β-Chimerin | | | | | | | |
| Normal | 99 | 69.30 | 6861 | 1911 | 6861 | −1.16 | 0.25 |
| Ischemic | 43 | 76.56 | 3292 | | | | |
| Total | 142 | | | | | | |
| MPO | | | | | | | |
| Normal | 98 | 55.12 | 5402 | 551 | 5402 | −6.97 | <0.001 |
| Ischemic | 43 | 107.2 | 4610 | | | | |
| Total | 141 | | | | | | |
| NDKA | | | | | | | |
| Normal | 99 | 58.67 | 5809 | 859 | 5809 | −5.64 | <0.001 |
| Ischemic | 43 | 101.03 | 4345 | | | | |
| Total | 142 | | | | | | |
| Nogo Receptor | | | | | | | |
| Normal | 99 | 62.36 | 6174 | 1224 | 6172 | −2.58 | 0.01 |
| Ischemic | 35 | 82.04 | 2872 | | | | |
| Total | 134 | | | | | | |
| RAGE | | | | | | | |
| Normal | 99 | 78.32 | 7754 | 2804 | 7754 | −2.38 | 0.02 |
| Ischemic | 72 | 96.56 | 6953 | | | | |
| Total | 171 | | | | | | |
| RNA-BP | | | | | | | |
| Normal | 99 | 60.73 | 6013 | 1063 | 6013 | −7.83 | <0.001 |
| Ischemic | 72 | 120.74 | 8694 | | | | |
| Total | 171 | | | | | | |
| UFDP1H | | | | | | | |
| Normal | 99 | 73.66 | 7293 | 1618 | 2438 | −1.69 | 0.09 |
| Ischemic | 40 | 60.94 | 2438 | | | | |
| Total | 139 | | | | | | |
| Normal vs. Hemorrhagic Stroke | | | | | | | |
| β-Chimerin | | | | | | | |
| Normal | 99 | 60.21 | 5961 | 871 | 1061 | −0.64 | 0.52 |
| Hemorrhagic | 19 | 55.82 | 1061 | | | | |
| Total | 118 | | | | | | |
| MPO | | | | | | | |
| Normal | 98 | 51.51 | 5048 | 197 | 5048 | −5.43 | <0.001 |
| Hemorrhagic | 19 | 97.63 | 1855 | | | | |
| Total | 117 | | | | | | |
| NDKA | | | | | | | |
| Normal | 99 | 55.69 | 5514 | 564 | 5514 | −3.03 | 0.002 |
| Hemorrhagic | 20 | 81.32 | 1627 | | | | |
| Total | 119 | | | | | | |
| Nogo Receptor | | | | | | | |
| Normal | 99 | 58.66 | 5807 | 826 | 979 | −0.12 | 0.90 |
| Hemorrhagic | 17 | 57.59 | 979 | | | | |
| Total | 116 | | | | | | |
| RAGE | | | | | | | |
| Normal | 99 | 71.93 | 7122 | 2172 | 7122 | −0.24 | 0.81 |
| Hemorrhagic | 45 | 73.74 | 3319 | | | | |
| Total | 144 | | | | | | |
| RNA-BP | | | | | | | |
| Normal | 99 | 62.33 | 6171 | 1221 | 6171 | −4.49 | <0.001 |
| Hemorrhagic | 46 | 95.96 | 4414 | | | | |
| Total | 145 | | | | | | |
| UFDP1H | | | | | | | |
| Normal | 99 | 62.71 | 6208 | 623 | 813 | −2.33 | 0.02 |
| Hemorrhagic | 19 | 42.79 | 813 | | | | |
| Total | 118 | | | | | | |
| Normal vs. All Stroke | | | | | | | |
| β-Chimerin | | | | | | | |
| Normal | 99 | 79.51 | 7872 | 2193 | 7872 | −0.63 | 0.53 |
| Stroke | 62 | 83.38 | 5170 | | | | |
| Total | 161 | | | | | | |
| MPO | | | | | | | |
| Normal | 98 | 57.13 | 5599 | 748 | 5599 | −8.02 | <0.001 |
| Stroke | 62 | 117.44 | 7282 | | | | |
| Total | 160 | | | | | | |
| NDKA | | | | | | | |
| Normal | 99 | 64.36 | 6372 | 1422 | 6372 | −5.83 | <0.001 |
| Stroke | 63 | 108.43 | 6831 | | | | |
| Total | 162 | | | | | | |
| Nogo Receptor | | | | | | | |
| Normal | 99 | 71.02 | 7030 | 2081 | 7031 | −1.93 | 0.05 |
| Stroke | 52 | 85.49 | 4446 | | | | |
| Total | 151 | | | | | | |
| RAGE | | | | | | | |
| Normal | 99 | 100.25 | 9925 | 4975 | 9925 | −1.78 | 0.07 |
| Stroke | 117 | 115.48 | 13511 | | | | |
| Total | 216 | | | | | | |
| RNA-BP | | | | | | | |
| Normal | 99 | 73.07 | 7234 | 2284 | 7234 | −7.72 | <0.001 |
| Stroke | 118 | 139.15 | 16420 | | | | |
| Total | 217 | | | | | | |
| UFDP1H | | | | | | | |
| Normal | 99 | 86.37 | 8551 | 2241 | 4011 | −2.44 | 0.02 |
| Stroke | 59 | 67.97 | 4011 | | | | |
| Total | 158 | | | | | | |
| Ischemic vs. Hemorrhagic Stroke | | | | | | | |
| β-Chimerin | | | | | | | |
| Ischemic | 43 | 33.13 | 1425 | 339 | 529 | −1.29 | 0.20 |
| Hemorrhagic | 19 | 27.82 | 529 | | | | |
| Total | 62 | | | | | | |
| MPO | | | | | | | |
| Ischemic | 43 | 31.33 | 1347 | 401 | 1347 | −0.12 | 0.91 |
| Hemorrhagic | 19 | 31.89 | 606 | | | | |
| Total | 62 | | | | | | |

-continued

|  | N | Mean Rank | Sum of Ranks | U | W | Z | P |
|---|---|---|---|---|---|---|---|
| NDKA | | | | | | | |
| Ischemic | 43 | 34.19 | 1470 | 336 | 546 | −1.39 | 0.17 |
| Hemorrhagic | 20 | 27.30 | 546 | | | | |
| Total | 63 | | | | | | |
| Nogo Receptor | | | | | | | |
| Ischemic | 35 | 29.03 | 1016 | 209 | 362 | −1.73 | 0.08 |
| Hemorrhagic | 17 | 21.29 | 362 | | | | |
| Total | 52 | | | | | | |
| RAGE | | | | | | | |
| Ischemic | 72 | 62.69 | 4514 | 1354 | 2389 | −1.49 | 0.14 |
| Hemorrhagic | 45 | 53.09 | 2389 | | | | |
| Total | 117 | | | | | | |
| RNA-BP | | | | | | | |
| Ischemic | 72 | 65.94 | 4748 | 1193 | 2274 | −2.56 | 0.01 |
| Hemorrhagic | 46 | 49.42 | 2274 | | | | |
| Total | 118 | | | | | | |
| UFDP1H | | | | | | | |
| Ischemic | 40 | 31.92 | 1277 | 303 | 493 | −1.25 | 0.21 |
| Hemorrhagic | 19 | 25.95 | 493 | | | | |
| Total | 59 | | | | | | |
| Nitrotyrosine | | | | | | | |
| Ischemic | 15 | 11.07 | 166 | 29 | 44 | −0.76 | 0.45 |
| Hemorrhagic | 5 | 8.8 | 44 | | | | |
| Total | 20 | | | | | | |

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of diagnosing stroke in a subject, comprising:
performing an assay by contacting a sample of blood, serum, or plasma from said subject with an antibody that binds myeloperoxidase, and detecting a signal indicative of the presence or amount of polypeptides bound to said antibody; and
correlating the result of the assay to the occurrence or nonoccurrence of a stroke in said subject, wherein stroke includes isehemic stroke and hemorrhagic stroke.

2. A method according to claim 1, further comprising performing one or more additional assays for one or more additional markers selected from the group consisting of adenylate kinase, brain-derived neurotrophic factor, calbindin-D, ciliary neurtotrophic factor, creatine kinase-BB, glial fibrillary acidic protein, lactate dehydrogenase, myelin basic protein, one or more isoforms of nerve growth factor, neural cell adhesion molecule, neurokinin A, neuron-specific enolase, neurotensin, neuropeptide Y, neurotrophin-3, one or more isoforms of protein kinase C, proteolipid protein, S-100β, secretagogin, 14-3-3, thrombomodulin, an acute phase reactant, A-type natriuretic peptide, B-type natriuretic peptide, NT-pro-B-type natriuretic peptide, pro-B-type natriuretic peptide, C-type natriuretic peptide, adrenomedullin, endothelin-1, endothelin-2, endothelin-3, β-thromboglobulin, cardiac troponin I, caspase-3, creatine kinase-MB, D-dimer, fibrinopeptide A, head activator, hemoglobin α2 chain, interleukin-8, myoglobin, plasmin-α-2-antiplasmin complex, platelet factor 4, protbrombin fragment 1+2, thrombin-antithrombin III complex, tissue factor, vascular endothelial growth factor, and one or more forms of von Willebrand factor,
wherein each of said additional assays comprises contacting a sample of bodily fluid from said subject with an antibody that binds one of said additional markers, and detecting a signal indicative of the presence or amount of polypeptides bound to said antibody, and
wherein said correlating step comprises correlating the result of the assay performed and the results of said additional assays performed to the occurrence or nonoccurrence of a stroke in said subject.

3. A method according to claim 2, wherein said acute phase reactant is selected from the group consisting of C-reactive protein, E-selectin, insulin-like growth factor-1, intercellular adhesion molecule-1, interleukin-1β, interleukin-1 receptor antagonist, interleukin-6, matrix metalloproteinase-3, monocyte chemotactic protein-1, transforming growth factor β, tumor necrosis factor α, and vascular cell adhesion molecule.

4. A method according to claim 1, wherein said correlating step comprises correlating whether the results of the assay(s) performed and the results of a CT scan performed on said subject for evaluation of hemorrhagic stroke to the occurrence or nonoccurrence of a stroke in said subject.

5. A method according to claim 2, wherein both the assay and the additional assay(s) are performed on the same sample obtained from said subject.

6. A method according to claim 2, wherein the assay and the additional assay(s) are performed on different samples obtained from said subject.

7. A method according to claim 1, wherein said correlating step comprises comparing a concentration of myeloperoxidase determined from said assay to a threshold level, wherein a concentration greater than said threshold level is indicative of an increased probability of the occurrence of a stroke, relative to a probability of the occurrence of a stroke indicated by a concentration less than said threshold level.

8. A method according to claim 1, further comprising performing an additional assay for B-type natriuretic peptide, wherein said additional assay comprises contacting a sample of bodily fluid from said subject with an antibody that binds B-type natriuretic peptide, and detecting a signal indicative of the presence or amount of B-type natriuretic peptide bound to said antibody, and
wherein said correlating step comprises correlating the result of the assay performed and the results of said additional assay performed to the occurrence or nonoccurrence of a stroke in said subject.

* * * * *

SEQUENCE LISTING

<160> NUMBER OF SEQ ID NOS: 7

<210> SEQ ID NO 1
<211> LENGTH: 108
<212> TYPE: PRT
<213> ORGANISM: Homo sapiens

<400> SEQUENCE: 1

His Pro Leu Gly Ser Pro Gly Ser Ala Ser Asp Leu Glu Thr Ser Gly
 1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
                100                 105

<210> SEQ ID NO 2
<211> LENGTH: 134
<212> TYPE: PRT
<213> ORGANISM: Homo sapiens

<400> SEQUENCE: 2

Met Asp Pro Gln Thr Ala Pro Ser Arg Ala Leu Leu Leu Leu Leu Phe
 1               5                  10                  15

Leu His Leu Ala Phe Leu Gly Gly Arg Ser His Pro Leu Gly Ser Pro
             20                  25                  30

Gly Ser Ala Ser Asp Leu Glu Thr Ser Gly Leu Gln Glu Gln Arg Asn
         35                  40                  45

His Leu Gln Gly Lys Leu Ser Glu Leu Gln Val Glu Gln Thr Ser Leu
     50                  55                  60

Glu Pro Leu Gln Glu Ser Pro Arg Pro Thr Gly Val Trp Lys Ser Arg
 65                  70                  75                  80

Glu Val Ala Thr Glu Gly Ile Arg Gly His Arg Lys Met Val Leu Tyr
                 85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttctcaagcc tcagacagtg                                                      20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctggatgca ggctactcta g                                                    21

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggtgtcgta agcttgaatt cagacacctc tgccgccacc atgag                          45

<210> SEQ ID NO 6

```
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggctggctt acctgcggcc ttagtgatgg tgatggtgat ggtcctcagg gcactgcagg      60
atg                                                                   63

<210> SEQ ID NO 7
<211> LENGTH: 12
<212> TYPE: PRT
<213> ORGANISM: Homo sapiens

<400> SEQUENCE: 7

Ala Gly Thr Ala Asp Cys Phe Trp Lys Tyr Cys Val
 1               5                  10
```